United States Patent [19]

Yokomoto et al.

[11] Patent Number: 5,399,553
[45] Date of Patent: * Mar. 21, 1995

[54] TRICYCLIC COMPOUND OR SALTS THEREOF, METHOD FOR PRODUCING THE SAME AND ANTI-MICROBIAL AGENT CONTAINING THE SAME

[75] Inventors: Masaharu Yokomoto; Akira Yazaki; Norihiro Hayashi; Shunso Hatono; Satoshi Inoue; Yasuhiro Kuramoto, all of Hiroshima, Japan

[73] Assignees: Wakunaga Seiyaku Kabushiki Kaisha; Fujisawa Pharmaceutical Company, Ltd., both of Osaka, Japan

[ * ] Notice: The portion of the term of this patent subsequent to Oct. 19, 2010 has been disclaimed.

[21] Appl. No.: 76,938

[22] Filed: Jun. 16, 1993

Related U.S. Application Data

[63] Continuation of Ser. No. 789,071, Nov. 7, 1991, abandoned, which is a continuation-in-part of Ser. No. 741,333, Aug. 7, 1991, Pat. No. 5,254,685.

[30] Foreign Application Priority Data

Aug. 9, 1990 [JP] Japan ................... 2-21190
Apr. 12, 1991 [JP] Japan ................... 3-80144
Jul. 4, 1991 [JP] Japan ................... 3-164356

[51] Int. Cl.$^6$ ............... A61K 37/02; A61K 31/55; A61K 31/50; C07D 471/06
[52] U.S. Cl. ................... 514/18; 514/212; 514/213; 514/214; 514/215; 514/216; 514/218; 514/222.2; 514/233.2; 514/248; 530/331; 540/575; 540/579; 540/580; 540/583; 540/586; 540/599; 544/60; 544/115; 544/230; 544/234

[58] Field of Search ................. 544/230, 234, 60, 115; 514/248, 222.2, 233.2, 212, 218, 213, 214, 215, 216, 18; 540/575, 599, 579, 580, 583, 586; 530/331

[56] References Cited

U.S. PATENT DOCUMENTS 4,801,584  1/1989  Yokose et al. ............... 514/183
4,864,023  9/1989  Yokose et al. ............... 544/66

FOREIGN PATENT DOCUMENTS 0115334  8/1984  European Pat. Off. .

Primary Examiner—Emily Bernhardt
Attorney, Agent, or Firm—Oblon, Spivak, McClelland, Maier & Neustadt

[57] ABSTRACT

A tricyclic compound represented by the general formula (1) and salts thereof are disclosed.

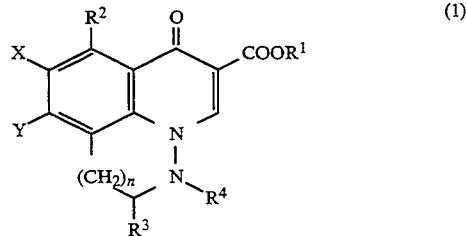

A method for producing the tricyclic compound and salts thereof, and an antimicrobial agent containing the tricyclic compound and salts thereof as an active ingredient are also disclosed.

5 Claims, No Drawings

TRICYCLIC COMPOUND OR SALTS THEREOF, METHOD FOR PRODUCING THE SAME AND ANTI-MICROBIAL AGENT CONTAINING THE SAME

This is a continuation of application Ser. No. 07/789,071, filed on Nov. 7, 1991, now abandoned, which is a continuation in part of application Ser. No. 07/741,333, filed on Aug. 7, 1991, now U.S. Pat. No. 5,254,685.

BACKGROUND OF THE INVENTION i) Field of the Invention

The present invention relates to a novel tricyclic compound having an excellent antimicrobial activity and oral absorbability and salts thereof, a method for producing the same and an antimicrobial agent containing the same.

ii) Description of the Background Art

Conventionally, in compounds including a pyridonecarboxylic acid as a basic skeleton, many compounds having an excellent antimicrobial activity and a wide antimicrobial spectrum are known as a useful synthetic antimicrobial drug or agent. For instance, norfloxacin (see Japanese Patent Laid-open (Kokai) No. 53-141286), enoxacin (see Japanese Patent Laid-open (Kokai) No. 55-31042), ofloxacin (see Japanese Patent Laid-open (Kokai) No. 57-46986), ciprofloxacin (see Japanese Patent Laid-open (Kokai) No. 58-76667) and the like are widely used as an infective disease remedy in clinical medicine.

However, these compounds are still insufficient in antimicrobial activity, enteron absorbability, metabolic stability, side-effects and the like, and hence a novel compound satisfying these requirements has been demanded.

SUMMARY OF THE INVENTION

Accordingly, it is an object of the present invention to provide a novel tricyclic compound in view of the aforementioned drawbacks of the prior art, which possesses excellent antimicrobial activity and oral absorbability.

It is another object of the present invention to provide a method for producing a tricyclic compound having excellent antimicrobial activity and oral absorbability.

It is a further object of the present invention to provide an antimicrobial agent containing a novel tricyclic compound having an excellent antimicrobial activity and oral absorbability.

In accordance with one aspect of the present invention, there is provided a tricyclic compound represented by a general formula (1) and salts thereof,

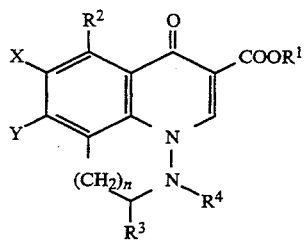

(1)

wherein $R^1$ is one of a hydrogen atom and a carboxyl protecting group; wherein $R^2$ is one of a hydrogen atom, a halogen atom, an amino group and a protected amino group; wherein $R^3$ is one of a hydrogen atom and a lower alkyl group; where, in $R^4$ is one of a hydrogen atom, a substituted or unsubstituted lower alkyl group, an acyl group and an aralkyl group; wherein X is one of a hydrogen atom and a halogen atom; wherein Y is one of a halogen atom, an amino group, a hydroxyl group, a cyclo-lower alkylamino group, a mono- or di- lower alkylamino group, a substituted or unsubstituted cyclic amino group, a substituted or unsubstituted lower alkyl group, a substituted or unsubstituted cyclo- lower alkenyl group, a group represented by a formula $R^5$—(CH$_2$)$_m$—A— wherein $R^5$ is one of a hydrogen atom, a substituted or unsubstituted amino group, a substituted or unsubstituted saturated heterocyclic group having a nitrogen atom and a substituted or unsubstituted lower cycloalkyl group, wherein A is one of an oxygen atom and a sulfur atom, and wherein m is an integer of 0 to 3, and a group represented by a formula $R^6$—SO$_2$O— wherein $R^6$ is a lower alkyl group, a halo-lower alkyl group, a phenyl group or a mono-, di- or tri-substituted phenyl group by a lower alkyl group; and wherein n is an integer of 0 to 2.

In accordance with another aspect of the present invention, there is provided a method for producing a tricyclic compound represented by the following general formula and salts thereof,

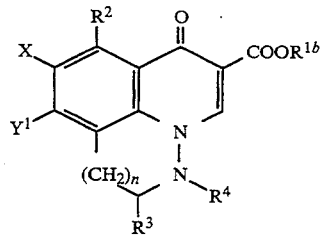

wherein $R^{1b}$ is one of a hydrogen atom and a lower alkyl group; wherein $R^2$ is one of a hydrogen atom, a halogen atom, an amino group and a protected amino group; wherein $R^3$ is one of a hydrogen atom and a lower alkyl group; wherein $R^4$ is one of a hydrogen atom, a substituted or unsubstituted lower alkyl group, an acyl group and aralkyl group; wherein X is one of a hydrogen atom and a halogen atom; wherein $Y^1$ is a halogen atom and a group represented by a formula $R^6$—SO$_2$O— wherein $R^6$ is a lower alkyl group, a halo-lower alkyl group, a phenyl group or a mono-, di- or tri-substituted phenyl group by a lower alkyl group, and wherein n is an integer of 0 to 2, comprising the steps of:

carrying out a cyclization of the compound represented by the following general formula.

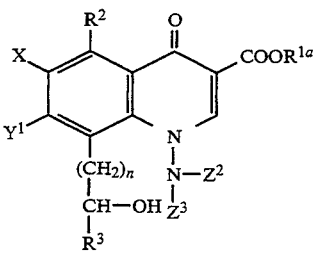

wherein $R^{1a}$ is a lower alkyl group; wherein $Z^2$ and $Z^3$ are either same or different and are one of a hydrogen atom, a substituted or unsubstituted lower alkyl group, an acyl group, an aralkyl group and an amino protecting group; and wherein R², R³, X, Y¹ and n are the same as described above, to prepare the compound represented by the following general formula,

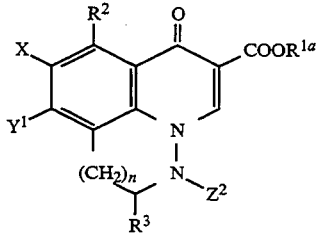

wherein R¹ᵃ, R², R³, X, Y¹, Z² and n are the same as described above;

and optionally followed by carrying out either an N-alkylation, N-acylation or N-aralkylation of the ring nitrogen atom;

and/or optionally followed by eliminating ester residue of the compound.

In accordance with a further aspect of the present invention, there is provided a method for producing a tricyclic compound represented by The following general formula and salts thereof,

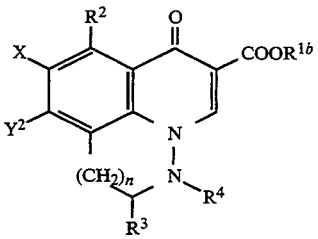

wherein R¹ᵇ is one of a hydrogen atom and a lower alkyl group; wherein R² is one of a hydrogen atom, a halogen atom, an amino group and a protected amino group; wherein R³ is one of a hydrogen atom and a lower alkyl group; wherein R⁴ is one of a hydrogen atom, a substituted or unsubstituted lower alkyl group, an acyl group and an aralkl group; wherein X is one of a hydrogen atom and a halogen atom; wherein Y² is one of an amino group, a cyclo- lower alkylamino group, a mono- or di- lower alkylamino group a substituted or unsubstituted cyclic amino group, a substituted or unsubstituted lower alkyl group, a substituted or unsubstituted cyclo- lower alkenyl group and a group represented by a formula R⁵—(CH₂)m—A— wherein R⁵ is one of a hydrogen atom, a substituted or unsubstituted amino group, a substituted or unsubstituted saturated heterocyclic group having a nitrogen atom and a substituted or unsubstituted lower cycloalkyl group, wherein A is one of an oxygen atom and a sulfur atom, and wherein m is an integer of 0 to 3, and wherein n is an integer of 0 to 2, comprising the steps of:

reacting the compound represented by the following general formula,

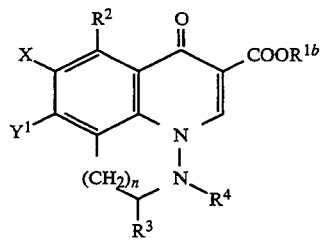

wherein Y¹ is a halogen atom or a group represented by a formula R⁶—SO₂O— wherein R⁶ is a lower alkyl group, a halo-lower alkyl group, a phenyl group or a mono-, di- or tri-substituted phenyl group by lower alkyl group; and wherein R¹ᵇ, R², R³, R⁴, X and n are the same as described above, with one of a compound represented by Y²—M wherein M is one of a hydrogen atom, an alkali metal atom and an organometallic compound with the proviso that M is an organometallic compound when Y² is a substituted or unsubstituted cyclo-lower alkenyl group; and wherein Y² is the same as described above, salts or an alkali metal alcoholate;

and optionally followed by eliminating ester residues of the object compound.

In accordance with still another aspect of the present invention, there is provided a method for producing a tricyclic compound represented by the following general formula and salts thereof,

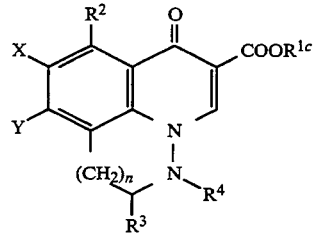

wherein R¹ᶜ is a carboxyl protecting group; wherein R² is one of a hydrogen atom, a halogen atom, an amino group and a protected amino group; wherein R³ is a hydrogen atom or a lower alkyl group; wherein R⁴ is one of a hydrogen atom, a substituted or unsubstituted lower alkyl group, an acyl group and an aralkyl group; wherein X is one of a hydrogen atom and a halogen atom; wherein Y is one of a halogen atom, an amino group, a hydroxyl group, a cyclo- lower alkylamino group, a mono- or di- lower alkylamino group, a substituted or unsubstituted cyclic amino group, a substituted or unsubstituted lower alkyl group, a substituted or unsubstituted cyclo- lower alkenyl group, a group represented by a formula R⁵—(CH₂)m—A— wherein R⁵ is one of a hydrogen atom, a substituted or unsubstituted amino group, a substituted or unsubstituted saturated heterocyclic group having a nitrogen atom and a substituted or unsubstituted lower cycloalkyl group, wherein A is one of an oxygen atom and a sulfur atom, and wherein m is an integer of 0 to 3, and a group represented by a formula R⁶—SO₂O— wherein R⁶ a lower alkyl group, a halo-lower alkyl group, a phenyl group and a mono-, di- or tri-substituted phenyl group by a lower alkyl group, and wherein n is an integer of 0 to 2, comprising the step of:

reacting the compound represented by the following general formula wherein $R^2$, $R^3$, $R^4$, X, Y and n are the same as described above,

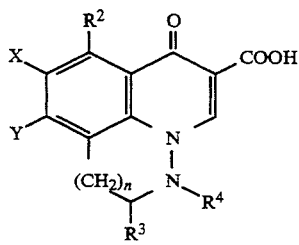

with one of a compound represented by $R^{1c}$—$X^1$ wherein $X^1$ is one of a hydroxyl group and a halogen atom; and wherein $R^{1c}$ is the same as described above.

In accordance with still another aspect of the present invention, there is provided an antimicrobial containing a tricyclic compound represented by general formula (1) and salts thereof as an active ingredient.

These and other objects, features and advantages of the present invention will be more fully appeared from the following description of the preferred embodiments.

DETAILED DESCRIPTION OF THE INVENTION AND PREFERRED EMBODIMENTS

The present invention will now be described in detail with reference to Examples thereof.

Researches for providing clinically excellent synthetic antimicrobial drugs or agents with improved antimicrobial activity, enteron absorbability, metabolic stability, side-effects and the like have been carried out. It has been found that a compound having a 1, 8-bridged quinolone carboxylic acid structure represented by the general formula (1) exhibited an excellent antimicrobial activity against gram-negatives and gram-positives and satisfied the above requirements to be useful for a synthetic antimicrobial drug or agent. This finding has led to the completion of the present invention. General formula (1) is shown as follows:

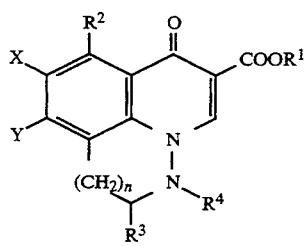

(1)

wherein $R^1$ is a hydrogen atom or a carboxyl protecting group, wherein $R^2$ is a hydrogen atom, a halogen atom, an amino group or a protected amino group, wherein $R^3$ is a hydrogen atom or a lower alkyl group, wherein $R^4$ is a hydrogen atom, a substituted or unsubstituted lower alkyl group, an acyl group or an aralkyl group, wherein X is a hydrogen atom or a halogen atom, wherein Y is a halogen atom, an amino group, a hydroxyl group, a cyclo- lower alkylamino group, a mono- or di- lower alkylamino group, a substituted or unsubstituted cyclic amino group, a substituted or unsubstituted lower alkyl group, a substituted or unsubstituted cyclo- lower alkenyl group, a group represented by a formula $R^5$—$(CH_2)m$—A— wherein $R^4$ is a hydrogen atom, a substituted or unsubstituted amino group, a substituted or unsubstituted saturated heterocyclic group having a nitrogen atom or a substituted or unsubstituted lower cycloalkyl group, A is an oxygen atom or sulfur atom, and m is an integer of 0 to 3, and a group represented by a formula $R^6$—$SO_2O$— wherein $R^6$ is a lower alkyl group, a halo-lower alkyl group, a phenyl group or a mono-, di- or tri-substituted phenyl group by a lower alkyl group, and wherein n is an integer of 0 to 2.

Hence, according to the present invention, there are provided a tricyclic compound represented by the general formula (1) or a salt thereof, a method for producing the tricyclic compound represented by the general formula (1) or the salt thereof, and an antimicrobial agent containing the tricyclic compound represented by the general formula (1) or the salt thereof as an active ingredient.

According to the present invention, the term "lower" of a substituent in general formula (1) means a group having 1 to 7 carbon atoms, preferably 1 to 5 carbon atoms when the substituent is a straight or branched chain group or a group having 3 to 7 carbon atoms when the substituent is a cyclic group.

The carboxyl protecting group represented by $R^1$ means any ester residue of a carboxylate which is readily cleaved to produce a corresponding carboxyl group. As examples of this, for instance, lower alkyl groups such as methyl group, ethyl group, n-propyl group, t-butyl group and the like, aralkyl groups such as benzyl group and the like, and aryl groups such as phenyl group and the like, which can be readily released by treating under a moderate condition in a hydrolysis, a catalytic reduction or the like; or lower alkanoyloxy- lower alkyl groups such as acetoxymethyl group, pivaloyloxymethyl group and the like, lower alkoxycarbonyloxy- lower alkyl groups such as methoxycarbonyloxymethyl group, 1-ethoxycarbonyloxyethyl group and the like, lower alkoxymethyl groups such as methoxymethyl group and the like, lactonyl groups such as phthalidyl group and the like, di- lower alkylamino- lower alkyl groups such as 1-dimethylaminoethyl group and the like, and (5-methyl-2-oxo-1,8-dioxol-4-yl)-methyl group, which can be readily released in vivo can be given.

As to the halogen atom represented by $R^2$, fluorine atom, chlorine atom, bromine atom and the like are given, and fluorine atom is preferable.

Appropriate groups for protecting an amino group to provide a protected amino group represented by $R^2$ include lower alkanoyl groups such as formyl group, acetyl group, propionyl group, hexanoyl group and the like; mono-, di- or tri- halo(lower) alkanoyl groups such as chloroacetyl group, bromoacetyl group, dichloroacetyl group, trifluoroacetyl group and the like; lower alkoxy-carbonyl groups such as propoxycarbonyl group, t-butoxycarbonyl group, t-pentyloxycarbonyl group, hexyloxycarbonyl group and the like; carbamoyl groups; aroyl groups such as benzoyl group, toluoyl group, naphthoyl group and the like; ar-(lower)alkanoyl groups such as phenylacetyl group, phenylpropinoyl group and the like; aryloxycarbonyl groups such as phenoxycarbonyl group, naphthyloxycarbonyl group and the like; aryloxy(lower)alkanoyl groups such as phenoxyacetyl group, phenoxypropiony group and the like; arylglyoxyloyl groups such as phenylglyoxyloyl group, naththylglyoxyloyl group and the like; ar(lower)alkoxy-carbonyl groups substituted or unsubstituted with a proper substituent such as benzyloxycarbonyl group, phenethyloxy-carbonyl group, p-nitrobenzyloxycarbonyl group, and the like; substituted or unsubstituted ar(lower)-alkylidene groups such as benzylidene group, hydroxy-benzylidene group and the like; ar(lower)alkyl groups such as mono- (or di- or tri-) phenyl(lower)alkyl group, for example, benzyl group, 1-phenylethyl group, benzhydryl group, trityl group or the like, and the like.

As regards the lower alkyl group represented by $R^3$, for example, methyl group, ethyl group and the like are given.

Regarding the substituted or unsubstituted lower alkyl group represented by $R^4$, for instance, in addition to lower alkyl groups such as methyl group, ethyl group, isopropyl group, t-butyl group, t-pentyl group or the like, lower alkyl groups substituted with a hydroxyl group, a halogen atom or a lower alkoxy group such as hydroxymethyl group, fluoromethyl group, methoxymethyl group or the like are given.

Relating to the acyl group represented by $R^4$, for example, lower alkanoyl groups such as formyl group, acetyl group and the like, lower alkoxycarbonyl groups such as methoxycarbonyl group, ethoxycarbonyl group and the like, and aromatic acyl groups such as benzoyl group, phenoxycarbonyl group and the like are given.

As examples of the aralkyl group represented by $R^4$, benzyl group, 1-phenylethyl group and the like are given.

As examples of the halogen atom represented by X, fluorine atom, chlorine atom, bromine atom and the like are given, and fluorine atom is preferable.

As regards the halogen atom represented by Y, the same atoms as those of X are given, and fluorine atom and chlorine atom are preferable. As to the cyclo- lower alkylamino group represented by Y, for instance, cyclopropylamino group, cyclobutylamino group and the like are given. Regarding the mono- or di- lower alkylamino group represented by Y, for example, methylamino group, dimetylamino group, benzylamino group and the like are given.

Further, as to the substituted or unsubstituted cyclic amino group represented by Y, either saturated cyclic amino groups or unsaturated cyclic amino groups can be used, and these groups may further include one or more hetero atoms such as nitrogen atoms, oxygen atoms, sulfur atoms and carbonyl carbons and may further have either a mono-, di- or tri-cyclic structure. Such cyclic amino groups are given as the following formulae (a')-(t).

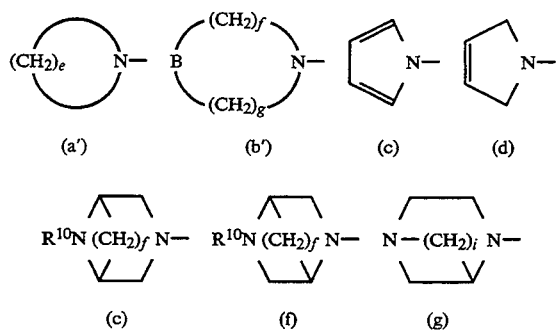

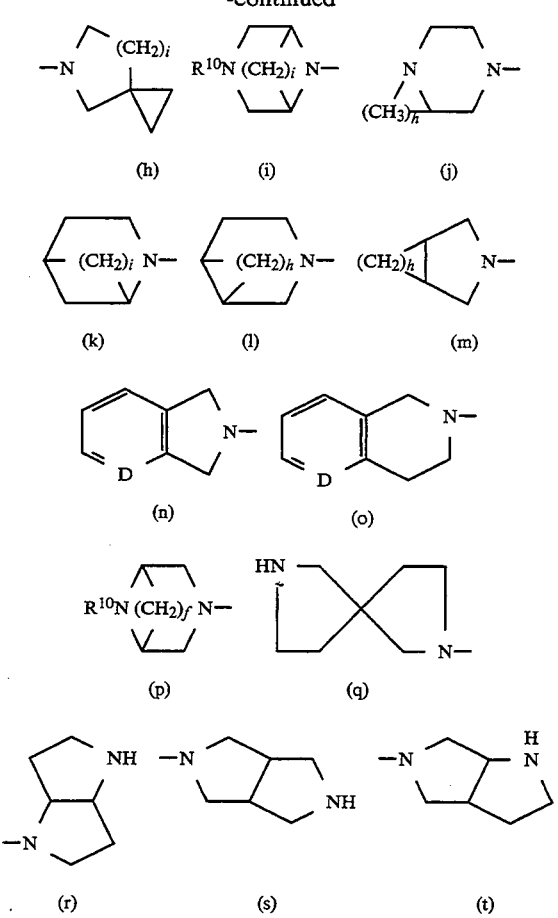

In these groups, B is an oxygen atom, a sulfur atom, $-NR^{10}$ or $-CONR^{10}$ wherein $R^{10}$ is a hydrogen atom, a hydroxyl group, a lower alkyl group, a cyclo- lower alkyl group, an aralkyl group, an alkenyl group, an acyl group or a hydroxy- lower alkyl group, D is CH or N, e is 3, 4 or 5, f is 1, 2 or 3, g is 0, 1 or 2, h is 3 or 4, i is 1 or 2.

The suitable substituent for these cyclic amino group includes a lower alkyl group, a lower alkenyl group, a lower aralkyl group, an aryl group, a hydroxyl group, a hydroxy-lower alkyl group, a substituted or unsubstituted amino group, a substituted or unsubstituted amino- lower alkyl group, a cyclic amino group as described above, an alkoxy group, an alkoxy- lower alkyl group, a halogen atom, a halo-lower alkyl group, an acyloxy group, an acyloxy- lower alkyl group, an acyl group, a carboxyl group, a carboxy- lower alkyl group, an alkoxycarbonyl- lower alkyl group, a mercapto group, a lower alkylthio group, a cyano group, a nitro group and the like.

For example, there are given methyl group, ethyl group, n-propyl group or the like for the lower alkyl group; vinyl group, allyl group or the like for the lower alkenyl group; benzyl group, 1-phenetyl group or the like for the lower aralkyl group; phenyl group or the like for the aryl group; hydroxymethyl group, hydroxyethyl group hydroxypropyl group or the like for the hydroxy- lower alkyl group; aminomethyl group, 1-aminoethyl group, 2-amino-ethyl group, 1-amino-1-methylethyl group or the like for the amino- lower alkyl group; methoxy group, ethoxy group, n-propoxy group or the like for the alkoxy group; methoxymethyl group, ethoxymethyl group or the like for the alkoxy- lower alkyl group; fluorine atom, chlorine atom, bromine atom or the like for the halogen atom; fluoromethyl group, trifluoromethyl group or the like for the halo- lower alkyl group; acetoxy group, benzoyloxy group or the like for the acyloxy group; acetoxymethyl group, benzoyloxy-methyl group or the like for the acyloxy- lower alkyl group; a group exemplified above in $R^4$ or the like for the acyl group; carboxymethyl group, carboxyethyl group or the like for the carboxy- lower alkyl group; methoxycarbonylmethyl group, t-butoxycarbonylmetyl group or the like for the alkoxy-carbonyl- lower alkyl group; and methylthio group, ethylthio group or the like for the lower alkylthio group.

In the above-described, regarding the substituent of the substituted amino group and the substituted amino- lower alkyl group, for example, lower alkyl groups such as methyl group, ethyl group and the like, lower cyclo- alkyl groups such as cyclopropyl group, cyclobutyl group, cyclopentyl group and the like, lower alkenyl groups such as vinyl group, allyl group and the like, lower aralkyl groups such as benzyl group, 1-phenylethyl group and the like, aryl groups such as phenyl group and the like, acyl groups such as groups exemplified above in $R^2$ and the like, amino acid or peptide residues such as glycyl-, leucyl-, valyl-, alanyl-, phenylalanyl-, alanyl-alanyl-, glycyl-valyl and glycyl-glycyl-valyl- groups and the like, amino acid residues or peptide residues such as the above-described groups protected by a protecting group such as acyl group, aralkyl group or the like commonly used in the peptide chemistry, and cyclic amino groups are given. The same or different kinds of 1 to 2 substituents can be freely selected.

Relating to the compounds protected by such amino acid residues or peptide residues, improvement of the water-solubility is expected.

As preferable examples of the substituted amino group and the substituted amino- lower alkyl group, in particular, methylamino group, ethylamino group, dimethylamino group, methylaminomethyl group, ethylaminomethyl group, dimethylaminomethyl group, glycyl-amino group, leucyl-amino group, valyl-amino group, alanyl-amino group, alanyl-alanyl-amino group and the like are given.

In $R^{10}$ for instance there are given methyl group, ethyl group or the like for the lower alkyl group; cyclopropyl group, cyclobutyl group or the like for the cyclo-lower alkyl group; benzyl group, 1-pyenylethyl group or the like for the aralkyl group; vinyl group, allyl group or the like for the alkenyl group; formyl group, acetyl group, methoxy-carbonyl group or the like for the acyl group; and hydroxy-methyl group, hydroxyethyl group or the like for the hydroxy- lower alkyl group. More preferable examples of cyclic amino group are given by the following formulae;

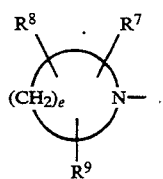
(a)

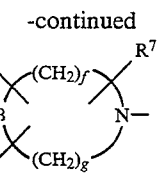
(b)

wherein B is one of an oxygen atom, a sulfur atom, —$NR^{10}$ and —$CONR^{10}$ wherein $R^{10}$ is one of a hydrogen atom, a hydroxyl group, a lower alkyl group, a cyclo- lower alkyl group, an aralkyl group, an alkenyl group, an acyl group and a hydroxy- lower alkyl group; wherein $R^7$, $R^8$ an $R^9$ are either same or different and are one of a hydrogen atom, a lower alkyl group, a lower alkenyl group, a lower aralkyl group, an aryl group, a hydroxyl group, a hydroxy- lower alkyl group, a substituted or unsubstituted amino group, a substituted or unsubstituted amino- lower alkyl group, a pyrrolidinyl group, a piperidino group, an azetidinyl group, an alkoxyl group an alkoxy- lower alkyl group, a halogen atom, a halo- lower alkyl group, an acyloxy group, an acyloxy- lower alkyl group, an acyl group, a carboxyl group, a carboxy- lower alkyl group, an alkoxycarbonyl-lower alkyl group, a mercapto group, a lower alkylthio group, a cyano group and a nitro group; wherein e is an integer of 3 to 5; wherein f is an integer of 1 to 3; and wherein g is an integer of 0, 1 and 2.

The cyclic amino group represented by the formulae (a) and (a') could be exemplified azetidinyl group, pyrrolidinyl group or piperidino group, and the cyclic amino group represented by the formulae (b) and (b') could be exemplified piperazinyl group, homopiperazinyl group, morpholino group, thiomorpholino group, 2,5-diazabicyclo[2.2.1]heptan-2-yl group, 3,8-diazabicyclo[3.2.1]octan-8-yl group and the like.

Further preferable examples of groups represented by formulae (a), (a'), (b) and (b') are as follows:

3-hydroxyazetidinyl group, 3-aminoazetidinyl group, 3-(N-t-butoxycarbonylamino)azetidinyl group, 3-acetylaminoazetidinyl group, 3-methylaminoazetidinyl group, 3-dimethylaminoazetidinyl group, 3-methylazetidinyl group, 3-amino-2-methylazetidinyl group; pyrrolidinyl group, 3-hydroxypyrrolidinyl group, 3,4-dihydroxypyrrolidinyl group, 3-methoxypyrrolidinyl group, 3-methylpyrrolidinyl group, 3-hydroxy-4-methyl-pyrrolidinyl group, 3-aminopyrrolidinyl group, 3-methylaminopyrrolidinyl group, 3-dimethylaminopyrrolidinyl group, 3-acetylamino-pyrrolidinyl group, 3-t-butoxycarbonylaminopyrrolidinyl group, 3-(N-acetyl)methylaminopyrrolidinyl group, 3-(t-butoxycarbonyl)methylaminopyrrolidinyl group, 3-aminomethylpyrrolidinyl group, 3-methylaminomethylpyrrolidinyl group, 3-dimethylaminomethylpyrrolidinyl group; 3-ethylaminomethylpyrrolidinyl group, 3-diethylaminomethylpyrrolidinyl group, 3-(N-acetyl)aminomethylpyrrolidinyl group, 3-(t-butoxycarbonyl)aminomethylpyrrolidinyl group, 3-(N-acetyl)methylaminomethylpyrrolidinyl group, 3-(t-butoxycarbonyl)methylaminomethylpyrrolidinyl group, 3-(1-aminoethyl)pyrrolidinyl group, 3-(2-aminoethyl)pyrrolidinyl group, 3- (1-amino-1-methylethyl)pyrrolidinyl group, 3- (1methylaminoethyl)pyrrolidinyl group, 3-(1-dimethylaminoethyl)pyrrolidinyl group; 3-amino-4-methylpyrrolidinyl group, 3-amino-5-methylpyrrolidinyl group, 3-methylamino-4-methylpyrrolidinyl group, 3-dimethylamino-4-methylpyrrolidinyl group, 3- ethylamino-4-methylpyrrolidinyl group, 3-diethylamino-3-methylpyrrolidinyl group, 3-diethylamino-4-methylpyrrolidinyl group, 3-aminomethyl-4-methylpyrrolidinyl group, 3-methylaminomethyl-4-methylpyrrolidinyl group, 3-dimethylaminomethyl-4-methylpyrrolidinyl group, 3-ethylaminomethyl-4-methylpyrrolidinyl group, 3-(1-aminoethyl)-4-methylpyrrolidinyl group, 3-(2-aminoethyl)-4-methylpyrrolidinyl group, 3-amino-4-ethylpyrrolidinyl group, 3-methylamino-4-ethylpyrrolidinyl group, 3-dimethylamino-4-ethylpyrrolidinyl group, 3-ethylamino-4-ethylpyrrolidinyl group, 3-diethylamino-4-ethylpyrrolidinyl group, 3-aminomethyl-4-ethylpyrrolidinyl group, 3-dimethylaminomethyl-4-ethylpyrrolidinyl group; 3-amino-3-methylpyrrolidinyl group, 3-methylamino-3-methylpyrrolidinyl group, 3-dimethylamino-3-methylpyrrolidinyl group, 3-amino-3,4-dimethylpyrrolidinyl group, 3-amino-4,4-dimethylpyrrolidinyl group, 3-amino-4,5-dimethylpyrrolidinyl group, 3-amino-2,4-dimethylpyrrolidinyl group, 3-methylamino-3,4-dimethylpyrrolidinyl group; 2-methyl-3-aminopyrrolidinyl group, 2-methyl-3-dimethylaminopyrrolidinyl group, 3-amino-4-vinylpyrrolidinyl group, 3-amino-4-methoxypyrrolidinyl group, 3-amino-4-methoxymethylpyrrolidinyl group, 3-methylamino-4-methoxypyrrolidinyl group, 3-dimethylamino-4-methoxypyrrolidinyl group, 3-ethylamino-4-methoxypyrrolidinyl group, 3-diethylamino-4-methoxypyrrolidinyl group; 3-benzylamino-4-methoxypyrrolidinyl group, 3-aminomethyl-4-methoxypyrrolidinyl group, 3-methylamino-4-methoxypyrrolidinyl group, 3-dimethylaminomethyl-4-methoxypyrrolidinyl group, 3-ethylaminomethyl-4-methoxypyrrolidinyl group, 3-aminomethyl-3-methoxypyrrolidinyl group, 3-methylaminomethyl-3-methoxypyrrolidinyl group, 3-dimethylaminomethyl-3-methoxypyrrolidinyl group, 3-amino-4-ethoxypyrrolidinyl group, 3-methylamino-4-ethoxypyrrolidinyl group, 3-dimethylamino-4-ethoxypyrrolidinyl group, 3-methylamino-4-ethoxypyrrolidinyl group, 3-aminomethyl-4-ethoxypyrrolidinyl group, 3-dimethylaminomethyl-4-ethoxypyrrolidinyl group, 3-amino-4-carbamoylpyrrolidinyl group, 3-amino-4-dimethylcarbamoylpyrrolidinyl group, 3-amino-4-hydroxypyrrolidinyl group, 3-amino-4-hydroxymethylpyrrolidinyl group, 3-amino-4-hydroxyethylpyrrolidinyl group; 3-amino-4-methyl-4-hydroxymethylpyrrolidinyl group, 3-aminomethyl-4-hydroxypyrrolidinyl group, 3-dimethylaminomethyl-4-hydroxypyrrolidinyl group, 3,4-dihydroxypyrrolidinyl group, 3,4-dimethoxypyrrolidinyl group, 3-hydroxy-4-methylpyrrolidinyl group, 3-amino-4-fluoropyrrolidinyl group, 3-amino-4-fluoromethylpyrrolidinyl group, 3-amino-4-trifluoromethylpyrrolidinyl group, 3-methylamino-4-fluoropyrrolidinyl group, 3-dimethylamino-4-fluoropyrrolidinyl group, 3-aminomethyl-4-fluoropyrrolidinyl group, 3-methylaminomethyl-4-fluoropyrrolidinyl group, 3-dimethylaminomethyl-4-fluoropyrrolidinyl group; 3-methylamino-4-chloropyrrolidinyl group, 3-aminomethyl-4-chloropyrrolidinyl group, 3-methyl, aminomethyl-4-chloropyrrolidinyl group, 3-(2-hydroxyethyl)aminomethylpyrrolidinyl group, 3-(2-fluoroethyl)aminomethylpyrrolidinyl group, 3-amino-4-methylthiopyrrolidinyl group, 3-amino-4-methylsulfonylpyrrolidinyl group, 3-formimidoylaminopyrrolidinyl group, 3-(2-dimethylhydrazino)pyrrolidinyl group, 3-amino-4-methylenepyrrolidinyl group, 3-(t-butoxycarbonylaminoacetyl)amino-4-methylpyrrolidinyl group, 3-aminoacetylamino-4-methylpyrrolidinyl group, 3-(2-aminopropanoyl)amino-4-methylpyrrolidinyl group, 3-(2-amino-3-phenylpropanoyl)amino-4-methylpyrrolidinyl group, 3-(2-benzyloxycarbonyl)amino-3-methylbutanoyl-4-methylpyrrolidinyl group, 3-(2-amino-3-methylbutanoyl)amino-4-methylpyrrolidinyl group, 3-(2-amino-2-methylpropanoyl)amino-4-methylpyrrolidinyl group, 7-amino-5-azaspiro[2,4]heptan-5-yl group; piperazinyl group, 4-methylpiperazinyl group, 3-methylpiperazinyl group, 2-methylpiperazinyl group, 3,4-dimethylpiperazinyl group, 3,5-dimethylpiperazinyl group, 3,8-dimethylpiperazinyl group, 3,4,5-trimethylpiperazinyl group, 4-ethoxycarbonylpiperazinyl group, 4-t-butoxycarbonylpiperazinyl group, 4-acetylpiperazinyl group, 4-benzyloxycarbonylpiperazinyl group, 4-ethylpiperazinyl group, 3,4-diethylpiperazinyl group, 3,4,5-triethylpiperazinyl group, 4-ethyl-3,5-dimethylpiperazinyl group, 3-methyl-4-acetylpiperazinyl group, 3-methyl-4-t-butoxycarbonylpiperazinyl group, 4-benzylpiperazinyl group, 4-n-propylpiperazinyl group; 4-isopropylpiperazinyl group, 4-t-butylpiperazinyl group, 4-cyclopropylpiperazinyl group, 4-cyclopentylpiperazinyl group, 4-cyclopropylmethylpiperazinyl group, 4-phenylpiperazinyl group, 4-(p-dimethylaminophenyl)piperazinyl group, 4-(p-methoxyphenyl)piperazinyl group, 4-(p-fluorophenyl)piperazinyl group, 3-phenylpiperazinyl group, 3-(p-fluorophenyl)piperazinyl group, 3-(p-chlorophenyl)piperazinyl group, 3-(p-hydroxyphenyl)piperazinyl group, 3-(p-methylphenyl)piperazinyl group, 4-hydroxyethylpiperazinyl group; 4-aminoethylpiperazinyl group, 4-allylpiperazinyl group, 4-cinnamylpiperazinyl group, 4-cyanoethylpiperazinyl group, 4-carboxyethylpiperazinyl group, 4-carboxymethylpiperazinyl group, 4-(1,2-dicarboxyethyl)piperazinyl group, 4-hydroxypiperazinyl group, 3-fluoromethyl-.piperazinyl group, 3-trifluoromethylpiperazinyl group, 4-formimidoylpiperazinyl group, 4-acetoimidoylpiperazinyl group; piperidino group, 4-aminopiperidino group, 4-dimethylaminopiperidino group, 4-hydroxypiperidino group, morpholino group, 2-aminomethylmorpholino group, 2-methylaminomorpholino group, 2-dimethylaminomorpholino group, thiomorpholino group, homopiperazinyl group, 4-methylhomopiperazinyl group, thiazolidinyl group, and oxazolidinyl group.

In case that Y is the group represented by the formula $R^5—(CH_2)m—A—$, as regards substituents capable of substituting this group in which $R^5$ is an amino group, a saturated heterocyclic group having a nitrogen atom or a lower cycloalkyl group, the same groups as those capable of substituting the substituted or unsubstituted cyclic amino group described above can be given. Further, as to the lower cycloalkyl group, cyclopropyl group, cyclobutyl group and the like are given. Regarding the saturated heterocyclic group having a nitrogen atom, a 4 to 9 membered ring is preferable, and the same saturated heterocyclic groups as those exemplified for the above-described cyclic amino groups can be given. For instance, azetidin-3-yl group, pyrrolidin-3-yl group and the like are particularly preferable. Also, the connection between these saturated heterocyclic group and a group of $—(CH_2)m—A—$ can be carried out on any atom of the ring.

In case that Y is the group represented by the formula $R^6—SO_2O—$, in $R^6$ there are given methyl group, ethyl group or the like for the lower alkyl group, fluoromethyl group, trifluoromethyl group or the like for the halo- lower alkyl group, and para-methylphenyl group or the like for the phenyl group mono-, di- or tri-substituted with a lower alkyl group. Further, as preferable examples of the group represented by $R^6$—$SO_2O$—, methanesulfonyloxy group, trifluoromethanesulfonyloxy group, para-toluene-sulfonyloxy group and the like are given.

As to the substituted or unsubstituted lower alkyl group represented by Y, in addition to the lower alkyl groups such as methyl group, ethyl group and the like, mono- or di-substituted, lower alkyl groups substituted by a carboxyl group, alkoxycarbonyl group, cyano group and the like are given, and preferably carboxymethyl group, ethoxycarbonyl-(cyano)methyl group, t-butoxycarbonyl(cyano)methyl group and the like are given.

As to the substituted or unsubstituted cyclo-lower alkenyl group represented by Y, oxo-cyclohexenyl group, oxocyclopentenyl group and the like are given, and preferably 3-oxo-1-cyclopentenyl group, 3-oxo-1-cyclohexenyl group and the like are given.

Further, according to the present invention, the compound represented by general formula (1) can be formed by both an salt with acid and a salt with base, and these salts can include those forming a chelate salt with boron compound. As regards the salt with acid for example, (a) salts with a mineral acid such as hydrochloric acid, sulfuric acid or the like, (b) salts with an organic carboxylic acid such as formic acid, citric acid, trichloroacetic acid, trifluoroacetic acid, fumaric acid, maleic acid or the like, and (c) salts with a sulfonic acid such as methanesulfonic acid, benzene-sulfonic acid, p-toluenesulfonic acid, mesitylenesulfonic acid, naphthalenesulfonic acid or the like can be given. Further, as to the salt with base, for instance, (a) salts with an alkali metal such as sodium, potassium or the like, (b) salts with an alkaline earth metal such as calcium, magnesium or the like, (c) ammonium salt, and (d) salts with an organic base having a nitrogen atom such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-ephenamine, N,N'-dibenzylethylenediamine or the like can be given.

Further, as examples of boron compound, for instance, boron halide such as boron fluoride and the like, lower acyloxy boron such as acetoxy boron and the like. According to the present invention, the compound represented by general formula (1) exists not only in an unsolvated form but also in a hydrate or solvated form and hence includes a crystal type, a hydrate type and a solvated type.

Also, the compound represented by general formula (1) can include an asymmetric carbon atom and thus exists in the form of optically active substances. Of course, these optically active substances can be included in the compound of the present invention. Further, the compound represented by general formula (1) can include at least two asymmetric carbon atoms and exist in the form of other stereo-isomers such as cis or trans forms. Of course, these stereoisomers can be included in the compound of the present invention.

The compound represented by general formula (1) can be prepared by suitable certain methods. The preferable preparation methods are exemplified as follows.

Process 1

The compound is represented by general formula (1), wherein $R^1$ is a hydrogen atom or a lower alkyl group and Y is a halogen atom or a group represented by a formula $R^6$—$SO_2O$— wherein $R^6$ is a lower alkyl group, a halo- lower alkyl group, a phenyl group or a mono-, di- or tri-substituted phenyl group by a lower alkyl group, and this compound will be produced by a series of steps shown by reaction scheme (1) as follows:

Reaction scheme (1):

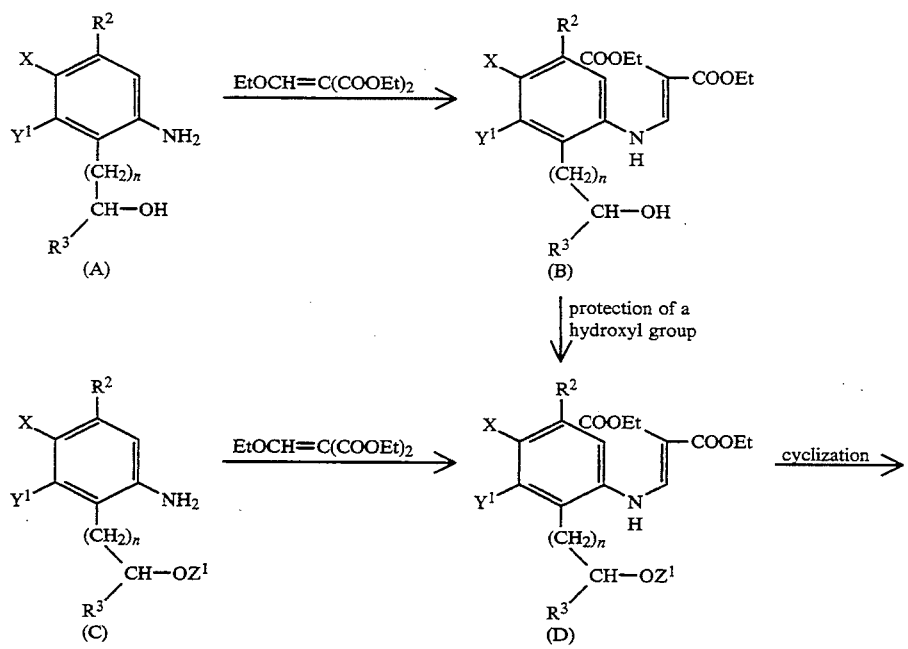

Reaction scheme (1):

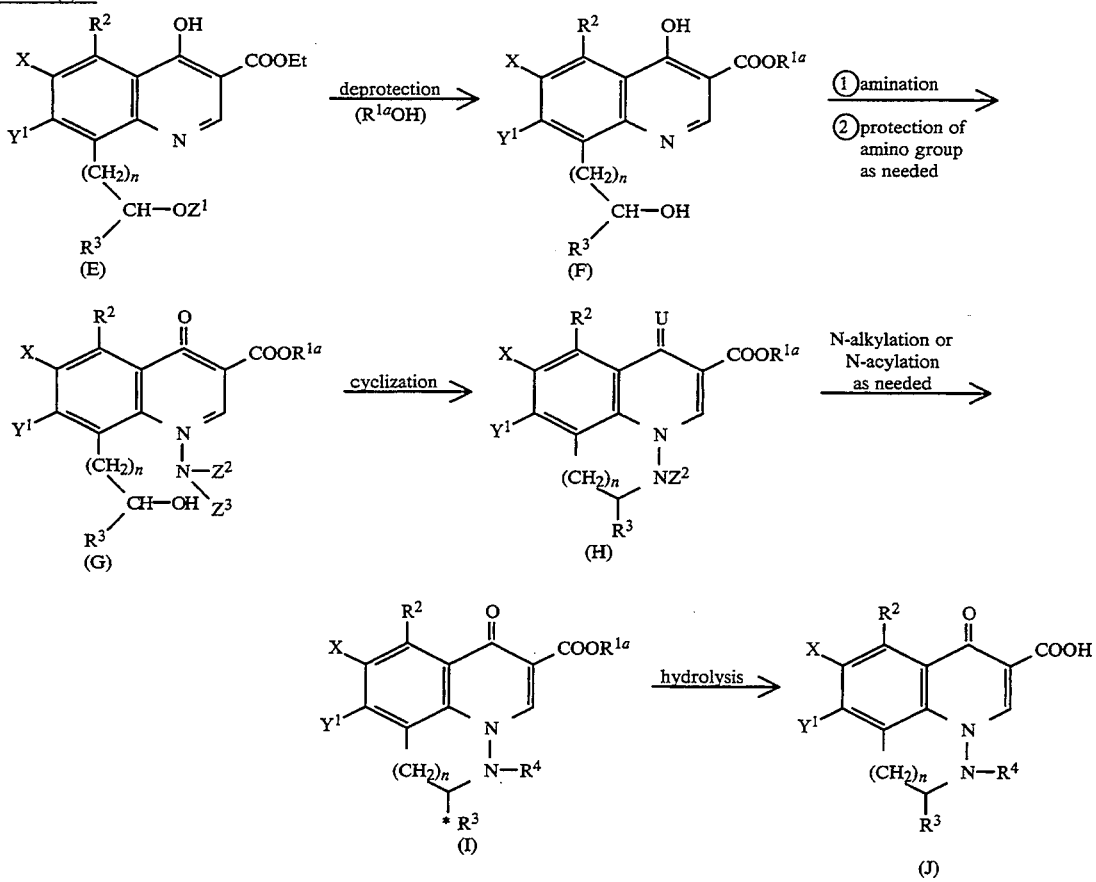

In the above formula, $Y^1$ is a halogen atom or a group represented by a formula $R^6$—$SO_2O$— wherein $R^6$ is a lower alkyl group, a halo- lower alkyl group, a phenyl group or a mono-, di- or tri-substituted phenyl group by a lower alkyl group, $Z^1$ is a hydroxy protecting group, $Z^2$ and $Z^3$ are either same or different and are one of a hydrogen atom, a lower alkyl group, an acyl group and an amino protecting group; $R^{1a}$ is a lower alkyl group and $R^2$, $R^3$, $R^4$, X and n are the same as described above.

In this process, a starting material is an o-hydroxyalkyl-aniline derivative or o-(acyloxyalkyl)aniline derivative represented by general formula (A) or (C). In this case, regarding a protecting group for a hydroxyl group represented by $Z^1$, any group usually used in protecting a hydroxyl group can be employed, for example, acyl group, trialkylsilyl group, benzyl group, tetrahydropyranyl group and the like are given. Preferable examples of the acyl group include acetyl group, propionyl group, benzoyl group and pivaloyl group. Preferable examples of the trialkylsilyl group include t-butyldimethylsilyl group, triethyl, silyl group and t-butyldiphenylsilyl group.

In this process, firstly, compound (A) or compound (C) is reacted with diethyl ethoxymethylene malonate to obtain compound (B) or compound (D), respectively. This reaction can be carried out at reaction temperatures of 80° to 150° C. without using any solvent but can be performed using a solvent having no activated hydrogen such as toluene, xylene or the like.

Compound (B) is converted into compound (D) by protecting a hydroxyl group. In case that the protecting group is an acyl group, this reaction can be carried out by any reaction usually used for acylation of hydroxyl group. For instance, acylchloride corresponding to $Z^1$ and compound (B) are reacted with each other in a solvent having no activated hydrogen such as dichloromethane, ether or acetone at a temperature of 0° C. to room temperature in the presence or absence of a base such as pyridine, triethylamine, sodium carbonate or potassium carbonate.

In this case, regarding the acyl group represented by $Z^1$, any group usually used in protecting a hydroxyl group for example, acetyl group, propionyl group, benzoyl group and the like can be used.

In case that the protecting group is a trialkylsilyl group, this reaction can be carried out by any reaction usually used for trialkylsilylation of hydroxyl group. For instance, trialkylsilylhalide corresponding to $Z^1$ and compound (B) are reacted with each other in a solvent having no activated hydrogen such as dichloromethane, N,N-dimethylformamide or acetone at temperatures of 0° to 60° C. in the presence of a base such as imidazole, triethylamine or 2,6-lutidine.

Compound (D) is cyclized to obtain compound (E). This reaction can be carried out by a variety of methods. For example, compound (D) is heated in an inert solvent such as diphenyl ether or dibenzyl ether at temperatures of 180° to 270° C. or in polyphosphoric acid at temperatures of 100° to 160° C.

Compound (E) is converted into compound (F) by eliminating the protecting group of hydroxyl group. In case that the protecting group is an acyl group, compound (E) is converted into compound (F) by alcoholysis. In this reaction, by using, as a solvent, an alcohol corresponding to $R^{1a}$ to be substituted to a carboxylic acid of compound (F) together with benzene, toluene, N,N-dimethylformamide, dimethylsulfoxide or N-methylpyrrolidone or without using any solvent except the alcohol, and using a catalytic amount of sodium hydroxide, potassium hydroxide, sodium methylate, sodium ethylate or a base such as a metal alcoholate corresponding to $R^{1a}$, compound (E) is reacted at room temperature to a temperature of 100° C.

In case that the protecting group is a trialkylsilyl group, compound (E) is converted into compound (F) by acidic hydrolysis. In this reaction, by using tetrahydrofuran, alcohol, ether and the like, together with an acid such as acetic acid, hydrochloric acid, p-toluensulfonic acid and the like in the presence or absence of water. Compound(E) is converted into compound (F) by fluoride-assisted reaction by using tetrahydrofuran, together with tetra-n-butylammonium fluorides compound (E) is reacted at a temperature of 0° C. to room temperature.

Compound (F) is reacted with an aminating agent such as mesitylenesulfonylhydroxyamine, o-(2,4-dinitrophenyl)hydroxylamine or the like to obtain compound (G). This reaction is carried out in the presence of a base such as sodium carbonate, potassium carbonate or the like in a solvent such as N,N-dimethylformamide, N-methylpyrrolidone or the like at a temperature of 0° to 60° C.

Compound (G) is cyclized to obtain compound (H). This cyclization reaction is carried out by a variety of methods. For instance, compound (G) is reacted with triphenylphosphine and diethyl azodicarboxylate in a solvent such as tetrahydrofuran at a temperature of 0° to 60 ° C.

Further, this cyclization reaction could be carried out after substitution on the amino group by a lower alkyl group and an amino-protection group such as $Z^2$ or $Z^3$, if desired. Wherein, lower alkyl group could be methyl, ethyl and so on, and amino-protecting group could be the exemplified ones for protection of $R^2$.

Compound (H) is alkylated or acylated to obtain compound (I), if desired. The alkylation is carried out by reacting compound (H) with an alkylating agent such as dialkylsulfate, alkyl iodide, alkyl bromide or the like corresponding to the desired alkyl group in a solvent such as N,N-dimethylformamide, N-methylpyrrolidone or the like at room temperature to a temperature of 150° C. preferably in the presence of a base such as sodium carbonate, potassium carbonate or the like.

The acylation can be carried out by any conventional method. For instance, acylchloride corresponding to the desired acyl group is reacted with compound (H) in a solvent such as dichloromethane, ether or acetone at a temperature of 0° C. to room temperature in the presence or absence of base such as pyridine, triethylamine, sodium carbonate, potassium carbonate or the like; and acid such as formic acid, acetic acid or the like, or acid anhydride from them are reacted with compound (H) at room temperature to 120° C.

Compound (I) is hydrolized to obtain compound (J). This reaction is carried out by using a known reaction. For instance, compound (I) can be reacted in an aqueous alkaline solution such as aqueous sodium hydroxide solution, aqueous potassium hydroxide solution or aqueous sodium carbonate solution, or in an aqueous acidic solution such as hydrochloric acid or acetic acid at room temperature to a temperature of 100° C. by using a solvent mixible with water such as ethanol, methanol, tetrahydrofuran, N,N-dimethylformamide, dimethylsulfoxide or the like or without using any solvent.

Process 2

The compound is represented by general formula (1), wherein $R^1$ is hydrogen atom or a lower alkyl group, Y is an amino group, hydroxyl group, a cyclo- lower alkylamino group, a mono- or di- lower alkylamino group, a substituted or unsubstituted cyclic amino group, a substituted or unsubstituted lower alkyl group and a substituted or unsubstituted cyclo- lower alkenyl group, a group represented by a formula $R^5$—$(CH_2)_m$—A— wherein $R^5$ is a hydrogen atom, a substituted or unsubstituted amino group, a substituted or unsubstituted saturated heterocyclic group having a nitrogen atom or a substituted or unsubstituted lower cyclo-alkyl group, A is an oxygen atom or sulfur atom, and m is an integer of 0 to 3. This compound will be prepared in the process shown by reaction scheme (2):

Reaction scheme (2):

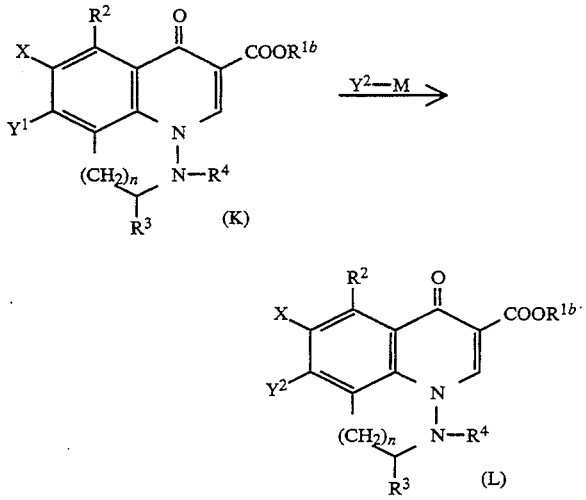

In this scheme, $R^{1b}$ is a hydrogen atom or a lower alkyl group, $Y^2$ is an amino group, a cyclo- lower alkylamino group, a mono- or di- lower alkylamino group, a substituted or unsubstituted cyclic amino group, a substituted or unsubstituted lower alkyl group and a substituted or unsubstituted cyclo- lower alkenyl group or a group represented by a formula $R^5$—$(CH_2)m$—A— wherein $R^5$ is a hydrogen atom, a substituted or unsubstituted amino group, a substituted or unsubstituted saturated heterocyclic group having nitrogen atom or a substituted or unsubstituted lower cyclo-alkyl group, A is an oxygen atom or sulfur atom, and m is an integer of 0 to 3, and wherein M is a hydrogen atom, an alkali metal atom or an organo- metallic compound with the proviso that M is an organo- metallic compound when $Y^2$ is a substituted or unsubstituted cyclo-lower alkenyl group, and $R^2$, $R^3$, $R^4$, X, $Y^1$ and n are the same as described above.

That is, the compound is obtained by reacting compound (K) obtained in process 1 with a compound represented by a formula $Y^2$—M or its salt or an alkali metal alcoholate.

This reaction is preferably carried out in an inert reaction solvent such as acetonitrile, N,N-dimethylformamide, dimethylsulfoxide, sulfolane, N-methylpyrrolidone or the like or a mixture thereof. Further, this reaction can be carried out in the form of a chelate compound of (K) resulted from a reaction of boron trifluoride or its solvated complex or tris(lower acyloxy) borane in an inert solvent. The reaction temperature is preferably 50° to 200° C., and 80° to 150° C. is more preferable. This reaction is preferably carried out in the presence of a base such as triethylamine, 2,6-lutidine, 1,8-diazabicyclo[5.4.0]undec-7-ene, 1,5-diazabicyclo[4.3.0]non-5-ene, an alkali metal carbonate or the like for neutralizing a hydrogen halide which is produced in this reaction. It can also be neutralized by using an excess amount of an alkali metal alcoholate or amine. In case that $Y^2$ is a substituted or unsubstituted cyclo-lower alkenyl group, M represents an organometallic compound which is, preferably, trialkyl tin, such as tributyl tin.

This reaction could be preferably carried out using palladium catalyst such as tetrakis (triphenyl phosphine) palladium, bis(acetonitrile)palladium (II) chloride, bis(-triphenylphosphine)palladium (II) chloride and so on. In this reaction, although a product may be obtained in a salt form, if necessary, the product can be treated by an acid such as acetic acid, trifluoroacetic acid, hydrochloric acid or the like or a base such as sodium carbonate, potassium carbonate, sodium hydroxide, potassium hydroxide or the like to convert into a free form.

In this reaction, when there are substituents such as hydroxyl group, mercapto group, carboxyl group and amino group in the compound represented by $Y^2$—M, there are some cases where the yield of the compound (L) in the above reaction is remarkably dropped. In such a case, after hydroxyl group, mercapto group, carboxyl group and amino group in the compound represented by $Y^2$—M are protected appropriately, the reaction is carried out in the process of reaction scheme (2), and then the elimination of the protecting groups in the obtained compound is carried out to bring about a excellent yield. In this case, any known protecting groups can be used, for example, acyl group, alkoxycarbonyl group or benzyl group for hydroxyl group acyl group or ethylthio group for mercapto group, benzyl group for carboxyl group; and acyl group, alkoxycarbonyl group, benzyl group or the like for amino group. These protecting groups can be removed by a proper known method such as acidic hydrolysis, basic hydrolysis, catalytic hydrogenation or the like.

Process 3

The compound represented by the general formula (1), wherein $R^1$ is a carboxyl protecting group, is produced in the process shown by reaction scheme (3):

Reaction scheme (3):

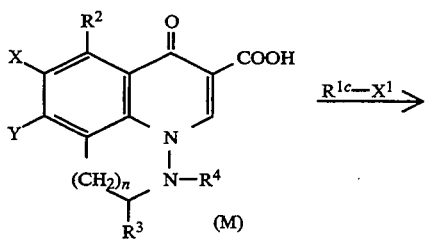

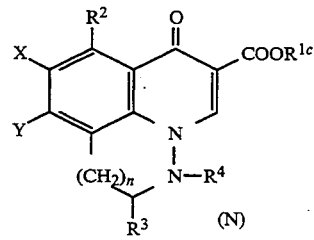

In this scheme, $R^{1c}$ is a carboxyl protecting group, $X^1$ is a hydroxyl group or a halogen atom, and $R^2$, $R^3$, $R^4$ X, Y and n are the same as described above.

That is, compound (M) is reacted with a halide represented by $R^{1c}$—$X^1$ to obtain compound (N).

This reaction is preferably carried out at room temperature to a temperature of 100° C. in the presence of bases such as triethylamine, trimethylamine, sodium hydroxide, potassium hydroxide, potassium carbonate, and the like by using an inert solvent such as N,N-dimethylformamide, dimethylsulfoxide, N-methylpyrrolidone or the like. In this process, there are also some cases; where the yield of the compound is dropped due to substituents of Y like process 2, but this problem can be solved in the same manner as described in process 2.

Although a producing method of a new tricyclic compound represented by general formula (1) has herein been explained with reference to processes 1 to 3, the producing method of the compound according to the present invention is not restricted to these methods.

For example, a compound represented by general formula (1), wherein $R^3$ is a hydrogen atom and $n=1$, can be also prepared in processes 4 to 7 shown by reaction scheme (4):

Reaction scheme (4):

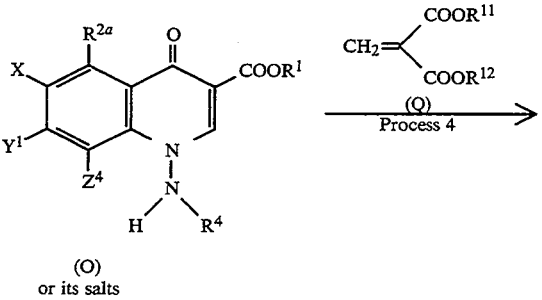

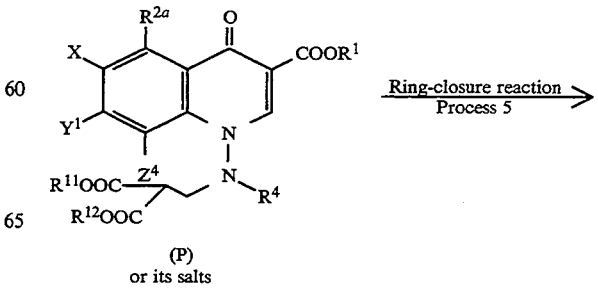

Reaction scheme (4):

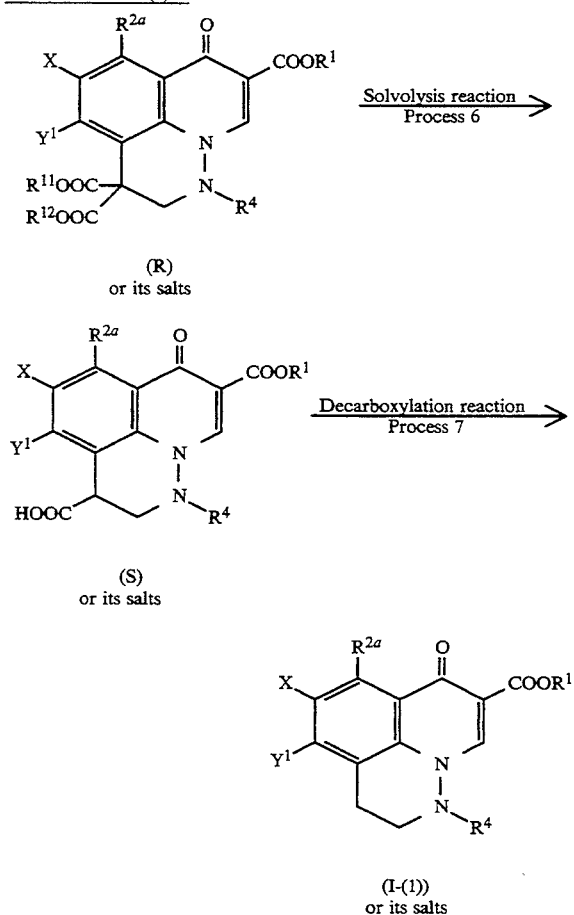

In this formula, $R^{2a}$ is a hydrogen atom or a halogen atom $R^{11}$ and $R^{12}$ are a hydrogen atom or a carboxyl protecting group, $Z^4$ is a leaving group, and $R^4$, X and $Y^1$ are the same as described above.

Process 4

Compound (P) or its salts can be prepared by the Michael addition reaction of compound (O) or its salts with a compound (Q) having a conjugated double bond.

As examples of preferable salts of compound (O) and compound (P), refer to the examples of the compound represented by formula (1).

This reaction usually proceeds in the presence of a base or a Lewis acid. Preferable bases, include alkali metal hydrides such as sodium hydride, potassium hydride and the like, alkaline earth metal hydrides such as calcium hydride and the like, alkali metal alkoxides such as pottasium t-butoxide and the like, and potassium fluoride and the like. As examples of a preferable Lewis acid, zinc halides such as zinc bromide, zinc chloride and the like, magnesium halides such as magnesium bromide, magnesium chloride and the like, titanium compounds such as titanium tetrachloride, titanium tetraethoxide, titanium tetrapropoxide and the like, boron trifluoride and the like are given.

The reaction is usually carried out in a solvent, for example, water, alcohol such as methanol, ethanol or the like, methylene chloride, tetrahydrofuran, N,N-dimethylformamide, dimethylsulfoxide, N-methylpyrrolidone or the like, or a mixture thereof, and the reaction can be run in any solvent or mixed solvent as far as such a solvent or mixed solvent does not have any bad influence on the reaction.

As examples of an adjuvant on using the solvent or activity of a Lewis acid, a compound having an ether bonding modifying the activity of Lewis acid, for example, diethyl ether, 1,2-epoxypropane, tetra-hydrofuran, dioxane or the like can be used.

The reaction temperature is not limited in particular, but the reaction is usually carried out under heating.

Process 5

Compound (R) or its salts can be made by ring-closure reaction of compound (P) or its salt.

As examples of a preferable salt of compound (R), refer to the examples of the compound represented by formula (1).

As to the leaving group represented by $Z^4$, for example, halogen atoms such as fluorine or the like are given.

The ring-closure reaction is usually carried out in the presence of a base in a solvent. As examples of preferable base and solvent, refer to the examples shown in process 4.

The reaction temperature is not limited in particular, but the reaction is usually carried out under heating.

Depending on the reaction condition such as using dimethylsulfoxide, the ring-closure reaction in process 5 continuously occurs after the Michael additon reaction in process 4, and the reactions collectively carried out in one pot.

Process 6

Compound (S) or its salts can be formed by a solvolysis reaction of compound (R) or its salts.

As examples of a preferable salt of compound (S), refer to the examples of compound represented by formula (1).

The solvolysis reaction is preferably carried out in the presence of a base or an acid including Lewis acid. Regarding a preferable base, inorganic bases and organic bases, for example, alkali metals such as sodium, potassium and the like, alkaline earth metals or its hydroxides, carbonates or hydrogen carbonate such as magnesium, calcium and the like, trialkylamines such as trimethylamine, triethylamine and the like, picoline, 1,5-diazabicyclo[4.3.0]non-5-ene, 1,4-diazabicyclo[2.2.-2]octane, 1,8-diazabicyclo[5.4.0]undec-7-ene and the like are given.

Preferable acids include organic acids such as formic acid, acetic acid, glacial acetic acid, propionic acid, trichloroacetic acid, trifluoroacetic acid and the like, and inorganic acids such as hydrochloric acid, hydrobromic acid, sulfuric acid, hydrochloride, hydrobromide and the like.

The elimination using a Lewis acid typified by a trihaloacetic acid such as trichloroacetic acid, trifluoroacetic acid or the like is preferably carried out in the presence of a cation trapping agent such as anisole, phenol or the like.

The reaction is usually carried out in a solvent, for example, water, alcohol such as methanol, ethanol or the like, methylene chloride, tetrahydrofuran, N,N-dimetylformamide, dimethyl sulfoxide or the like, or a mixture thereof, and the reaction proceeds in any solvent or mixed solvent as far as such a solvent or mixed solvent does not have any bad influence to the reaction. A liquid base or acid can also be used as a solvent.

The reaction temperature is not restricted in particular, but the reaction is usually carried out under cooling or heating.

Process 7

Compound (I-(1)) or its salts can be formed by a decarboxylation reaction of compound (S) or its salts.

As examples of a preferable salt of compound (I-(1)), refer to the examples of the compound represented by formula (1).

This reaction is carried out by heating under an inert gas such as nitrogen or according to a normal method such as reduction.

The reaction is usually carried out in a solvent, for example, water, alcohol such as methanol, ethanol or the like, methylene chloride, tetrahydrofuran, N,N-dimetylformamide, dimethyl sulfoxide or the like, or a mixture thereof, and the reaction proceeds in any solvent or mixed solvent as far as such a solvent or mixed solvent does not have any bad influence on the reaction.

The reaction temperature is not restricted in particular, but the reaction is usually carried out under cooling or heating.

According to the method including above processes 4 to 7, compound (I-(1)) wherein $R^{2a}$ is a halogen atom can be effectively obtained, which will herein after be referred to as compound(I-(2)). This compound (I-(2)) can be readily modified to compound (I-(3)) having an amino group in processes 8 and 9 shown by reaction scheme (5):

Reaction scheme (5):

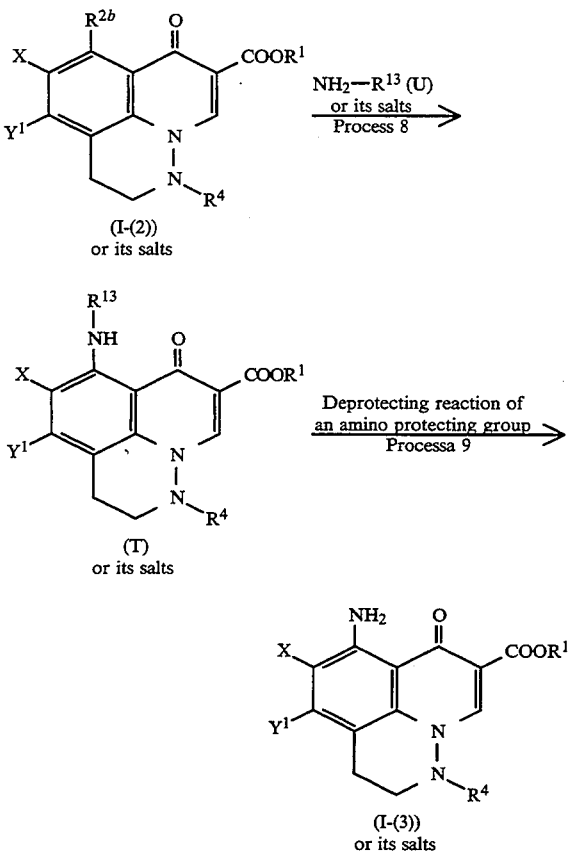

In this formula, $R^{2b}$ is a halogen atom, $R^{13}$ is an amino protecting group, and $R^4$, X and $Y^1$ are the same as described above.

Process 8

Compound (T) or its salts can be formed by reacting compound (I-(2)) or its salts with an amine compound (U) or its sales.

As examples of a preferable salt of compound (T), refer to the examples of the compound represented by formula (1).

Examples of the amino protecting group represented by $R^{13}$ are the same as those given for the protecting group in $R^2$. This reaction is generally carried out by using an equivalent or somewhat slightly excess amount of compound (U) or its salts to the annount of compound (I-(2)) or its salts in the presence of an acid acceptor such as sodium carbonate, calcium carbonate, sodium hydrogen carbonate, triethylamine, 1,8-diazabicyclo[5.4.0]undec-7-ene or the like, and an excess amount of compound (U) may be used as the acid acceptor.

The reaction is usually carried out in a solvent, for example, an aromatic hydrocarbon such as benzene, toluene, xylene or the like, an ether such as tetrahydrofuran, dioxane, monoglyme or the like, a halogenated hydrocarbon such as methylene chloride, chloroform or the like, dimethylformamide, dimethylsulfoxide, acetonitrile, pyridine or the like, and the reaction can be carried out in any solvent or mixed solvent as far as such a solvent or mixed solvent does not have any bad influence on the reaction.

The reaction temperature is not restricted in particular, but the reaction is usually carried out under heating.

Process 9

Compound (I-(3)) or its salts; can be formed by an deprotecting reaction of compound (T) or its salts to eliminate the amino protecting group thereof.

As examples of a preferable salt of compound (I-(3)), refer to the examples of the compound represented by formula (1).

For the deprotecting reaction of the amino protecting group, the usual reaction conditions for the hydrolysis or the catalytic reduciton can be applied.

More specifically, in case of the hydrolysis, the reaction is carried out in the presence of a basic compound such as sodium hydroxide, potassium hydroxide, barium hydroxide, potassium carbonate or the like, a mineral acid such as sulfuric acid, hydrochloric acid, nitric acid or the like, or an organic acid such as acetic acid, aromatic sulfonic acid or the like in a solvent, for example, water an alcohol such as methanol, ethanol, isopropanol or the like, a ketone such as acetone, methyl ethyl ketone or the like, an ether such as dioxane, ethyleneglycol, diethyl ether or the like, acetic acid or the like, or a mixture thereof. The reaction is usually carried out at room temperature to a temperature of 200° C., preferably room temperature to 120° C.

In case of the catalytic reduction, the reaction is usually carried out in the presence of a catalyst such as palladium on carbon, palladium black, platinum dioxide or the like in a solvent such as methanol, ethanol, propanol, acetic acid, tetrahydrofuran, dioxane, ethyl acetate, water or the like or a mixed solvent thereof at the atmospheric pressure to a pressure of 100 arm under hydrogen while stirring.

The reaction temperature is usually room temperature to 100° C. and is usually terminated in 1 to 48 hours.

In particular, in the group represented by Y, the substituents can be mutually converted by a variety of known methods. In process 2, although one example of the mutual conversion of the substituents is partly described as addition and elimination of the protecting groups, other reaction examples are described as follows. That is, a conversion from hydroxyl group to a halogen atom: an acylation of hydroxyl group, mercapto group, and primary and secondary amino groups; a conversion from a halogen atom to an amino or cyano group; a removal of alkoxycarbonyl group, benzyl group and acyl group; an alkylation of a carboxyl group, and primary and secondary amino groups; a conversion from an alkenyl group to alkyl group; and a cyclization by a connection of two groups.

A producing method of the compound of the starting material (A) or (C) wherein n=0 in process 1, for example, is disclosed in Japanese Patent Laid-open (Kokai) No. Hei 2-157282. Further, the compound of the starting material (A) or (C) wherein n=1 can be prepared by a process shown in reaction scheme (6) belows, and by a method described in "J. Heterocyclic. Chem., 25, 1567, 1988". More specifically, it can be prepared by the described method in a comparative example and equivalent methods thereof.

Reaction scheme (6):

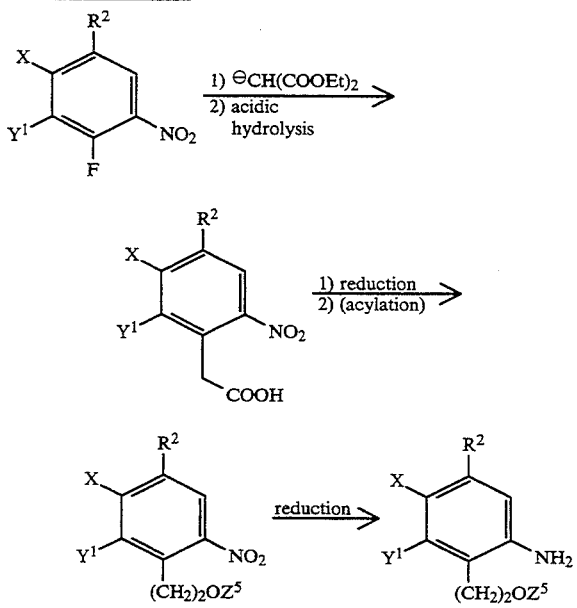

In this scheme, $Z^5$ is a hydrogen atom or an acyl group, and $R^2$, X and $Y^1$ are the same as described above.

As preferable examples of protection of $Z^5$, the same as described above with reference to $Z^1$ can be given.

The starting material (O) in process 4 can be prepared, for example, by reaction scheme (7):

Reaction scheme (7):

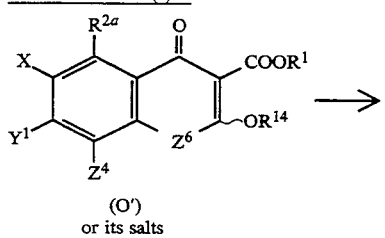

Reaction scheme (7):

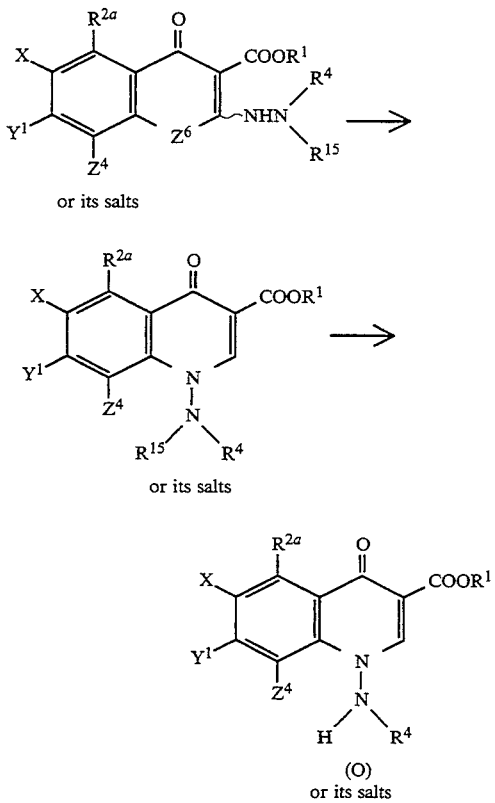

wherein $R^{14}$ is a lower alkyl group, $R^{15}$ is a protected amino group, $Z^6$ is a leaving group, and $R^1$, $R^{2a}$, $R^4$, X, $Y^1$ and $Z^4$ are as defined before. Here, examples of the protected amino group represented by $R^{15}$ are the same as those given for $R^{13}$, and the examples of $Z^6$ are the same as those given for $Z^4$.

Concerning reagents usable for synthesizing the starting material (O) and reaction conditions such as the selection of solvents and temperature, the following preparation examples may be referred to. The starting material (O') is described in Japanese Patent Laid-Open (Kokai) No. SHO 59-212474 (corresponding to U.S. Pat. No. 4,556,658).

Further the substituents appeared in processes (1) to (7), having no description of their definitions can be referred to the above description of the corresponding substituents in the compound represented by general formula (1).

The effects and advantages of the present invention will now be described in detail.

(1) Antimicrobial activity:

The minimum inhibitory concentration (MIC: μg/ml) of typical compounds represented by general formula (1) of the present invention is measured by the standard method of Japanese literature "Chemotherapy, Volume 29, No. 1, pp. 76–79, 1981". The results are shown in Table 1 in which compound numbers are the same as those indicated in Examples.

TABLE 1

| Compound No. | Minimum Inhibitory Concentration ($\mu$g/ml) | | |
|---|---|---|---|
| | E. coli NIH JC-2 (IFO* 12734) | S. aureus 209p (IFO 12732) | P. aeruginosa (IFO 3445) |
| 30 | 0.025 | 0.1 | 0.2 |
| 73 | 0.1 | 0.78 | 0.78 |

*Institute of Fermentation, Osaka (2) Absorption and excretion:

The absorbability and excretion after oral administration of the compounds, of the present invention were tested by measuring recovery in urine and in bile as follows.

(a) Recovery in urine:

To a group of three male JCL-SD rats (6 weeks old) fasted overnight, a subject compound was prepared to 20 mg/10 ml/kg with 0.5% of methylcellulose solution and was orally administrated. The sampling was carried out by collecting urine in 0 to 6 hours and 6 to 24 hours. The concentration of the subject compound in the urine was examined by a disk method by using Bacillus subtilis ATCC 33 as a testing bacillus to obtain an excretion rate in urine for 24 hours.

(b) Recovery in bile:

A subject compound was prepared in the same manner as the recovery in urine and was orally administrated to the rats and bile was collected by using a polyethylene tube inserted into the choledochus in 24 hours. The concentration of the subject compound in the bile sample was examined in the same manner as the recovery in urine to obtain an excretion rate in bile for 24 hours.

The results are shown in Table 2.

TABLE 2

| Compound No. | Excretion Rate (%, 24 hours) | |
|---|---|---|
| | In Urine | In Bile |
| 30 | 59.7 | 3.8 |

As described above, according to the present invention, the compounds represented by general formula (1) and salts thereof, which are novel compounds, exhibit an extremely excellent antimicrobial activity against gram-negative and gram-positive bacteria and possess a high oral absorbability. When the compounds represented by general formula (1) of the present invention are used as antimicrobial agents, the compounds can be treated as compositions together with pharmaceutical allowable carriers for parenteral dosage such as injection, per rectum, eye instillation and the like and oral dosage in the form of solid and solution.

Relating to the form of the composition for injections, pharmaceutical allowable axenic water or nonaqueous solution, suspension or emulsion, and the like are given. As examples of appropriate nonaqueous carrier, diluent, solution or vehicle, propylene glycol, polyethylene glycol and vegetable oils such as olive oil and injectable organic esters including, for example, oleic ester are given. These compositions can include supplementary agents such as antiseptics, wetting agents, emulsifiers, dispersants and the like. These compositions, for example, can be sterilized by filtering with a bacteria holding filter or mixing a sterilizer in the form of an axenic solid composition soluble in sterilized water or other several sterilizing injectable solutes or media right before the use.

The preparations for eye instillation dosage can preferably include dissolution adjuvants, preservatives, isotonic agents, mucilages and the like.

The solid preparations for oral dosage can include capsules, tablets, pills, powders and granules. In preparing the solid preparations, generally, the compound of the present invention is mixed with at least one kind of an inert diluent such as sucrose, lactose or starch. In a usual preparation, the preparations can further include a supplementary material except the inert diluent, for example, a lubricant such as magnesium stealate or the like. Further, the capsules, tablets and pills can further include a buffer. The tablets and pills can further apply an enteric coat thereon.

The solution preparations for oral dosage can include inert diluents usually used by a person skilled in the art, for instance, pharmaceutical allowable emulsifiers including water, solutions, suspensions, syrups and elixirs. In addition to such inert diluents, the compositions can be blended with supplementary agents such as wetting agents, emulsifiers, suspensions, edulcorants, flavors and perfumes.

The preparations for per rectum dosage can preferably include excipients such as cocoa butter or suppository wax in addition to the compound of the present invention.

According to the present invention, the dose of the compound represented by general formula (1) depends on properties of the compound to be dosed, dosing route, the desired treating period and other factors, and is, in general, approximately 0.1 to 1000 mg/kg a day, and preferably approximately 1 to 100 mg/kg a day. If necessary, this dose for one day can be separated into 2 to 4 times.

As described above, according to the present invention, the compounds represented by general formula (1) and salts thereof are extremely valuable as antimicrobials and can be used as not only pharmaceuticals or drugs for human body and animals but also drugs for fishes, agricultural chemicals and preservatives for foods. Further, the compounds of this invention are expected to inhibit the growth of virus especially HIV (human immuno deficiency virus) and the like.

EXAMPLES

Now, the present invention will be described in detail with reference to the exemplary embodiments, and it should be understood that these embodiments are given for only illustration of the invention and are not intended to be limitative therefor. Position numbers of two novel tricyclic compounds, represented by general formula (1) wherein n is 0 and 1, of the present invention for use in Reference Examples and inventive examples are exemplified as follows.

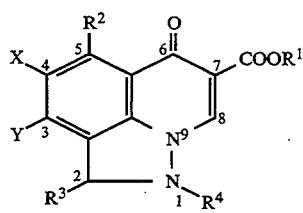

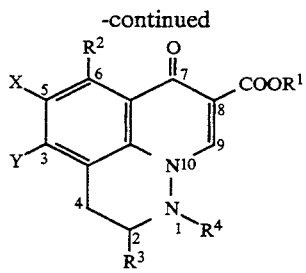

REFERENCE EXAMPLE 1

2,3-Difluoro-6-nitrophenylacetic acid (1)

64 g of 60% sodium hydride was added to 200 ml of tetrahydrofuran, and, while the mixed solution was stirred and cooled on ice, a solution obtained by dissolving 258 g of diethyl malonate in 400 ml of tetrahydrofuran was dropped to the mixed solution through 1 hour and 40 minutes so that the reaction temperature was kept below 20° C. Then, while the reaction solution was stirred and cooled on ice, 200 ml of tetrahydrofuran solution dissolving 142 g of 2,3,4-trifluoronitrobenzene was dropped to the reaction solution through 2 hours so that the reaction temperature was kept below 10° C. After reacting at room temperature for 2 hours, 100 ml of acetic acid was added to the reaction solution and tetrahydrofuran was removed by distillation. To the residue, 1 l of chloroform, 1.5 l of water and 100 ml of concentrated hydrochloric acid were added, and the solution was separated. The organic layer was separated from the solution, and the solvent was removed by distillation. To the residue, 250 ml of 4N hydrochloric acid and 200 ml of acetic acid were added, and the solution was heated under reflux for 11 hours. After removing 150 ml of content solution by distillation, 50 ml of acetic acid and 50 ml of water were added to the solution, and the solution was heated under reflux for 31 hours. After the solution was air-cooled, the precipitated crystal was filtered off, washed with diisopropyl ether and was dissolved in 400 ml of methanol. After treating with active carbon, the solvent was removed by distillation. The precipitated crystal was dispersed in diisopropyl ether and was filtered off to obtain 100 g of the subject compound (1) in a 56% yield.

REFERENCE EXAMPLE 2

Diethyl {2-(2-Acetoxyethyl)-3,4-difluoroanilino}methylene malonate (2)

19.8 g of the sodium borohydride was added to 60 ml of tetrahydrofuran, and, while the mixed solution was cooled on ice below 10° C., a solution obtained by dissolving 60 g (276 mmol) of 2,3-difluoro-6-nitrophenylacetic acid in 20 ml of tetrahydrofuran was dropped to the mixed solution through 1 hour. Then, 120 ml of tetrahydrofuran solution dissolving 90 ml of boron trifluoride ethyl ether complex was dropped to the reaction solution through 1 hour below 10° C. The solution was stirred for 15 minutes under cooled on ice and for 20 minutes at room temperature. To 1.5 l of methylene chloride, 1.2 l of ice/water, 84 g of sodium hydrogen carbonate was added, and, while well stirring this solution, the reaction solution was slowly added to this solution. The obtained solution was stirred overnight. The organic layer was separated from the solution, and after drying over magnesium sulfate, solvent was removed by distillation to obtain 61 g of oily 3,4-difluoro-2-(2-hydroxyethyl)nitrobenzene. To this oily material, 58 ml (414 mmol) of triethylamine and 500 ml of methylene chloride were added, and while cooling on ice, 100 ml of methylene chloride solution containing 19 ml (381 mmol) of acetyl chloride was dropped to the solution. After stirring for 1 hour and 80 minutes, 5 ml of acetyl chloride was further added to the mixture, and after 30 minutes, the mixture was washed with 200 ml of water twice. After drying over magnesium sulfate, the solvent was removed by distillation to obtain 76.5 g of 2-(2-acetoxyethyl)-3,4-difluoronitrobenzene.

43 g of iron powder and 4 ml of concentrated hydrochloric acid were added to 450 ml of water and 100 ml of ethanol. The solution was heated at 80° C., and, while well stirring, the obtained nitro compound was dropped to the solution through 30 minutes. The solution was stirred for 1 hour. After the solution was air-cooled, 500 ml of ethyl acetate was added to the filtrate, and the insoluble material was filtered. The organic layer was separated from the filtrate. After drying over magnesium sulfate, the solvent was removed to obtain 61.2 g of 2-(2-acetoxyethyl)-3,4-difluoroaniline. To this compound, 60 g (276 mmol) of diethyl ethoxymethylenemalonate was added, and the mixture was heated at 120° C. for 5 hours. After air-cooled, the crystal was filtered off and washed with ether to obtain 78.2 g of the subject compound (2) in a 74% yield.

REFERENCE EXAMPLE 3

Ethyl 6,7-Difluoro-4-hydroxy-8-(2-hydroxyethyl)quinoline-3-carboxylate (3)

78 g (203 mmol) of the compound (2) obtained in Reference Example 2 was added to 1.0 l of Dowtherm A (Trade Name), and the mixture was boiled for 2 minutes. After air-cooled, the precipitated crystal was filtered off and washed with ether to obtain 32 g of a mixture of ethyl 8-(2-acetoxyethyl)-6,7-difluoro-4-hydroxyquinoline-3-carboxylate and ethyl 8,9-difluoro-6-oxo-6H-pyrrolo[3,2,1-ij]quinoline-5-carboxylate. The obtained mixture and 4.26 g of sodium ethoxide were added to 730 ml of ethanol, and the solution was heated under reflux for one day. After air-cooled to room temperature, 5.1 g of a precipitated pyrroloquinoline derivative crystal was filtered off, and the filtrate was concentrated to 150 ml. The crystal was filtered off and washed consecutively with ethanol and ether to obtain 23.8 of the subject compound (3) in a 40% yield.

REFERENCE EXAMPLE 4

Ethyl 1-Amino-6,7-difluoro-8-(2-hydroxyethyl)-1,4-dihydro-4-oxoquinoline-3-carboxylate (4)

6.13 g (20 mmol) of the quinoline compound (3) obtained in Reference Example 3 and 8.8 g (60 mmol) of anhydrous potassium carbonate were added to 100 ml of N,N-dimethylformamide, and the mixed solution was stirred at room temperature for 4 hours. 20 g (NET 17 g, 82 mmol) of mesitylenesulfonylhydroxyamine hydrate was dissolved in 100 ml of methylene chloride, and after drying over sodium sulfate, while cooling on ice, this methylene chloride solution was dropped to the mixed solution through 20 minutes. The obtained solution was stirred overnight. Methylene chloride was removed under reduced pressure by distillation, and 100 ml of water was added to the solution. The solution was stirred for 30 minutes at room temperature. The crystal was filtered off and washed successively with water, ethanol and ether to obtain 3.30 g of the subject compound (4) in a 53% yield.

EXAMPLE 1

Ethyl 4,5-Difluoro-2,3-dihydro-7-oxo-1H,7H-pyrido[3,2,1-ij]cinnoline-8-carboxylate (5)

11.8 g (36 mmol) of 1-aminoquinolone (4) obtained in Reference Example 4 and 15.1 g (58 mmol) of triphenylphosphine were added to 300 ml of tetrahydrofuran, and to this mixed solution, 500 ml of tetrahydrofuran solution containing 9.9 g (57 mmol) of diethyl azodicarboxylate was dropped through 3 hours at room temperature. The solution was stirred for 3 hours as it was, and the solvent was removed by distillation. The crystal was dispersed in ethanol, and was filtered off and washed successively with ethanol and ether to obtain 9.5 g of the subject compound (5) in a 89% yield. The result of the analysis of this compound was as follows.

$^1$H-NMR (DMSO-d$_6$)

1.27 (t, J=7.3 Hz, 3H), 2.95 (t, J=5.1 Hz, 2H), 3.31 (s, 3H), 3.40 (t, J=5.8 Hz, 2H), 4.21 (q, J=7.3 Hz, 2H), 6.86 (t, J=6.6 Hz, 1H), 7.91 (dd, J=11.0 Hz, J=8.8 Hz, 1H), 8.42 (s, 1H)

EXAMPLE 2

(1) Methyl 4,5-Difluoro-2,3-dihydro-1-methyl-7-oxo-1H,7H-pyrido[3,2,1-ij]cinnoline-8-carboxylate (6)

To 9.5 g (33 mmol) of pyridocinnoline (5) obtained in Example 1, 95 ml of dimethylsulfate was added, and the mixture was heated at 100° to 120° C. for 8 hours. After air-cooled, the solution was added to 900 ml of water containing 137 g of anhydrous potassium carbonate, and the solution was stirred at room temperature for 30 minutes. The solution was extracted with 800 ml of chloroform and after drying over magnesium sulfate, the solvent was removed by distillation. The residue was purified by silica gel chromatography (250 g of silica gel, eluent solvent: chloroform), and the obtained crystal was filtered off and washed with ether to obtain 5.3 g of the subject compound (6) in a 56% yield. The result of the analysis of this compound was as follows.

$^1$H-NMR (CDCl$_3$)

2.87 (s, 3H), 3.09 (t, J=6.2 Hz, 2H), 3.50 (t, J=6.2 Hz, 2H), 3.93 (s, 3H), 8.17 (dd, J=9.6 Hz, J=9.5 Hz, 1H), 8.61 (s, 1H)

(2) The following compound (7) was obtained in the similar manner as Example 2 (1).

Ethyl 4,5-Difluoro-2,3-dihydro-1-ethyl-7-oxo-1H,7H-pyrido[3,2,1-ij]cinnoline-8-carboxylate (7)

The result of the analysis of this compound was as follows.

$^1$H-NMR (CDCl$_3$)

1.19 (t, J=6.9 Hz, 3H), 1.41 (t, J=7.0 Hz, 3H), 2.96–3.06 (m, 4H), 3.56 (t, J=6.9 Hz, 2H), 4.39 (q, J=7.0 Hz, 2H), 8.14 (dd, J=9.5 Hz, 9.5Hz, 1H), 8.54 (s, 1H)

EXAMPLE 3

(1) 4,5-Difluoro-2,3-dihydro-1-methyl-7-oxo-1H,7H-pyrido[3,2,1-ij]cinnoline-8-carboxylic acid (8)

5.3 g (18 mmol) of methyl ester (6) obtained in Example 2 (1) was added to 250 ml of tetrahydrofuran, and, while the solution was heated under reflux, 100 ml of aqueous solution containing 0.76 g (19 mmol) of sodium hydroxide was added to the solution. The obtained solution was heated under reflux for 1.5 hours. After air-cooled, while cooling on ice, the solution was neutralized with 4.2 g (20 mmol) of citric hydrate and stirred for 1 hour. The solid was filtered off and washed consecutively with water, ethanol and ether to obtain 3.78 g of the subject compound (8) in a 75% yield. The result of the analysis of this compound was as follows.

Colorless powder:

Melting point: 264°–265° C. (decomp.)

$^1$H-NMR (DMSO-d$_6$)

2.88 (s, 3H), 3.14 (t, J=5.9 Hz, 2H), 3.54 (t, J=5.9 Hz, 2H), 8.18 (dd, J=11 Hz, J=8 Hz, 1H), 8.82 (s, 1H)

(2) 29.1 g of methyl ester (6) obtained in Example 2 (1) was added to 80 ml of concentrated hydrochloric acid and 320 ml of acetic acid, and the solution was heated under reflux for 3.5 hours. After air-cooled, 500 ml of water was added to the solution, and the solid was filtered off and washed consecutively with water, ethanol and ether to obtain 23.2 of crude solid. The obtained crude solid was recrystallized from ethanol and chloroform to obtain 21 g of subject compound (8) in a 80% yield. The result of the analysis of this compound was as follows.

Colorless prisms:

Melting point: 264°–265° C. (decomp.)

(3) The following compound (9) was obtained in the similar manner as Example 3 (2).

4,5-Difluoro-2,3-dihydro-1-ethyl-7-oxo-1H,7H-pyrido[3,2,1-ij]cinnoline-8-carboxylic acid (9)

The result of the analysis of this compound was as follows.

Colorless prisms:

Melting point: 231°–232.5° C.

$^1$H-NMR (DMSO-d$_6$)

1.09 (t, J=7.3 Hz, 3H), 3.01–3.12 (m, 4H), 3.61 (t, J=5.9 Hz, 2H), 8.16 (dd, J=10.3 Hz, 10.3 Hz, 1H), 8.71 (s, 1H)

(4) The following compound (10) was obtained in the similar manner as Example 3 (2).

4,5-Difluoro-2,3-dihydro-7-oxo-1H,7H-pyrido[3,2,1-ij]cinnoline-8-carboxylic acid (10)

The result of the analysis of this compound was as follows.

Colorless powder:

Melting point: 265° C. (decomp.)

$^1$H-NMR (DMSO-d$_6$)

3.03, 3.47 (each brs, each 2H), 7.27 (brs, 1H), 8.12 (dd, J=8.4 Hz, 8.4 Hz, 1H), 8.68 (s, 1H)

EXAMPLE 4 (METHOD A)

(1)
4-(3-Aminopyrrolidin-1-yl)-5-fluoro-2,3-dihydro-1-methyl-7-oxo-1H,7H-pyrido[3,2,1-ij]cinnoline-8-carboxylic acid (11)

50 mg (0.18 mmol) of 4,5-difluoro compound (8) obtained in Example 3 (1) and 80 mg (0.93 mmol) of 3-aminopyrrolidine were added to 1 ml of N,N-dimethylformamide, and the solution was heated at 100° C. for 1 hour. Then, the solvent was removed by distillation, and distillated together with toluene. Ethanol was added to the residue to solidify, and the solid was filtered off and washed successively with ethanol and ether to obtain 50 mg of the subject compound (11) in a 81% yield. The result of the analysis of this compound was as follows.

Colorless powder:
Melting point: 217°–218° C. (decomp.)
$^1$H-NMR (DMSO-$d_6$)
1.65–1.76 (m, 1H), 2.01–2.11 (m, 1H), 2.91 (s, 3H), 2.95 (t, J=5.5 Hz, 2H), 3.27–3.76 (m, 7H), 7.81 (d, J=14.2 Hz, 1H), 8.66 (s, 1H)

(2) to (22): Compounds (12) to (29) and compound (101) to (103) shown in Tables 3 to 7 were obtained according to the method A. The results of the analysis of these compounds were shown in Tables 3 to 7.

TABLE 3

[Structure: quinolone core with F, COOH, C=O, N-N-R⁴, and Y substituent]

| Example No. | Compound No. | R⁴ | Y | Property | Melting point (°C.) | Reaction solvent | ¹H-NMR | Preparing method |
|---|---|---|---|---|---|---|---|---|
| 4(2) | 12 | $CH_3$ | [4-amino-4-methylpiperidin-1-yl: H₂N, CH₃ on ring] | Colorless powder | 219—220 | DMF | DMSO-$d_6$ 1.05, 1.06(each s, each 3H), 1.71-1.96(m, 2H), 2.19-2.27(m, 1H), 2.91(s, 3H), 3.34-3.73 (m, 8H), 7.83(d, J=14.3Hz, 1H), 8.67(s, 1H) | method A |
| 4(3) | 13 | $CH_3$ | [4-methylaminopiperidin-1-yl: CH₃N] | Slightly yellowish powder | 245 decomp. | DMF | DMSO-$d_6$ 2.26(s, 3H), 2.90(s, 3H), 3.05(t, J=5.5Hz, 2H), 3.26, 3.34(each brs, each 4H), 3.46 (t, J=5.5Hz, 2H), 7.91(d, J=12.5Hz, 1H), 8.74 (s, 1H) | method A |
| 4(4) | 14 | $CH_3$ | [3-aminopiperidin-1-yl: H₂N, stereo] | Slightly pinkish powder | 207–209 decomp. | DMF | DMSO-$d_6$ 1.65-1.73(m, 1H), 2.02-2.10(m, 1H), 2.91(s, 3H), 2.95(brs, 2H), 3.23-3.80(m, 7H), 7.81 (d, J=13.9Hz, 1H), 8.66(s, 1H) | method A |
| 4(5) | 15 | $CH_3$ | [3-aminopiperidin-1-yl: H₂N, stereo] | Slightly pinkish powder | 211–214 decomp. | DMF | DMSO-$d_6$ 1.65-1.72(m, 1H), 2.02-2.09(m, 1H), 2.91(s, 3H), 2.95(brs, 2H), 3.34-3.78(m, 7H), 7.81 (d, J=13.9Hz, 1H), 8.66(s, 1H) | method A |
| 4(6) | 16 | $CH_3$ | [piperazin-1-yl: HN] | Slightly yellowish powder | 236–239 decomp. | DMF | DMSO-$d_6$ 2.85(brs, 4H), 2.89(s, 3H), 3.06(brs, 2H), 3.16(brs, 4H), 3.46(brs, 2H), 7.91(d, J=12.1Hz, 1H), 8.73(s, 1H) | method A |

TABLE 4

| Example No. | Compound No. | R[4] | Y | Property | Melting point (°C.) | Reaction solvent | ¹H-NMR | Preparing method |
|---|---|---|---|---|---|---|---|---|
| 4(7) | 17 | $CH_3$ | 2,6-dimethylpiperazin-1-yl | Slightly yellowish powder | 216–218 decomp. | DMF | DMSO-$d_6$ 1.01(d, J=5.5Hz, 6H), 2.76–3.66 (m, 10H), 2.90(s, 3H), 7.91(d, J=13.5Hz, 1H), 8.74(s, 1H) | method A |
| 4(8) | 18 | $CH_3$ | 2-methylpiperazin-1-yl | Slightly brown powder | 211–214 decomp. | DMF | DMSO-$d_6$ 1.17(d, J=5.1Hz, 3H), 2.90(s, 3H), 3.08–3.71 (m, 11H), 7.93(d, J=13.2Hz, 1H), 8.75(s, 1H) | method A |
| 4(9) | 19 | $CH_3$ | thiomorpholin-4-yl | Slightly yellowish powder | 275 decomp. | DMF | DMSO-$d_6$ 2.78(brs, 4H), 2.90(s, 3H), 3.07(brs, 2H), 3.45(brs, 6H), 7.93(d, J=11.7Hz, 1H), 8.75(s, 3H) | method A |
| 4(10) | 20 | $CH_3$ | piperidin-1-yl | Slightly yellowish powder | 246–248 | DMF | DMSO-$d_6$ 1.94(brs, 4H), 2.91(s, 3H), 2.95(t, J=5.1Hz, 2H), 3.42(t, J=5.9Hz, 2H), 3.56(brs, 4H), 7.82 (d, J=13.9Hz, 1H), 8.67(s, 1H) | method A |
| 4(11) | 21 | $CH_3$ | morpholin-4-yl | Colorless powder | 274 decomp. | DMF | DMSO-$d_6$ 2.90(s, 3H), 3.10(t, J=5.5Hz, 2H), 3.34(brs, 4H), 3.69(t, J=4.8Hz, 2H), 3.76(brs, 4H), 7.93 (d, J=12.5Hz, 1H), 8.75(s, 1H) | method A |
| 4(12) | 22 | $CH_3$ | 1,2,3,4-tetrahydroisoquinolin-2-yl | Slightly brown powder | 252 decomp. | DMF | DMSO-$d_6$ 2.94(s, 3H), 3.10(t, J=5.5Hz, 2H), 3.48 (t, J=5.5Hz, 2H), 4.83(s, 4H), 7.30–7.40(m, 4H), 7.95(d, J=13.6Hz, 1H), 8.75(s, 1H) | method A |

TABLE 5

| Example No. | Compound No. | R⁴ | Y | Property | Melting point (°C.) | Reaction solvent | ¹H-NMR | Preparing method |
|---|---|---|---|---|---|---|---|---|
| 4(13) | 23 | $CH_3$ | (CH₃)₂N–CH₃ | Slightly brown powder | 169 decomp. | DMF | DMSO-$d_6$ 2.91–2.98, 2.99(each s, each 3H), 3.02 (t, J=5.9Hz, 2H), 3.45(t, J=5.9Hz, 2H), 7.89(d, J=13.2Hz, 1H), 8.72(s, 1H) | method A |
| 4(14) | 24 | $CH_3$ | (tetrahydropyridinyl)N– | Slightly brown powder | 256–261 decomp. | DMF | DMSO-$d_6$ 2.91(s, 3H), 3.01(t, J=5.9Hz, 2H), 3.46 (t, J=5.9Hz, 2H), 4.33(s, 4H), 6.05(s, 2H), 7.91(d, J=13.6Hz, 1H), 8.72(s, 1H) | method A |
| 4(15) | 25 | $CH_3$ | (imidazolyl) | Colorless powder | >300 | DMF | DMSO-$d_6$ 2.89(brs, 2H), 2.95(s, 3H), 3.46(t, J= 5.5Hz, 2H), 7.24, 7.62, 8.08(each s, each 1H), 8.21(d, J=9.5Hz, 1H), 8.87(s, 1H) | method A |

TABLE 6

| Example No. | Compound No. | R⁴ | Y | Property | Melting point (°C.) | Reaction solvent | ¹H-NMR | Preparing method |
|---|---|---|---|---|---|---|---|---|
| 4(16) | 26 | $CH_3$ | cyclopropyl–NH– | Colorless prisms | 228.5–229.5 | DMF | DMSO-$d_6$ 0.67(brs, 2H), 0.71–0.75, 2.78–2.81(each m, each 2H), 2.81(s, 3H), 3.02(brs, 1H), 3.46 (t, J=5.9Hz, 2H), 6.40(brs, 1H), 7.79(d, J=13.6Hz, 1H), 8.59(s, 1H) | method A |
| 4(17) | 27 | $CH_3$ | HN⟨piperazinyl⟩N– | Slightly brown powder | 213–215 decomp. | DMF | DMSO-$d_6$ 1.88(brs, 2H), 2.90(s, 3H), 2.95, 3.03, 3.10, 3.35(each brs, each 2H), 3.49(brs, 4H), 7.92(d, J= 13.5Hz, 1H), 8.74(s, 1H) | method A |
| 4(18) | 28 | $C_2H_5$ | H₂N–(piperidinyl)N– | Colorless powder | 245–247 decomp. | $CH_3CN$ | DMSO-$d_6$ 1.11(t, J=7.0Hz, 3H), 1.82–1.96, 2.14–2.23(each m, each 1H), 2.97(brs, 2H), 3.09(q, J=7.0Hz, 2H), 3.43(t, J=6.6Hz, 2H), 3.65–3.85(m, 5H), 7.83(d, J= 13.9Hz, 1H), 8.58(s, 1H) | method A |
| 4(19) | 29 | $C_2H_5$ | CH₃N⟨piperazinyl⟩N– | Slightly yellowish powder | 208 | DMF | DMSO-$d_6$ 1.11(t, J=7.3Hz, 3H), 2.50(s, 3H), 2.75–3.14(m, 8H), 3.54(brs, 2H), 7.93(d, J=12.8Hz, 1H), 8.65(s, 1H) | method A |

TABLE 7

| Example No. | Compound No. | R⁴ | Y | Property | Melting point (°C.) | Reaction solvent | ¹H-NMR | Preparing method |
|---|---|---|---|---|---|---|---|---|
| 4(20) | 101 | $CH_3$ | CH₃O–, H₂N– substituted piperidinyl-N– Isomer B | Yellowish powder | 171–175 decomp. | $CH_3CN$ | DMSO-$d_6$ 2.91(s, 6H), 3.00–3.16(m, 1H), 3.18–3.75(m, 10H), 3.94(brs, 1H), 7.83(d, J=16.2Hz, 1H), 8.68(s, 1H) | method A |
| 4(21) | 102 | H | (piperidinyl)N– | Yellowish powder | 244–248 | DMF | DMSO-$d_6$ 1.93(brs, 4H), 2.86(brs, 2H), 3.30(brs, 2H), 3.47 (s, 4H), 7.18(brs, 1H), 7.77(d, J=14.0Hz, 1H), 8.55(s, 1H), | method A |

TABLE 7-continued

| Example No. | Compound No. | R⁴ | Y | Property | Melting point (°C.) | Reaction solvent | ¹H-NMR | Preparing method |
|---|---|---|---|---|---|---|---|---|
| 4(22) | 103 | CH₃ | CH₃N⟩N— | Yellowish powder | 145–148 | DMF | DMSO-d₆ 1.02(d, J=6.3Hz, 3H), 2.22(brs, 4H), 2.65(brs, 2H), 2.91(s, 6H), 2.92–3.95(m, 5H), 7.95(d, J=12.8Hz, 1H), 8.77(s, 1H) | method A |

EXAMPLE 5 (METHOD B)

(1) 4-(cis (−) 3-Amino-4-methylpyrrolidin-1-yl)-5-fluoro-2,3-dihydro-1-methyl-7-oxo-1H,7H-pyrido[3,2,1-ij]cinnoline-8-carboxylic acid (30)

1.0 g (3.6 mmol) of 4,5-difluoro compound (8) obtained in Example 3 (1), 0.93 g (5.4 mmol) of cis (−) 3-amino-4-methylpyrrolidine dihydrochloride and 2.95 g (19.4 mmol) of 1,8-diazabicyclo[5.4.0]-7-undecene were added to 20 ml of N,N-dimethylformamide, and the solution was heated at 110° to 120° C. for 40 minutes. Then, the solvent was removed by distillation, and the solution was distillated together with toluene. 20 ml of ethanol and 1.2 g of acetic acid were added to the residue. The solution was left at room temperature as it was, and the precipitated solid was filtered off and washed successively with ethanol and ether to 750 mg of the subject compound (30) in a 58% yield. The result of the analysis of this compound was as follows.

Yellowish powder:
Melting point: 160°–162° C. (decomp.)
¹H-NMR (DMSO-d₆)
1.07 (d, J=6.6 Hz, 8H), 2.39–2.44 (m, 1H), 2.91 (s, 3H), 2.95 (brs, 2H), 3.21–3.70 (m, 6H), 3.94–3.99 (m, 1H), 7.82 (d, J=14.3 Hz, 1H), 8.67 (s, 1H)

The obtained powder was recystallized from a mixture solvent of ethanol and water and the crystal was analyzed by X-ray.

In the recrystallized crystal, a torsion angle between 3-amino group and 4-methyl group on pyrrolidine ring was 48.9, and thus it was confirmed that this was a cis conformation.

(2) to (26): Compounds (31) to (54) and compound (104) shown in Tables 8 to 12 were obtained according to the B method. The results of the analysis of these compounds were shown in Table 8 to 12.

TABLE 8

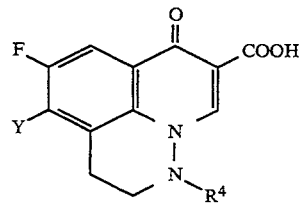

| Example No. | Compound No. | R⁴ | Y | Property | Melting point (°C.) | Reaction solvent | ¹H-NMR | Preparing method |
|---|---|---|---|---|---|---|---|---|
| 5(2) | 31 | CH₃ | H₂N–⟩N— | Brown powder | 179–182 decomp. | DMF | DMSO-d₆ 2.81(s, 3H), 2.97(brs, 2H), 4.11(brs, 1H), 7.82(d, J=13.5Hz, 1H), 8.60(s, 1H) | method B |
| 5(3) | 32 | CH₃ | OH–⟩N— | Colorless powder | 239–242 | DMF | DMSO-d₆ 1.82–1.91(m, 1H), 1.96–2.06(m, 1H), 2.77–3.54(m, 6H), 2.91(s, 3H), 3.80–3.89(m, 2H), 4.40(brs, 1H), 5.04(d, J=3.7Hz, 1H), 7.82(d, J=14.3Hz, 1H), 8.66(s, 1H) | method B |

TABLE 9

| Example No. | Compound No. | R⁴ | Y | Property | Melting point (°C.) | Reaction solvent | ¹H-NMR | Preparing method |
|---|---|---|---|---|---|---|---|---|
| 5(4) | 33 | CH₃ | HO–⟩N— | Slightly yellowish powder | 235.5–237 decomp. | CH₃CN | DMSO-d₆ 1.82–1.91(m, 1H), 1.99–2.08(m, 1H), 2.75–3.14(m, 2H), 2.91(s, 3H), 3.27–3.53(m, 4H), 3.81–3.91(m, 2H), 4.41, 5.04(each brs, each 1H), 7.82(d, J=14.2Hz, 1H), 8.66(s, 1H) | method B |

TABLE 9-continued

| Example No. | Compound No. | R⁴ | Y | Property | Melting point (°C.) | Reaction solvent | ¹H-NMR | Preparing method |
|---|---|---|---|---|---|---|---|---|
| 5(5) | 34 | CH₃ | (4-hydroxypiperidin-1-yl, HO with wedge) | Colorless powder | 235–238 decomp. | CH₃CN | DMSO-d₆ 1.82–1.91(m, 1H), 1.99–2.08(m, 1H), 2.75–3.14(m, 2H), 2.91(s, 3H), 3.27–3.53(m, 4H), 3.81–3.91(m, 2H), 4.41, 5.04(each brs, each 1H), 7.82(d, J=14.2Hz, 1H), 8.66(s, 1H) | method B |
| 5(6) | 35 | CH₃ | (4-amino-4-methylpiperidin-1-yl, H₂N) | Slightly yellowish powder | 215 decomp. | CH₃CN | DMSO-d₆ 1.41(s, 3H), 1.95–2.05(m, 2H), 2.91(s, 3H), 3.01(brs, 2H), 3.20–3.63(m, 5H), 3.75–3.85(m, 1H), 7.86(d, J=13.9Hz, 1H), 8.69(s, 1H) | method B |
| 5(7) | 36 | CH₃ | (H₂N, CH₃O substituted piperidine) trans | Colorless powder | 256–259 decomp. | CH₃CN | DMSO-d₆ 2.92, 3.37(each s, each 3H), 3.08, 3.77(each brs, each 2H), 3.92–4.13(m, 4H), 7.89(d, J=8.1Hz, 1H), 8.71(s, 1H) | method B |
| 5(8) | 37 | CH₃ | (aminomethyl-methylpiperidine) trans | Colorless powder | 193–195 | CH₃CN | DMSO-d₆ 1.08(d, J=6.2Hz, 3H), 1.79–1.86, 1.96–2.07(each m, each 1H), 2.90(s, 3H), 3.05–3.70(m, 10H), 7.80(d, J=13.9Hz, 1H), 8.65(s, 1H) | method B |
| 5(9) | 38 | CH₃ | (aminomethyl-methylpiperidine) cis | Colorless powder | 235 decomp. | CH₃CN | DMSO-d₆ 1.00(d, J=8.1Hz, 3H), 2.22–2.31(m, 1H), 2.92(s, 3H), 3.60(d, J=5.4Hz, 2H), 3.80–3.90(m, 1H), 7.82(d, J=16.2Hz, 1H), 8.64(s, 1H) | method B |

TABLE 10

| Example No. | Compound No. | R⁴ | Y | Property | Melting point (°C.) | Reaction solvent | 1H-NMR | Preparing method |
|---|---|---|---|---|---|---|---|---|
| 5(10) | 39 | CH₃ | H₂N—[cyclohexyl-N]—CH₃COOH trans (−) | Slightly yellowish powder | 204–206 decomp. | CH₃CN | DMSO-d₆ 1.08(d, J=6.2Hz, 3H), 1.90(s, 3H), 1.92-2.02 (m, 1H), 2.91(s, 3H), 2.99-3.13(m, 2H), 3.33-3.55(m, 5H), 3.65-3.80(m, 2H), 7.81(d, J=14.6Hz, 1H), 8.66(s,1H) | method B |
| 5(11) | 40 | CH₃ | H₂N—[cyclohexyl-N]—CH₃COOH trans (+) | Slightly yellowish powder | 204–206 decomp. | CH₃CN | DMSO-d₆ 1.08(d, J=6.2Hz, 3H), 1.90(s, 3H), 1.92-2.02 (m, 1H), 2.91(s, 3H), 2.99-3.13(m, 2H), 3.33-3.55(m, 5H), 3.65-3.80(m, 2H), 7.81(d, J=14.6Hz, 1H), 8.66(s, 1H) | method B |
| 5(12) | 41 | CH₃ | CH₃N—[cyclohexyl-N]— H cis | Colorless powder | 246–247 | CH₃CN | DMSO-d₆ 1.01(d, J=7.0Hz, 3H), 2.35-2.45(m, 1H), 2.50, 2.91 (each s, each 3H), 3.16(q, J=5.1Hz, 1H), 3.30(brs, 1H), 3.35-3.54(m, 4H), 3.65-3.79 (m, 2H), 7.80(d, J=14.3Hz, 1H), 8.64(s, 1H) | method B |
| 5(13) | 42 | CH₃ | CH₃N—[cyclohexyl-N]— H trans | Colorless powder | 209–211 | CH₃CN | DMSO-d₆ 1.19(d, J=6.2Hz, 3H), 2.61, 2.92 each s, each 3H), 3.00-3.23, 3.40-3.50(each m, each 3H), 3.65-3.74(m, 1H), 3.81-3.95(m, 2H), 7.89(d, J=13.6Hz, 1H), 8.72(s, 1H) | method B |
| 5(14) | 43 | CH₃ | HO—[cyclohexyl-N]— | Slightly yellowish powder | 223.5 decomp. | CH₃CN | DMSO-d₆ 1.38(s, 3H), 1.89(brs, 2H), 2.78-2.88(m, 1H), 2.91(s, 3H), 3.01-3.18(m, 1H), 3.30-3.66(m, 5H), 3.94, 4.84(each brs, each 1H), 7.80 (d, J=14.3Hz, 1H), 8.65(s, 1H) | method B |
| 5(15) | 44 | CH₃ | H₂N—[cyclohexyl-N]— trans (−) | Slightly yellowish powder | 155 decomp. | CH₃CN | DMSO-d₆ 1.11(d, J=6.6Hz, 3H), 2.05-2.16(m, 1H), 2.91 (s, 3H), 3.05-3.57(m, 7H), 3.75(brs, 2H), 7.83(d, J=13.9Hz, 1H), 8.67(s, 1H) | method B |

TABLE 11

| Example No. | Compound No. | R⁴ | Y | Property | Melting point (°C.) | Reaction solvent | ¹H-NMR | Preparing method |
|---|---|---|---|---|---|---|---|---|
| 5(16) | 45 | $CH_3$ | H₂N-[cyclohexyl-N-]methyl, trans (±) | Slightly yellowish powder | 157 decomp. | $CH_3CN$ | DMSO-d₆ 1.11(d, J=6.6Hz, 3H), 2.05-2.16(m, 1H), 2.91 (s, 3H), 3.05-3.57(m, 7H), 3.75(brs, 2H), 7.83(d, J=13.9Hz, 1H), 8.67(s, 1H) | method B |
| 5(17) | 46 | $CH_3$ | H₂N-[cyclohexyl-N-]methyl, cis (±) | Slightly yellowish powder | 184-186 decomp. | $CH_3CN$ | DMSO-d₆ 1.07(d, J=7.0Hz, 3H), 2.91(s, 3H), 2.95-3.70 (m, 8H), 3.94-4.03(m, 1H), 7.84(d, J=14.6Hz, 1H), 8.67(s, 1H) | method B |
| 5(18) | 47 | $CH_3$ | morpholino-fused piperidine, trans | Colorless powder | 219-222 decomp. | $CH_3CN$ | DMSO-d₆ 2.66-2.76(m, 1H), 2.91(s, 3H), 2.91-3.75(m, 12H), 3.89-3.98(m, 1H), 7.83(d, J=13.9Hz, 1H), 8.67(s, 1H) | method B |
| 5(19) | 48 | $CH_3$ | HO-[piperidinyl]-N-methyl, cis | Slightly yellowish powder | 224-226 decomp. | $CH_3CN$ | CDCl₃ 1.16(d, J=6.9Hz, 3H), 2.27-2.40(m, 1H), 2.93 (s, 3H), 2.98(t, J=6.2Hz, 2H), 3.16-3.25(m, 1H), 3.40-3.52(m, 4H), 3.85-3.95(m, 2H), 4.15(brs, 1H), 7.98(d, J=13.6Hz, 1H), 8.78(s, 1H) | method B |
| 5(20) | 49 | $CH_3$ | HO-[piperidinyl]-N-methyl, trans | Slightly yellowish powder | 227-229 decomp. | $CH_3CN$ | CDCl₃ 1.20(d, J=6.6Hz, 3H), 2.35-2.50(m, 1H), 2.82 (t, J=8.0Hz, 2H), 2.93(s, 3H), 3.08-3.23(m, 1H), 3.34-3.57(m, 4H), 3.61-3.70(m, 1H), 4.01-4.12(m, 1H), 4.37(brs, 1H), 7.92(d, J=14.3Hz, 1H), 8.75(s, 1H) | method B |
| 5(21) | 50 | $CH_3$ | HON=[piperidinyl]-N- | Slightly brown powder | 195 decomp. | DMF | DMSO-d₆ 2.82(s, 3H), 3.31(s, 4H), 6.21(brs, 1H), 7.79(d, J=13.5Hz, 1H), 8.59(s, 1H) | method B |

TABLE 12

| Example No. | Compound No. | R⁴ | Y | Property | Melting point (°C.) | Reaction solvent | ¹H-NMR | Preparing method |
|---|---|---|---|---|---|---|---|---|
| 5(22) | 51 | $C_2H_5$ | 4-hydroxypiperidin-1-yl (HO, cis not indicated) | Yellowish prisms | 226–228 decomp. | $CH_3CN$ | DMSO-d₆ 1.11(t, J=7.7Hz, 3H), 1.81–1.91, 1.98–2.09 (each m, each 1H), 3.09(q, J=7.3Hz, 3H), 3.30 (brs, 2H), 3.36–3.60, 3.76–3.92(each m, each 3H), 4.40(brs, 1H), 5.00(brs, 1H), 7.82(d, J=14.3Hz, 1H), 8.56(s, 1H) | method B |
| 5(23) | 52 | $C_2H_5$ | 3-methyl-4-aminomethylpiperidin-1-yl, cis | Slightly yellowish powder | 235–237.5 decomp. | $CH_3CN$ | DMSO-d₆ 1.02(d, J=5.4Hz, 3H), 1.12(t, J=5.4Hz, 3H), 2.85(brs, 2H), 2.95–3.70(m, 9H), 3.75–3.87 (m, 1H), 7.83(d, J=16.3Hz, 1H), 8.57(s, 1H) | method B |
| 5(24) | 53 | H | 3-amino-4-methylpiperidin-1-yl, cis (−) | Slightly brown powder | 247–250 decomp. | $CH_3CN$ | DMSO-d₆ 1.10(d, J=6.6Hz, 3H), 2.95, 3.31(each brs, each 2H), 3.44–3.55(m, 3H), 3.76, 3.94, 7.21(each brs, each 1H), 7.83(d, J=13.9Hz, 1H), 8.58(s, 1H) | method B |
| 5(25) | 54 | H | 3-methyl-4-aminomethylpiperidin-1-yl, cis | Slightly brown powder | 180 decomp. | $CH_3CN$ | DMSO-d₆ 1.01(d, J=5.4Hz, 3H), 1.56–1.70(m, 1H), 2.65–2.95(m, 4H), 3.17–3.60(m, 5H), 3.72–3.79(m, 1H), 7.25(brs, 1H), 7.82(d, J=13.5Hz, 1H), 8.57(s, 1H) | method B |
| 5(26) | 104 | $CH_3$ | 4-(1-aminoethyl)piperidin-1-yl (1'S, 3R) | Colorless prisms | 182–183 decomp. | $CH_3CN$ | DMSO-d₆ 1.06(d, J=6.2Hz, 3H), 1.57–1.70(m, 1H), 1.95–2.10, 2.75–2.83(each m, each 2H), 2.91(s, 3H), 3.10–3.55 (m, 6H), 3.70–3.80(m, 1H), 7.82(d, J=13.9Hz, 1H), 8.66(s, 1H) | method B |

EXAMPLE 6 (METHOD C)

(1)

4-(3,7-Diazabicyclo[3.3.0]octan-3-yl)-5-fluoro-2,3-dihydro-1-methyl-7-oxo-1H,7H-pyrido[3,2,1-ij]cinnoline-8-carboxylic acid Hydrochloride (55)

50 mg (0.18 mmol) of 4,5-difluoro compound (8) obtained in Example 3 (1), 92 mg (0.34 mmol) of 3-t-butoxycarbonyl-3,7-diazabicyclo[3.3.0]octane carbonate and 109 mg (0.72 mmol) of 1,8-diazabicyclo[5.4.0]-7-undecene were added to 1 ml of N,N-dimethylformamide, and the solution was heated at 110° to 120° C. for 40 minutes. Then, the solvent was removed by distillation, and 20 ml of chloroform and 10 ml of water were added to the residue. The solution was acidified with citric acid. The organic layer was separated from the solution and was removed by distillation after drying over sodium sulfate. The solution was distilled together with toluene, and ethanol was added to the residue to disperse the solid. The solid was filtered off and washed consecutively with ethanol and ether to obtain 40 mg of the solid. Then, to the obtained solid, 0.9 ml of acetic acid and 0.2 ml of concentrated hydrochloric acid were added. The solution was stirred at room temperature for 15 minutes, and the solvent was removed by distillation. The residue was distillated together with ethanol, and the residue was triturated with ethanol. The solid was filtered off and washed successively with ethanol and ether to obtain 25 mg of the subject compound (55) in a 34% yield. The results of the analysis of this compound were as follows:

Yellowish powder:
Melting point: 265°–269° C. (decomp.)
$^1$H-NMR (DMSO-$d_6$)
2.91 (s, 3H), 2.93–3.19 (m, 6H), 3.29–3.59 (m, 8H), 7.92 (d, J=13.2 Hz, 1H), 8.74 (s, 1H), 9.06 (brs, 2H)

(2) to (18): Compounds (56) to (71) and compound (105) shown in Tables 13 to 16 were obtained according to the method C. The results of the analysis of these compounds were shown in Table 13 to 16.

TABLE 13

(structure: fluoroquinolone core with F, Y substituent, and N-R4 piperazine/amino group, bearing COOH)

| Example No. | Compound No. | R⁴ | Y | Property | Melting point (°C.) | Reaction solvent | ¹H-NMR | Preparing method |
|---|---|---|---|---|---|---|---|---|
| 6(2) | 56 | CH₃ | H₂N-/-(cyclohexyl)-, trans, ·HCl | Yellowish powder | 196 decomp. | CH₃CN | DMSO-d₆ 1.17(d, J=6.8Hz, 3H), 2.40–2.44(m, 1H), 2.91 (s, 3H), 2.98(brs, 2H), 3.22–3.64(m, 6H), 3.78–3.90 (m, 1H), 7.89(d, J=13.7Hz, 1H), 8.39(brs, 2H), 8.71(s, 1H) | method C |
| 6(3) | 57 | CH₃ | H₂N-/-(cyclohexyl)-C₂H₅, cis, ·HCl | Yellowish powder | 245 decomp. | CH₃CN | DMSO-d₆ 0.97(t, J=6.9Hz, 3H), 1.46, 1.61(each quint, each J=8.1Hz, each 1H), 2.40–2.47(m, 1H), 2.92(s, 3H), 3.09(brs, 2H), 3.30–3.42(m, 1H), 3.50–3.73(m, 4H), 3.85–3.95, 4.07–4.18(each m, each 1H), 7.86(d, J=14.3Hz, 1H), 8.37(brs, 2H), 8.69(s, 1H) | method C |
| 6(4) | 58 | CH₃ | H₂N-/-(cyclohexyl)-C₂H₅, trans, ·HCl | Slightly yellowish powder | 204–242 | CH₃CN | DMSO-d₆ 0.95(t, J=7.3Hz, 3H), 1.44, 1.73(each quint, each J=7.0Hz, each 1H), 2.20–2.30(m, 1H), 2.92(s, 3H), 3.01–3.14(m, 2H), 3.25(t, J=8.1Hz, 1H), 3.45(t, J=5.9Hz, 2H), 3.55–3.63(m, 2H), 3.86 (t, J=8.4Hz, 2H), 7.88(d, J=13.6Hz, 1H), 8.47(brs, 2H), 8.71(s, 1H) | method C |
| 6(5) | 59 | CH₃ | H₂N-/-(cyclohexyl)-, cis, ·HCl | Yellowish powder | 192–194 | CH₃CN | DMSO-d₆ 1.13(d, J=6.6Hz, 3H), 2.62–2.67(m, 1H), 2.91 (s, 3H), 3.04(brs, 2H), 3.30–3.70(m, 5H), 3.85 (brs, 1H), 4.05–4.08(m, 1H), 7.87(d, J=13.9Hz, 1H), 8.29(brs, 2H), 8.70(s, 1H) | method C |

TABLE 14

| Example No. | Compound No. | R⁴ | Y | Property | Melting point (°C.) | Reaction solvent | ¹H-NMR | Preparing method |
|---|---|---|---|---|---|---|---|---|
| 6(6) | 60 | $CH_3$ | ![structure with NHCH₃]·HCl | Yellowish powder | 175 decomp. | $CH_3CN$ | DMSO-$d_6$ 2.12–2.25, 2.27–2.43(each m, each 1H), 2.62 (s, 3H), 2.94(s, 3H), 3.13–3.20(m, 1H), 3.37–3.60 (m, 4H), 3.75, 3.83(each brs, each 2H), 7.89 (d, J=13.5Hz, 1H), 8.72(s, 1H), 9.44(brs, 2H) | method C |
| 6(7) | 61 | $CH_3$ | ![structure with NH₂]·HCl | Yellowish powder | 197 decomp. | $CH_3CN$ | DMSO-$d_6$ 1.78(q, J=4.7Hz, 1H), 2.15(q, J=6.4Hz, 1H), 2.55–2.60(m, 1H), 2.91(s, 3H), 2.95–3.00(m, 4H), 3.32–3.52, 3.57–3.70(each m, each 3H), 7.85(d, J=13.7Hz, 1H), 8.13(brs, 2H), 8.67(s, 1H) | method C |
| 6(8) | 62 | $CH_3$ | ![structure with H₂N, CH₃O] cis ·HCl | Slightly yellowish powder | 231–233 decomp. | $CH_3CN$ | DMSO-$d_6$ 2.82–2.97(m, 1H), 2.93(s, 3H), 3.06–3.20(m, 1H), 3.40(s, 3H), 3.35–3.52(m, 2H), 3.65–3.88(m, 4H), 3.91–4.02(m, 1H), 4.18(brs, 1H) 7.88(d, J=14.1Hz, 1H), 8.44(brs, 1H), 8.71(s, 1H) | method C |
| 6(9) | 63 | $CH_3$ | ![structure with NHC₂H₅]·HCl | Slightly brown powder | 165 decomp. | $CH_3CN$ | DMSO-$d_6$ 1.27(t, J=7.3Hz, 3H), 2.11–2.24, 2.28–2.39 (each m, each 1H), 2.92(s, 3H), 3.02(brs, 2H), 3.45(t, J=5.6Hz, 2H), 3.52–3.59(m, 1H), 3.69–3.91 (m, 4H), 7.89(d, J=13.7Hz, 1H), 8.72(s, 1H), 9.34(brs, 2H) | method C |
| 6(10) | 64 | $CH_3$ | ![structure with N(CH₃)₂]·HCl | Yellowish powder | 254–256 decomp. | $CH_3CN$ | DMSO-$d_6$ 1.62–1.83, 2.14–2.26(each m, each 1H), 2.78, 2.82, 2.91(each s, each 3H), 3.10–3.15(m, 1H), 3.22(t, J=5.4Hz, 2H), 3.36–3.76(m, 7H), 7.85(d, J=13.5Hz, 1H), 8.69(s, 1H) | method C |

TABLE 15

| Example No. | Compound No. | R⁴ | Y | Property | Melting point (°C.) | Reaction solvent | ¹H-NMR | Preparing method |
|---|---|---|---|---|---|---|---|---|
| 6(11) | 65 | CH₃ | 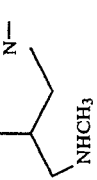 NHCH₃ ·HCl | Slightly yellowish powder | 268 decomp. | CH₃CN | DMSO-d₆ 1.74–1.85, 2.11–2.22(each m, each 1H), 2.57, 2.91(each s, each 3H), 2.61–2.70(m, 1H), 3.03(brs, 2H), 3.40–3.53, 3.57–3.72(each m, each 3H), 7.85(d, J=13.9Hz, 1H), 8.69(s, 1H), 8.97(brs, 1H) | method C |
| 6(12) | 66 | CH₃ | 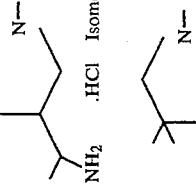 NH₂ ·HCl Isomer A | Slightly yellowish powder | 182–184 decomp. | CH₃CN | DMSO-d₆ 1.25(t, J=6.6Hz, 3H), 1.76–1.88, 2.11–2.22, 2.40–2.50(each m, each 1H), 2.91(s, 3H), 3.04–3.18, 3.22–3.33(each m, each 1H), 3.39–3.60(m, 4H), 3.65–3.76(m, 1H), 7.85(d, J=13.9Hz, 1H), 8.17(brs, 2H), 8.67(s, 1H) | method C |
| 6(13) | 67 | CH₃ | 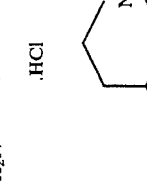 H₂N ·HCl | Slightly yellowish powder | 208 decomp. | CH₃CN | DMSO-d₆ 1.17, 1.21(each s, each 3H), 2.91(s, 3H), 2.95–3.14(m, 1H), 3.32–3.75(m, 7H), 4.03(t, J=13.5Hz, 1H), 7.87(d, J=13.7Hz, 1H), 8.47(brs, 2H), 8.69(s, 1H) | method C |
| 6(14) | 68 | CH₃ |  N(CH₃)₂ ·HCl | Colorless powder | 245 decomp. | CH₃CN | DMSO-d₆ 2.21–2.31, 2.35–2.44(each m, each 1H), 2.82 (brs, 6H), 2.92(s, 3H), 2.94–3.00(m, 1H), 3.01–3.17(m, 1H), 3.45(brs, 2H), 3.54–3.65(m, 2H), 3.80(t, J=8.1Hz, 2H), 3.97(brs, 1H), 7.91(d, J=13.5Hz, 1H), 8.72(s, 1H) | method C |
| 6(15) | 69 | CH₃ | 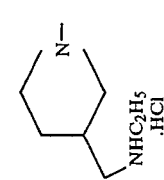 NHC₂H₅ ·HCl | Yellowish powder | 238–239.5 decomp. | CH₃CN | DMSO-d₆ 1.24(t, J=7.3Hz, 3H), 1.75–1.86, 2.13–2.23, 2.60–2.71(each m, each 1H), 2.91(s, 3H), 2.93–3.10(m, 5H), 3.40–3.55(m, 4H), 3.56–3.72(m, 3H), 7.85(d, J=14.3Hz, 1H), 8.68(s, 1H), 8.87(brs, 2H) | method C |

TABLE 16

| Example No. | Compound No. | R⁴ | Y | Property | Melting point (°C.) | Reaction solvent | 1H-NMR | Preparing method |
|---|---|---|---|---|---|---|---|---|
| 6(16) | 70 | CH₃ | 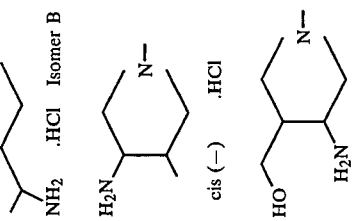 NH₂ ·HCl Isomer B | Yellowish powder | 241 decomp. | CH₃CN | DMSO-d₆ 1.30(d, J=6.6Hz, 3H), 1.68-1.81, 204-2.16, 2.36-2.48(2,75-2.88(each m, each 1H), 2.91(s, 3H), 3.13-3.79(m, 8H), 7.84(d, J=13.9Hz, 1H), 8.22(brs, 2H), 8.68(s, 1H) | method C |
| 6(17) | 71 | C₂H₅ | H₂N ... ·HCl cis (−) | Yellowish powder | 244 decomp. | CH₃CN | DMSO-d₆ 1.11(t, J=7.3Hz, 3H), 1.14(d, J=6.9Hz, 3H), 2.57-2.70(m, 1H), 3.03-3.11(m, 4H), 3.40-3.50 (m, 1H), 3.51-3.71(m, 4H), 3.84(brs, 1H) 4.03(t, J=8.1Hz, 2H), 7.85(d, J=14.3Hz, 1H), 8.40(brs, 2H), 8.59(s, 1H) | method C |
| 6(18) | 105 | CH₃ | HO H₂N ·HCl Isomer A | Slightly brown powder | 183-187 decomp. | CH₃CN | DMSO-d₆ 2.73(brs, 1H), 2.92(s, 3H), 3.06(brs, 2H), 3.26-3.96(m, 7H), 4.10-4.32(m, 2H), 7.91 (d, J=16.2Hz, 1H), 8.52(brs, 1H), 8.73(s, 1H) | method C |

EXAMPLE 7 (METHOD D)

(1)

5-Fluoro-4-{(pyrrolidin-3-yl)oxy}-2,3-dihydro-1-methyl-7-oxo-1H,7H-pyrido[3,2,1-ij]cinnoline-8-carboxylic acid Hydrochloride (72)

(2) to (4): Compounds (73) to (75) shown in Table 17 were obtained according to the method D. The results of the analysis of these compounds were shown in Table 17.

TABLE 17

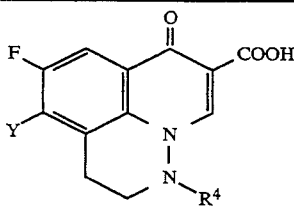

| Example No. | Compound No. | $R^4$ | Y | Property | Melting point (°C.) | Reaction solvent | $^1$H-NMR | Preparing method |
|---|---|---|---|---|---|---|---|---|
| 7(2) | 73 | $CH_3$ | H₂N–⟨△⟩–O– ·HCl | Colorless powder | 204–206 decomp. | | DMSO-$d_6$ 1.01(t, J=5.4Hz, 2H), 1.16(t, J=6.8Hz, 2H), 2.88(s, 3H), 3.18(t, J=5.4Hz, 2H), 3.52(t, J=5.9Hz, 2H), 4.41(s, 2H), 8.04(d, J=12.2Hz, 1H), 8.78(s, 1H), 8.84(brs, 2H) | method D |
| 7(3) | 74 | $CH_3$ | O–⟨□⟩–N H ·HCl | Colorless powder | 195–196.5 decomp. | | DMSO-$d_6$ 2.87(s, 3H), 3.09, 3.51, 4.21, 4.37(each brs, each 2H), 5.25(brs, 1H), 8.03(d, J=11.7Hz, 1H), 8.77(s, 1H) | method D |
| 7(4) | 75 | $C_2H_5$ | O–⟨pyrrolidine⟩–N H ·HCl | Colorless powder | 229–231 decomp. | | DMSO-$d_6$ 1.08(t, J=7.3Hz, 3H), 2.15-2.30(m, 2H), 2.90-3.17(m, 4H), 3.49(brs, 2H), 3.57(brs, 2H), 5.39(brs, 1H), 8.03(d, J=12.1Hz, 1H), 8.67(s, 1H) | method D |

278 mg (1 mmol) of 4,5-difluoro compound (8) obtained in Example 3 (1) and 374 mg (2 mmol) of 1-t-butoxycarbonyl-3-pyrrolidinol were added to 3 ml of N,N-dimethylformamide, and at room temperature 120 mg (3 mmol) of sodium hydride was added to the solution. The solution was stirred as it was, and the solvent was removed by distillation. Then, 15 ml of chloroform and 10 ml of water were added to the solution, and the solution was acidified with citric acid. The organic layer was separated and was removed by distillation after drying over sodium sulfate. The solution was distillated together with toluene, and ether was added to the residue to disperse the solid. The solid was filtered off to obtain 314 mg of the solid. To 180 mg of the obtained solid, 4 ml of acetic acid and 1 ml of concentrated hydrochloric acid were added at room temperature. The solution was stirred at room temperature for 15 minutes as it was, and the solvent was removed by distillation. The residue was distillated together with ethanol, and the residue was triturated with ethanol. The solid was filtered off and washed successively with ethanol and ether to obtain 144 g of the subject compound (72) in a 67% yield. The result of the analysis of this compound was as follows.

Slightly yellowish powder:
Melting point: 241° C. (decomp.)
$^1$H-NMR (DMSO-$d_6$)
2.12–2.31 (m, 2H), 2.89 (s, 3H), 2.98–3.59 (m, 8H), 5.40 (brs, 1H), 8.06 (d, J=12.1 Hz, 1H), 8.78 (s, 1H), 9.60, 9.75 (each brs, each 1H)

EXAMPLE 8 (METHOD E)

5-Fluoro-4-methoxy-2,3-dihydro-1-methyl-7-oxo-1H,7H-pyrido[3,2,1-ij]cinnoline-8-carboxylic acid (76)

50 mg (0.18 mmol) of 4,5-difluoro compound (8) obtained in Example 3 (1) and 30 mg of sodium methoxide were added to 5 ml of methanol, and the solution was heated under reflux for 5.5 hours. After air-cooled, 0.5 ml of acetic acid and 10 ml of methanol were added to the solution. The deposited solid was filtered off and washed successively with methanol and ether to obtain 50 g of the subject compound (76) in a yield. The result of the analysis of this compound was as follows.

Colorless powder:
Melting point: 236°–241° C.
$^1$H-NMR (DMSO-$d_6$)
2.86 (s, 3H), 3.04 (t, J=5.9 Hz, 2H), 3.50 (t, J=6.2 Hz, 2H), 4.10 (s, 3H), 8.02 (d, J=12.5 Hz, 1H), 8.76 (s, 1H),

EXAMPLE 9

(1) 4-(cis (−) 3-Amino-4-methylpyrrolidin-1-yl)-5-fluoro-2,3-dihydro-1-methyl-7-oxo-1H,7H-pyrido[3,2,1-ij]cinnoline-8-carboxylic acid Hydrochloride (77)

5.1 g of the compound (30) obtained in Example 5 (1) was dissolved in 110 ml of acetic acid, and then 25 ml of concentrated hydrochloric acid was added to the solution. The solution was stirred overnight at room temperature. The crystal was filtered off and washed successively with ethanol and ether to obtain 4.6 g of crude crystal. The filtrate was removed by distillation, and 80 ml of ethanol was added to the residue, and the deposited crystal was filtered off. The combined crude crystal was recrystallized from ethanol to obtain 4.61 g of the subject compound (77). The result of the analysis of this compound was as follows.

Yellowish prisms:
Melting point: 211°–214° C. (decomp.)
$^1$H-NMR (DMSO-$d_6$)
1.15 (d, J=7.0 Hz, 3H), 2.57–2.70 (m, 1H), 2.91 (s, 3H), 3.07 (brs, 2H), 3.30–3.72 (m, 5H), 3.84 (brs, 1H), 4.04–4.14 (m, 1H), 7.84 (t, J=14.3 Hz, 1H), 8.68 (s, 1H), (2) 4-(cis (−) 3-Amino-4-methylpyrrolidin-1-yl)-5-fluoro -2,3-dihydro-1-methyl-7-oxo-1H,7H-pyrido[3,2,1-ij]cinnoline-8-carboxylic acid Tosylate (78)

3.2 g of the compound (30) obtained in Example 5 (1) was dissolved in 110 ml of chloroform and 110 ml of methanol, and then 40 ml of methanol solution containing 6.37 g of p-toluenesufonic acid hydrate was added to the solution. The solution was stirred at room temperature for 40 minutes. The solvent was removed by distillation, and the crystal was dispersed in ethanol. The crystal was filtered off and washed successively with ethanol and ether to obtain 4.52 g of crude crystal. The crystal was recrystallized from a mixture solvent of ethanol and water to obtain 4.52 g of the subject compound (78). The result of the analysis of this compound was as follows.

Colorless needles:
Melting point: 258°–260° C.
$^1$H-NMR (DMSO-$d_6$)
1.12 (d, J=6.9 Hz, 3H), 2.28, 2.91 (each s, each 3H), 2.60–2.70 (m, 1H), 3.00 (brs, 2H), 3.35–3.68 (m, 5H), 3.88 (brs, 1H), 4.01–4.06 (m, 1H), 7.10 (d, J=7.7 Hz, 2H), 7.45 (d, J=8.0 Hz, 2H), 7.86 (d, J=13.9 Hz, 1H), 8.69 (s, 1H), (3) to (7): Compounds (79) to (83) shown in Table 18 were obtained according to Example 9 (2). The results of the analysis of these compounds were shown in Table 18.

TABLE 18

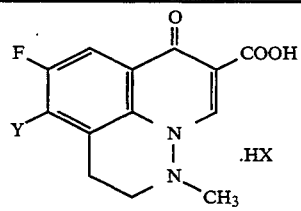

| Example No. | Compound No. | Y | HX | Property | Melting point (°C.) | $^1$H-NMR |
|---|---|---|---|---|---|---|
| 9(3) | 79 | (NH$_2$, 1'S, 3R piperidinyl) | HCl | Yellowish needles | >270 decomp. | DMSO-$d_6$ 1.29(d, J=6.2Hz, 3H), 1.68–1.81, 2.04–2.18, 2.36–2.48, 2.75–2.85 (each m, each 1H), 2.92(s, 3H), 3.13–3.79(m, 8H), 7.85(d, J=14.3Hz, 1H), 8.69(s, 1H) |
| 9(4) | 80 | (H$_2$N-piperidinyl, cis (−)) | CH$_3$SO$_3$H | Slightly yellowish needles | 265 decomp. | DMSO-$d_6$ 1.12(d, J=7.0Hz, 3H), 2.31, 2.92(each s, each 3H), 2.60–2.70(m, 1H), 3.01(brs, 2H), 3.35–3.66(m, 5H), 3.88(brs, 1H), 4.00–4.08(m, 1H), 7.88(d, J=13.9Hz, 1H), 8.70(s, 1H) |
| 9(5) | 81 | (H$_2$N-piperidinyl, cis (−)) | ½H$_2$SO$_4$ | Yellowish prisms | 202–205 decomp. | DMSO-$d_6$ 1.08(d, J=6.9Hz, 3H), 2.91(s, 3H), 2.96(brs, 2H), 3.35–3.70(m, 6H), 3.92–4.03(m, 1H), 7.82(d, J=13.9Hz, 1H), 8.66(s, 1H) |
| 9(6) | 82 | (H$_2$N-piperidinyl, cis (−)) | ½ HOOC-CH=CH-COOH | Slightly yellowish prisms | 219–220 decomp. | DMSO-$d_6$ 1.07(d, J=6.6Hz, 3H), 2.36–2,47(m, 1H), 2.91(s, 3H), 2.94–3.10(m, 2H), 3.30–3.65(m, 6H), 3.91–4.00(m, 1H), 6.42(s, 1H), 7.81 (d, J=14.6Hz, 1H) 8.65(s, 1H) |
| 9(7) | 83 | (H$_2$N-piperidinyl, cis (−)) | HOOC-CH=CH-COOH | Slightly yellowish needles | 201–202 | DMSO-$d_6$ 1.12(d, J=7.0Hz, 3H), 2.60–2.70(m, 1H), 2.91(s, 3H), 3.00(brs, 2H)3.35–3.68(m, 5H), 3.88(brs, 1H), 3.99–4.10(m, 1H), 6.02(s, 2H), 7.87(d, J=14.3Hz, 1H), 8.70(s, 1H) |

EXAMPLE 10

(1) 4-{cis (−) 3-(t-Butoxycarbonylaminoacetylamino)-4-methylpyrrolidin-1-yl}-5-fluoro-2,3-dihydro-1-methyl-7-oxo-1H,7H-pyrido[3,2,1-ij]cinnoline-8-carboxylic acid (84)

350 mg (2 mmol) of N-t-butoxycarbonylglycine and 202 mg (2 mmol) of N-methylmorpholine were added to 6 ml of methylene chloride. The mixture solution was cooled on freezing mixture, and 0.26 ml (2 mmol) of isobutyl chlorocarbonate was added to the solution. After 20 minutes, 716 mg (2 mmol) of the compound (30) obtained in Example 5 (1) was added to the solution, and the solution was stirred at room temperature for 30 minutes. Then, 10 ml of water was added to the solution, and the solution was acidified with by citric acid. The organic layer was separated from the solution and was removed distillation after drying over sodium sulfate. Ethyl acetate-ether was added to the residue, then the product came out of the solution, and the solid was filtered off to obtain 776 mg of the subject compound (84) in a 75% yield. The results of the analysis of this compound were as follows:

Yellowish powder:
Melting point: 142°–145° C.
$^1$H-NMR (CDCl$_3$)
1.12 (d, J=7.0 Hz, 3H), 1.45 (s, 9H), 2.54–2.65 (m, 1H), 2.87 (brs, 2H), 2.95 (s, 3H), 3.42–3.55 (m, 5H), 3.83–3.89 (m, 2H), 3.98–4.05 (m, 1H), 4.62, 5.46, 7.05 (each brs, each 1H), 7.70 (d, J=13.5 Hz, 1H), 8.63 (s, 1H), (2) to (4): Compounds (85) to (87) shown in Table 19 were obtained according to Example 10 (1). The results of the analysis of these compounds were shown in Table 19.

TABLE 19

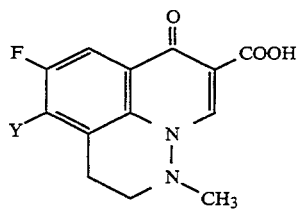

| Example No. | Compound No. | Y | Property | Melting point (°C.) | $^1$H-NMR |
|---|---|---|---|---|---|
| 10(2) | 85 | Boc—Ala—NH— (4-methylpiperidine) cis (−) | Slightly yellowish powder | 248–249.5 | CDCl$_3$ 1.08, 1.38(each d, each J=7.0Hz, each 3H), 1.46(s, 9H), 2.55–2.66 (m, 1H), 2.93(s, 5H), 3.35–3.60(m, 5H), 3.95–4.05, 4.10–4.20(each m, each 1H), 4.61(brs, 1H), 4.97(d, J=7.7Hz, 1H), 6.99(d, J=5.4Hz, 1H), 7.89(d, J=13.9Hz, 1H), 8.72(s, 1H) |
| 10(3) | 86 | Z—Val—NH— (4-methylpiperidine) cis (−) | Colorless powder | 147–148 | CDCl$_3$ 0.96(d, J=6.9Hz, 3H), 0.99(d, J=8.1Hz, 3H), 1.07(d, J=6.6Hz, 3H), 2.15–2.30(m, 1H), 2.50–2.65(m, 1H), 2.80–3.10(m, 2H), 2.93(s, 3H), 3.35–3.60(m, 5H), 3.95–4.10(m, 2H), 4.60(brs, 1H), 5.12(s, 2H), 5.46(d, J=9.2Hz, 1H), 6.77(d, J=8.0Hz, 1H), 7.31–7.33(m, 5H), 7.75(d, J=13.6Hz, 1H), 8.64(s, 1H) |
| 10(4) | 87 | Boc—Ala—NH— (4-methylpiperidine, different stereochem) | Yellowish powder | 140–141 decomp. | CDCl$_3$ 1.39(d, J=7.0Hz, 3H), 1.45(s, 9H), 2.02–2.15, 2.20–2.38(each m, each 1H), 2.94(s, 3H), 3.05(brs, 2H), 3.48(brs, 4H), 3.86(brs, 2H), 4.20, 4.56, 5.23, 7.22(each brs, each 1H), 7.77(d, J=13.5Hz, 1H), 8.64(s, 1H) |

EXAMPLE 11

(1) 4-{cis (−) 3-(Aminoacetylamino)-4-methylpyrrolidin-1-yl}-5-fluoro-2,3-dihydro-1-methyl-7-oxo-1H,7H-pyrido[3,2,1-ij]cinnoline-8-carboxylic acid Hydrochloride (88)

750 mg (1.5 mmol) of the compound (84) obtained in Example 10 (1) was added to 10 ml of dioxane and 10 ml of ethanol, and then 2.5 ml of 4N hydrochloric acid solution in dioxane was added to the solution. The solution was stirred at room temperature for 1 hour, and the solvent was removed by distillation. The powder was filtered off and washed successively with ethanol and ether to obtain 324 mg of the subject compound (88) in a 49% yield. The result of the analysis of this compound was as follows.

Yellowish powder:
Melting point: 196° C. (decomp.)
$^1$H-NMR (DMSO-d$_6$)
1.01 (d, J=6.6 Hz, 3H), 2.91 (s, 3H), 3.00 (brs, 2H), 3.30–3.70 (m, 7H), 4.06, 4.49 (each brs, each 1H), 7.83 (d, J=14.3 Hz, 1H), 8.13, 8.67 (each brs, each 2H), (2) to (8): Compounds (89) to (94) and compound (106) shown in Tables 20 and 21 were obtained, according to Example 11 (1). The results of the analysis of these compounds were shown in Tables 20 and 21.

TABLE 20

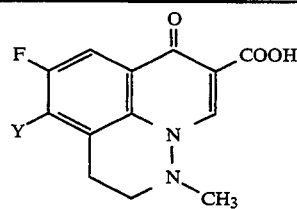

| Example No. | Compound No. | Y | Property | Melting point (°C.) | $^1$H-NMR |
|---|---|---|---|---|---|
| 11(2) | 89 | Ala—NH—[piperidine], cis (−) ·HCl | Yellowish powder | 198–200 | DMSO-$d_6$<br>1.03, 1.36(each d, each J=6.9Hz, each 3H), 2.91(s, 3H), 3.02(brs, 2H), 3.30–3.70(m, 5H), 3.90–4.10(m, 2H), 4.46(brs, 1H), 7.82(d, J=14.3Hz, 1H), 8.26, 8.66(each brs, each 2H) |
| 11(3) | 90 | Phe—NH—[piperidine] (D), cis (−) ·HCl | Yellowish powder | 186–189 decomp. | DMSO-$d_6$<br>0.67(d, J=7.0Hz, 3H), 2.31–2.45(m, 1H), 2.91(s, 3H), 2.98(brs, 2H), 3.07(d, J=7.3Hz, 2H), 3.32–3.60(m, 5H), 3.96–4.06(m, 1H), 4.21(t, J=6.6Hz, 1H), 4.37(brs, 1H), 7.32(brs, 5H), 7.81(d, J=14.6Hz, 1H), 8.35(brs, 2H), 8.66(s, 1H), 8.71(d, J=8.0Hz, 1H) |
| 11(4) | 91 | (CH$_3$)$_2$C(NH$_2$)—CONH—[piperidine], cis (−) ·HCl | Yellowish powder | 195 decomp. | DMSO-$d_6$<br>0.97(d, J=6.6Hz, 3H), 1.53, 1.56, 2.91(each s, each 3H), 3.03(brs, 2H), 3.35–3.54(m, 4H), 3.75, 3.96, 4.52(each brs, each 1H), 7.83(d, J=14.3Hz, 1H), 8.34(brs, 3H), 8.67(s, 1H) |
| 11(5) | 92 | Leu—NH—[piperidine], cis (−) ·HCl | Yellowish powder | 177–180 | DMSO-$d_6$<br>0.88(d, J=5.5Hz, 3H), 0.90(d, J=6.6Hz, 3H), 1.07(d, J=6.2Hz, 3H), 1.61 (brs, 3H), 2.92(s, 3H), 3.05(brs, 2H), 3.35–3.75(m, 5H), 4.02(brs, 2H), 4.47(brs, 1H), 7.81(d, J=13.9Hz, 1H), 8.41(brs, 2H), 8.66(s, 1H), 8.87(d, J=7.7Hz, 1H) |
| 11(6) | 93 | Ala—Ala—NH—[piperidine], cis (−) ·HCl | Yellowish powder | 194–197 | DMSO-$d_6$<br>0.97, 1.25, 1.35(each brs, each 3H), 2.92(s, 3H), 3.09(brs, 2H), 3.35–4.05(m, 8H), 4.45(brs, 1H), 7.85(d, J=13.5Hz, 1H), 8.20(brs, 3H, 8.67(brs, 2H) |

TABLE 21

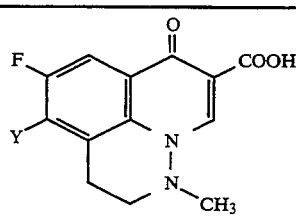

| Example No. | Compound No. | Y | Property | Melting point (°C.) | $^1$H-NMR |
|---|---|---|---|---|---|
| 11(7) | 94 | Ala—NH—[piperidine] ·HCl | Yellowish powder | 260 decomp. | DMSO-$d_6$<br>1.36(d, J=7.0Hz, 3H), 1.91–2.01, 2.16–2.26(each m, each 1H), 2.92(s, 3H), 3.00(brs, 2H), 3.37–3.64(m, 4H), 3.91–3.96(m, 3H), 4.41(brs, 1H), 7.83(d, J=13.9Hz, 1H), 8.27(brs, 2H), 8.68(s, 1H), 8.97(d, J=6.6Hz, 1H) |
| 11(8) | 106 | Ala—NH—CH—[piperidine] ·HCl, Isomer B | Yellowish powder | 188–190 | DMSO-$d_6$<br>1.10–1.15(m, 3H), 1.36(d, J=13.5Hz, 3H), 1.63–1.75, 2.00–2.10, 2.28–2.38, 2.78–2.85(each m, each 1H), 2.90(s, 3H), 3.00–3.10(m, 1H), 3.37–3.58(m, 5H), 3.70–3.83(m, 3H), 7.85(d, J=13.5Hz, 1H), 8.20(brs, 2H), 8.51–8.61(m, 1H), 8.67(m, 1H) |

EXAMPLE 12

4-{cis (−)
3-(2-Amino-3-methylbutanoyl)amino-4-methylpyrrolidin-1-yl}-5-fluoro-2,3-dihydro-1-methyl-7-oxo-1H,7H-pyrido [3,2,1-ij]cinnoline-8-carboxylic acid Hydrochloride (95)

850 mg (1.4 mmol) of the compound (86) obtained in Example 10 (3) was added to 60 ml of methanol and 10 ml of acetic acid, and then 300 mg of 5% palladium on carbon was added to the solution. The solution was stirred overnight under hydrogen. Then, palladium on carbon was filtered, and the solvent was removed by distillation. The residue was dissolved in 10 ml of methanol, and 2 ml of 4N hydrochloric acid solution in dioxane was added to the solution. The solvent was removed by distillation. The powder was filtered off and washed successively with ethanol and ether to obtain 600 mg of the subject compound (95) in a 87% yield. The result of the analysis; of this compound was as follows.

Yellowish powder:
Melting point: 198°–199.5° C. (decomp.)
$^1$H-NMR (DMSO-d$_6$)
0.93 (d, J=6.6 Hz, 6H), 1.07 (d, J=6.6 HZ, 3H), 2.05–2.15 (m, 1H), 2.91 (s, 3H), 3.02 (brs, 2H), 3.30–3.50 (m, 3H), 3.62 (t, J=8.4 Hz, 2H), 3.80, 4.04, 4.48 (each brs, each 1H), 7.82 (d, J=14.3 Hz, 1H), 8.29 (brs, 2H), 8.66 (s, 1H), 8,73 (d, J=7.7 Hz, 1H)

EXAMPLE 13

4-{cis (−)
3-((2-Amino-3-methylbutanoyl)aminoacetylamino)-4-methylpyrrolidin-1-yl}-5-fluoro-2,3-dihydro-1-methyl-7-oxo-1H,7H-pyrido[3,2,1-ij]cinnoline-8-carboxylic acid Hydrochloride (96)

758 mg (2 mmol) of (N-t-butoxycarbonylvalyl)glycine p-nitrophenyl ester, 202 mg (2 mmol) of triethylamine and 716 mg (2 mmol) of the compound (30) obtained in Example 5 (1) were added to 10 ml of methylene chloride. The mixture solution was stirred overnight at room temperature. 10 ml of water was added to the solution and the solution was acidified with citric acid. The organic layer was separated and was removed by distillation after drying over sodium sulfate. Ethyl acetate-ether was added to the residue, the product came out of the solution, and the solid was filtered off. The solid was added to 10 ml of methanol, and 2.5 ml of 4N hydrochloride solution in dioxane was added to the solution. After the solution was stirred at room temperature for 30 minutes, the solvent was removed by distillation. The powder was filtered off and washed successively with ethanol and ether to obtain 618 mg of the subject compound (96) in a 58% yield. The results of the analysis of this compound were as follows:

Yellowish powder:
Melting point: 189°–191° C.
$^1$H-NMR (DMSO-d$_6$)
0.94–1.00 (m, 9H), 2.00–2.18 (m, 1H), 2.91 (s, 3H), 3.01 (brs, 2H), 3.30–3.55 (m, 4H), 3.65 (brs, 2H), 3.73–3.89 (m, 1H), 3.94–4.05 (m, 2H), 4.47 (brs, 1H), 7.82 (d, J=14.3 Hz, 1H), 8.22 (brs, 3H), 8.66 (s, 1H), 8,74 (brs, 1H)

EXAMPLE 14

Ethyl
1-Amino-6,7-difluoro-8-acetoxymethyl-1,4-dihydro-4-oxoquinoline-3-carboxylate (97)

10.7 g (32.9 mmol) of ethyl 6,7-difluoro-4-hydroxy-8-acetoxymethylquinoline-3-carboxylate and 14.2 g (65.8 mmol) of anhydrous potassium carbonate were added to 130 ml of N,N-dimethylformamide, and the solution was stirred at room temperature for 4 hours. 14 g (NET 8.97 g, 49 mmol) of mesitylenesulfonylhydroxyamine was dissolved in 100 ml of methylene chloride, and after drying over sodium sulfate, while cooling on ice, this solution was dropped to the previous solution through 20 minutes. Then, the obtained solution was left overnight as it was. To this solution, 100 ml of water was added, and the solution was stirred at room temperature for 1 hour. The solution was extracted with methylene chloride, and the organic layer was washed. After drying over sodium sulfate, the solvent was removed under reduced pressure and ether was added to the crystal residue. The crystals were filtered off and washed with ether to obtain 6.4 g of the subject compound (97) in a 57% yield. The results of the analysis of this compound were as follows:

Colorless needles:
Melting point: 217°–221° C. (decomp.)
$^1$H-NMR (DMSO-d$_6$)
1.28 (t, J=7.3 Hz, 3H), 2.05 (s, 3H), 4.25 (q, J=7.3 Hz, 2H), 5.74 (s, 2H), 6.59 (brs, 2H), 8.15 (dd, J=9.2 Hz, 10.3 Hz, 1H), 8.59 (s, 1H)

EXAMPLE 15

Ethyl
1-Acetoamino-6,7-difluoro-8-acetoxymethyl-1,4-dihydro-4-oxoquinoline-3-carboxylate (98)

2 g (5.8 mmol) of 1-aminoquinoline (97) obtained in Example 14 and 80 mg of sodium ethoxide were added to 60 ml of ethanol, and the solution was heated at reflux for 1 day. After air-cooled to room temperature, the deposited crystal was filtered off, and filtrate was concentrated. The crystals were filtered off and washed consecutively with ethanol and ether to obtain 1.8 g of the subject compound (98) in a 90% yield. The results of the analysis of this compound were as follows:

Colorless needles:
Melting point: 243°–248° C. (decomp.)
$^1$H-NMR (DMSO-d$_6$)
1.28 (t, J=7.0 Hz, 3H), 2.04 (S, 3H), 4.25 (q, J=7.1 Hz, 2H), 4.82 (brs, 2H), 8.09 (dd, J=8.8 Hz, 10.3 Hz, 1H), 8.42 (s, 1H)

EXAMPLE 16

Ethyl
3,4-Difluoro-1,2-dihydro-1-acetyl-6-oxo-1H,6H-pyrido [3,2,1-hi]indazole-7-carboxylate (99)

0.85 g (2.5 mmol) of the compound (98) obtained in Example 15 and 0.98 g (3.75 mmol) of triphenylphosphine were added to 20 ml of tetrahydrofuran, and at room temperature 30 ml of tetrahydrofuran solution containing 0.65 g (3.75 mmol) of diethyl azodicarboxylate was dropped to the solution through 3 hours. The solution was left overnight as it was, and the solvent was removed by distillation. The crystals were dispersed in ether, filtered off and washed consecutively with ethanol and ether to obtain 0.51 g of the subject compound (99) in a 63% yield. The results of the analysis of this compound were as follows:
Colorless needles:
Melting point: 235°-237° C. (decomp.)
$^1$H-NMR (DMSO-d$_6$)
1.27 (t, J=6.6 Hz, 3H), 2.31 (s, 3H), 4.23 (q, J=7.3 Hz, 2H), 5.67 (s, 2H), 7.84 (dd, J=7.3 Hz, 10.3 Hz, 1H), 9.49 (s, 1H)

EXAMPLE 17

3,4-Difluoro-1,2-dihydro-6-oxo-1H,6H-pyrido[8,2,1-hi]indazole-7-carboxylic acid (100)

0.51 g (1.55 mmol) of the compound (99) obtained in Example 16 was added to 5 ml of a mixture solution of concentrated hydrochloric acid and acetic acid (in a volumetic ratio of 1:4), and this solution was heated at reflux for 8 hours. After air-cooled, the solution was diluted with 100 ml of water, and the deposited crystals were filtered and washed consecutively with water, ethanol and ether to obtain 200 mg of the subject compound (100) in a 51% yield. The results of the analysis of this compound were as follows:
Colorless needles:
Melting point: 232°-237° C. (decomp.)
$^1$H-NMR (DMSO-d$_6$)
4.99 (s, 2H), 8.02 (dd, J=7.0 Hz, 3.3 Hz, 1H), 8.96 (s, 1H)

EXAMPLE 18

4,5-Difluoro-2,3-dihydro-1-methyl-7-oxo-1H, 7H-pyrido[3,2,1ij]cinnoline-8-carboxylic acid BF$_2$ chelate (107)

2.78 g of compound (8) obtained in Example 3 was suspended in 30 ml of ether, to which 80 ml of boron trifluoride-ether complex was added over 5 minutes while cooling on ice. Stirring was continued overnight, and precipitated solid was collected by filtration. 3.07 g of a title compound (107) was obtained (yield: 94%).
Colorless powder
Melting point: 285° C. (decomp.)
$^1$H-NMR(DMSO-d$_6$)
3.01 (s, 1H), 3.25, 3.64 (each brs, each 2H), 8.49 (dd, J=9.0Hz, 9.0Hz 1H), 9.38 (s, 1H)

EXAMPLE 19 (METHOD F)

(1)

4-((3R)-Methylpiperazin-1-yl)-5-fluoro-2,3-dihydro-1-methyl-7-oxo-1H, 7H-pyrido[3,2,1-ij]cinnoline-8-carboxylic acid (108)

2 ml of dimethylsulfoxide was added to 164 mg (0.5 mmol) of compound (107), 173 mg (1 mmol) of (2R)-methylpiperazine.2HCl and 0.36 ml (2.5 mmol) of triethylamine, and stirred overnight at room temperature. Ether was added thereto, supernatant was removed, and ethanol and ether were added to the residue for collecting crystals. The crystals were washed with ether, and added with 20 ml of aqueous 80% methanol solution and 1 ml of triethylamine, and heated at reflux for 3 hours. After allowing it to cool down, condensation under reduced pressure and addition with ethanol were carried out for filtrating solid. It was washed with ether to obtain 105 mg of the title compound (108) (yield: 58%).
Slightly yellowish powder:
Melting point: >210° C. (decomp.)
$^1$H-NMR (DMSO-d$_6$)
1.27 (d, J=6.4Hz, 3H), 2.91 (s, 3H), 3.09-3.28 (In, 4H), 3.29-3.57 (m, 7H), 7.95 (d, J=12.7Hz, 1H), 8.77(s, 1H)

(2)-(11)

General procedures of Example 19 (1) were followed. Compounds (109)-(118) in Tables 22 to 23 were obtained.

TABLE 22

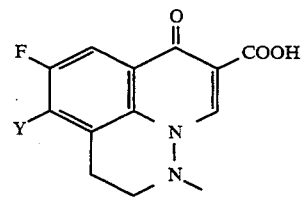

| Example No. | Compound No. | Y | Property | Melting point (°C.) | $^1$H-NMR | Preparing method |
|---|---|---|---|---|---|---|
| 19(2) | 109 | MeN⟩N— (1R, 4R) | Slightly yellowish powder | 168–172 decomp. | DMSO-d$_6$ 2.22, 2.37(each brs, each 1H), 2.88, 2.91(each s, each 3H), 3.19–3.61(m, 6H), 3.66–3.92(m, 2H), 4.39, 4.62(each brs, each 1H), 7.89(d, J=13.5Hz, 1H), 8.69(s, 1H) | method F |
| 19(3) | 110 | HN⟩N— CH$_2$F | Slightly yellowish powder | 228–230 decomp. | DMSO-d$_6$ 2.90(s, 3H), 2.98–3.41(m, 9H), 3.47(brs, 2H, 4.42(d, J=47.4Hz, 2H), 7.91(d, J=12.5Hz, 1H), 8.74(s, 1H) | method F |

TABLE 22-continued

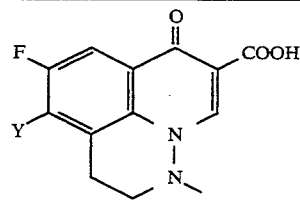

| Example No. | Compound No. | Y | Property | Melting point (°C.) | $^1$H-NMR | Preparing method |
|---|---|---|---|---|---|---|
| 19(4) | 111 | HN⟨N-CH₂F⟩ | Slightly yellowish powder | 221–223 decomp. | DMSO-$d_6$ 2.90(s, 3H), 2.98–3.41(m, 9H), 3.47(brs, 2H), 4.42(d, J=47.4Hz, 2H), 7.91(d, J=12.5Hz, 1H), 8.74(s, 1H) | method F |
| 19(5) | 112 | O⟨N-⟩CH₂NH₂·HCl | Yellowish powder | >210 decomp. | DMSO-$d_6$ 2.89(s, 3H), 2.98–3.64(m, 11H), 3.65–3.83(m, 1H), 3.84–4.07(m, 1H), 7.94(d, J=16.2Hz, 1H), 8.21(brs, 1H), 8.78(s, 1H) | method F |
| 19(6) | 113 | N⟨⟩N | Slightly yellowish powder | >195 decomp. | DMSO-$d_6$ 1.41(brs, 1H), 1.77(brs, 3H), 2.06–2.48(m, 2H), 2.93(s, 3H), 3.07(brs, 5H), 3.19–3.57(m, 6H), 7.92(d, J=13.5Hz, 1H), 8.73(s, 1H) | method F |

TABLE 23

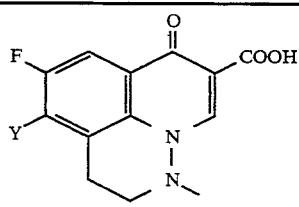

| Example No. | Compound No. | Y | Property | Melting point (°C.) | $^1$H-NMR | Preparing method |
|---|---|---|---|---|---|---|
| 19(7) | 114 | ▷-N⟨⟩N— | Slightly yellowish powder | >210 decomp. | CDCl$_3$ 0.45–0.56(m, 4H), 1.68–1.78(m, 1H), 2.78(brs, 4H), 2.91(s, 3H), 3.10(t, J=5.9Hz, 2H), 3.24(brs, 4H), 3.48(t, J=5.9Hz, 2H), 8.02(d, J=12.2Hz, 1H), 8.82(s, 1H) | method F |
| 19(8) | 115 | HN⟨N-⟩ | Yellowish powder | >210 decomp. | DMSO-$d_6$ 1.27(d, J=6.4Hz, 3H), 2.91(s, 3H), 3.09–3.28(m, 4H), 3.29–3.57(m, 7H), 7.95(d, J=12.7Hz, 1H), 8.77(s, 1H) | method F |
| 19(9) | 116 | HN⟨N-⟩ | Slightly yellowish powder | >215 decomp. | DMSO-$d_6$ 1.37(s, 6H), 2.90(s, 3H), 3.14(brs, 2H), 3.21(brs, 4H), 3.49(brs, 2H), 7.96(d, J=12.7Hz, 1H), 8.77(s, 1H) | method F |
| 19(10) | 117 | MeN⟨⟩N— | Colorless powder | >225 decomp. | DMSO-$d_6$ 2.24(brs, 4H), 2.75(s, 3H), 2.89(s, 3H), 3.21(brs, 2H), 3.51(brs, 2H), 3.60–3.75(m, 2H), 3.97(brs, 2H), 7.98(d, J=12.2Hz, 1H), 8.79(s, 1H) | method F |

TABLE 23-continued

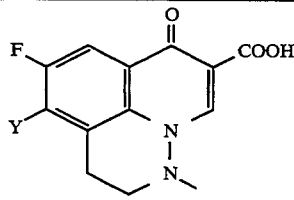

| Example No. | Compound No. | Y | Property | Melting point (°C.) | ¹H-NMR | Preparing method |
|---|---|---|---|---|---|---|
| 19(11) | 118 | HN⟨pyrrolidine with F⟩N— | Yellowish powder | >194 decomp. | DMSO-$d_6$ 2.68–2.78(m, 1H), 2.89(s, 3H), 3.01–4.13(m, 11H), 4.67–5.09(m, 1H), 7.94(d, J=13.5Hz, 1H), 8.78(s, 1H) | method F |

EXAMPLE 20

5-Fluoro-4-(pyrrolidin-1-yl)-2,3-dihydro-1-formyl-7-oxo-1H, 7H-pyrido[3,2,1-ij]cinnoline-8-carboxylic acid (119)

315 mg of compound (102) obtained in Example 4 (21) was added to 1.17 g of formic acid and heated at 100° C. for 4 hours. After allowing it to cool down, 10 ml of ether was added thereto and stirred over 5 minutes. Solid matters produced were filtered out and washed with ether. 250 mg of a title compound (119) was obtained.

Slightly-brown needles
Melting point: 238°–243° C.
¹H-NMR(DMSO-$d_6$)
1.91 (brs, 4H), 2.83–3.15 (m, 2H), 3.49 (s, 4H), 3.65–3.85 (m, 1H), 7.83 (d, J=13.9Hz, 1H), 8.57 (s, 1H), 8.65 (s, 1H)

EXAMPLE 21

1-Acetyl-5-fluoro-4-(pyrrolidin-1-yl)-2,3-dihydro-7-oxo-1H, 7H-pyrido[3,2,1-ij]cinnoline-8-carboxylic acid (120)

100 mg of compound (102) obtained in Example 4 (21) was dissolved in 1 ml of acetic acid and 1 ml of acetic anhydride, and heated at 110° C. for 3 hours. The mixture was allowed to cool down. Produced solid matters were filtered out and washed with ether. 80 mg of a title compound (120) was obtained.

Slightly-brown powder:
Melting point: 278°–283° C.
¹H-NMR(DMSO-$d_6$)
1.90 (brs, 4H), 2.38 (s, 3H), 2.80–3.90 (m, 8H), 7.80 (d, J=14.0Hz, 1H), 8.57 (s,1H)

EXAMPLE 22

Methyl 4-(cis (−)-3-amino-4-methylpyrrolidine-1-yl)-5-fluoro-2,3-dihydro-1-methyl-7-oxo-1H,7H-pyrido[3,2,1-ij]cinnoline-8-carboxylate (121)

2 ml of thionyl chloride was added to 20 ml of methanol while cooling on ice, and then this solution was stirred at room temperature. 358 mg of the compound (30) obtained in Example 5 was added to the solvent, and the solution was heated at reflux for 8 hours. The solvent was removed and 40 ml of chloroform and 20 ml of water were added to the residue. The solution was alkalized with sodium hydrogen carbonate, and the organic layer was dried over magnesium sulfate. The solvent was removed by distillation. To the residue, ether was added and then ethyl acetate was added to form crystals. They were filtered off and washed with ethyl acetate in this order to obtain 270 mg of a title compound (121) (yield: 72%).

Colorless needles:
Melting point: 199°–202° C. (decomp.)
¹H-NMR (CDCl$_3$) 1.13 (d, J=6.9 Hz, 3H), 1.74 (brs, 2H), 2.36–2.48 (m, 1H), 2.82–3.06 (m, 2H), 2.87 (s, 3H), 3.20–3.57 (m, 6H), 3.80–3.97 (m, 1H), 3.91 (s, 3H), 7.96 (d, J=13.9 Hz, 1H), 8.56 (s, 1H)

EXAMPLE 23

Methyl 4-(Pyrrolidin-1-yl)-5-fluoro-2,3-dihydro-1-methyl-7-oxo-1H,7H-pyrido-[3,2,1-ij]cinnoline-8-carboxylate (122)

2.92 g of the compound (6) obtained in Example 2 (1), 1.07 g of pyrrolidine and 2.25 g of 1,8-diazabicyclo[5.4.0]-7-undecene were added to 20 ml of N,N-dimethylformamide, and the solution was heated at 80° C. for 12 hours. The solvent was removed by distillation, and 100 ml of chloroform was added to the residue. After washing with water, the organic layer was separated from the solution. After drying over magnesium sulfate, the solvent was removed by distillation. To the residue, 50 ml of isopropyl ether was added, and the solid was filtered to obtain 2.60 g of the subject compound (122).

Slightly yellowish powder:
Melting point: 203°–206° C.
¹H-NMR (CDCl$_3$)
1.99 (s, 4H), 2.87 (s, 3H), 2.95 (brs, 2H), 3.30–3.55 (m, 6H), 3.92 (s, 3H), 7.99 (d, J=14.0 Hz, 1H), 8.57 (s, 1H)

REFERENCE EXAMPLE 5

4-t-Butylamino-3-fluoro-2-(2-hydroxyethyl)nitrobenzene (123)

30.5 g (150 mmol) of 3,4-difluoro-2-(2-hydroxyethyl)-nitrobenzene and 90 ml (900 mmol) of t-butylamine were added to 150 ml of dimethylsulfoxide and 25 ml of toluene, and the solution was heated at reflux for 8.5 hours. After air-cooling, the solution was poured into 1500 ml of water, and the deposited crystals were filtered. They were dissolved in 500 ml of chloroform, and after drying over magnesium sulfate, the solvent was removed by distillation. The residue was crystallized with n-hexane, and the crystals were filtered off to obtain 35.5 g of the subject compound (123) in a 93% yield.

REFERENCE EXAMPLE 6

4-Amino-3-fluoro-2-(2-hydroxyethyl)nitrobenzene (124)

11 g of the compound (123) obtained in Comparative Example 5 was added to 200 ml of concentrated hydrochloric acid, and the solution heated at reflux for 2.5 hours. After air-cooling, the solution was extracted with 500 ml of ethyl acetate four times, and the extract was washed with aqueous 10% sodium hydrogen carbonate solution. After drying over magnesium sulfate, the solvent was removed by distillation. The residue was crystallized with n-hexane, and the crystals were filtered to obtain 8.33 g of the subject compound (124) in a 97% yield.

REFERENCE EXAMPLE 7

4-Chloro-3-fluoro-2-(2-hydroxyethyl)nitrobenzene (125)

7.33 g (37 mmol) of the compound (124) obtained in Reference Example 6 was added to 60 ml of 6N hydrochloric acid, and while cooling on ice, 15 ml of aqueous solution containing 2.95 g (43 mmol) of sodium nitrite was dropped to the solution through 5 minutes. The solution was stirred for 30 minutes as was. Then, 20 ml of concentrated hydrochloric acid and 20 ml of acetic acid were added to the solution, and the solution was stirred for 1 hour. While cooling on ice, 35 ml of concentrated hydrochloric acid solution containing 6.20 g (63 mmol) of cuprous chloride was dropped to the solution through 40 minutes, and the solution was stirred for 3 hours as was. The solution was extracted with 300 ml of ethyl acetate, and after drying over magnesium sulfate, the solvent was removed by distillation. The residue was separated by the column chromatography (silica gel 100 g, eluent solvent; chloroform: methanol=50:1) to obtain 6.69 g of the subject compound (125) in a 83% yield.

REFERENCE EXAMPLE 8

4-Chloro-3-fluoro-2-(2-hydroxyethyl)aniline (126)

4.8 g of iron powder and 0.45 ml of concentrated hydrochloric acid were added to a mixture solvent of 50 ml of water and 10 ml of ethanol, and the solution was heated at 80°–90° C. 6.69 g (31 mmol) of 4-chloro-3-fluoro-2-(2-hydroxyethyl)nitrobenzene was added to the solution through 10 minutes, and the solution was heated for 1 hour as was. After air-cooling, 100 ml of ethyl acetate was added to the solution, and insoluble matter was filtered. The organic layer was separated and was washed with aqueous 10% sodium hydrogen carbonate solution. After drying over magnesium sulfate, the solvent was removed by distillation to obtain 4.68 g of the subject compound (126) in a 80% yield.

REFERENCE EXAMPLE 9

Diethyl {4-Chloro-3-fluoro-2-(2-hydroxyethyl)anilino}methylenemalonate (127)

To 4.68 g (25 mmol) of the compound (126) obtained above, 5.36 (25 mmol) of diethyl ethoxymethylenemalonate was added, and the solution was heated at 120° C. for 2 hours. Then, ethanol was removed from the solution by distillation, and crystals obtained were dispersed in n-hexane and filtered to obtain 8.55 g of the subject compound (127) in a 95% yield.

REFERENCE EXAMPLE 10

Diethyl {4-Chloro-3-fluoro-2-(2-t-butyldimethylsilyloxyethyl)anilino}methylenemalonate (128)

8.55 g (24 mmol) of the compound (127) obtained above and 1.70 g (25 mmol) of imidazole were added to 50 ml of methylene chloride, and 10 ml of methylene chloride solution containing 3.77 g (25 mmol) of t-butyldimethylchlorosilane was dropped to the solution through 10 minutes. After the solution was stirred at room temperature for 1 hour, 0.30 g of imidazole and 0.67 g of t-butyl dimethylchlorosilane were further added to the solution, and the solution was stirred for 1 hour. The solution was washed with 50 ml of water, and after drying over magnesium sulfate, the solvent was removed by distillation. The residue was separated by the column chromatography (silica gel 200 g, eluent solvent; chloroform) to obtain 9.35 g of the oily subject compound (128) in a 82% yield.

REFERENCE EXAMPLE 11

Ethyl 6-Chloro-7-fluoro-8-(2-t-butyldimethylsilyloxyethyl) -4-hydroxyquinoline-3-carboxylate (129)

To 8.35 g (17.1 mmol) of the compound (128), 80 ml of Dowtherm A (Trademark) was added, and the solution was heated until a fraction of 200° C. was taken out. The solution was further heated at reflux for 5 minutes. After air-cooling, 50 ml of ether was added to the solution, and the crystals were filtered off to obtain 5.62 g of the subject compound (129) in a 74% yield.

REFERENCE EXAMPLE 12

Ethyl 6-Chloro-7-fluoro-8-(2-hydroxyethyl)-4-hydroxyquinoline-3-carboxylate (130)

5.62 g (13 mmol) of the compound (129) obtained above was added in a mixture solvent of 100 ml of chloroform and 100 ml of methanol, and 15 ml of 4N hydrochloric acid solution in dioxane was added to the solution. After stirring at room temperature for 30 minutes, the solvent was removed from the solution by distillation. Crystals obtained were dispersed in ethanol and filtrated. They were washed with ethanol and ether in this order to obtain 3.70 g of the subject compound (130) in a 90% yield.

REFERENCE EXAMPLE 13

Ethyl 1-Amino-6-chloro-7-fluoro-8-(2-hydroxyethyl)-1,4-dihydro-4-oxoquinoline-3-carboxylate (131)

4 g (12.8 mmol) of the compound (130) obtained above and 3.53 g (25.6 mmol) of anhydrous potassium carbonate were added to 70 ml of dimethylformamide, and the solution was stirred at room temperature for 2 hours. 7.29 g (25.5 mmol) of ethyl o-(mesitylenesulfonyl)acetohydoxamate was added to 10 ml of dioxane, and while cooling on ice, 2.6 ml of 70% perchloric acid was dropped to the solution below 10° C. through 15 minutes. The solution was stirred for 20 minutes as was, and then added to 50 ml of ice/water. Crystals were filtered off and washed on ice/water and then dissolved in 50 ml of methylene chloride. The organic layer was separated from the solution, and after drying over magnesium sulfate, while cooling on ice, the solution was dropped to the previously prepared reaction solution of dimethylformamide through 5 minutes. The solution was stirred for 1 hour as was, and 100 ml of water was added to the solution. Crystals were filtered off and washed with ethanol and ether in this order to obtain 2.08 g of the subject compound (131) in a 50% yield.

EXAMPLE 24

Ethyl 5-Chloro-4-fluoro-2,3-dihydro-7-oxo-1H,7H-pyrido[3,2,1-ij]cinnoline-8-carboxylate (132)

2.08 g (6.3 mmol) of the compound (131) obtained in Reference Example 13 and 2.62 g (10 mmol) of triphenylphosphine were added to 50 ml of tetrahydrofuran, and 50 ml of tetrahydrofuran solution containing 1.74 g (10 mmol) of diethyl azodicarboxylate was dropped to the solution at room temperature through 2 hours. After 20 minutes, the solvent was removed by distillation. Solids obtained were dispersed in ethanol and filtered off and washed with ethanol and ether in this order to obtain 1.69 g of the subject compound (132) in a 86% yield.

Colorless powder:
Melting point: 235° C. (decomp.)
$^1$H-NMR (DMSO-$d_6$)
1.28 (t, J=7.0 Hz, 3H), 2.93 (brs, 2H), 3.41 (dr, J=6.2 Hz, 5.9 Hz, 2H), 4.21 (q, J=7.0 Hz, 2H), 6.85 (t, J=6.9 Hz, 1H), 8.09 (d, J=8.1 Hz, 1H), 8.42 (s, 1H)

EXAMPLE 25

Methyl 5-Chloro-4-fluoro-2,3-dihydro-1-methyl-7-oxo -1H,7H-pyrido[3,2,1-ij]cinnoline-8-carboxylate (133)

To 1.69 g (5.5 mmol) of the compound (132) obtained in Example 24, 10 ml (109 mmol) of dimethylsulfate was added, and the solution was heated at 120° C. for 4.5 hours. After air-cooling, the solution was added to 90 ml of ice/water to which 15 g (109 mmol) of anhydrous potassium carbonate was added, and the solution was stirred for 1 hour. The solution was extracted with 200 ml of chloroform, and after drying over magnesium sulfate, the solvent was removed by distillation. The residue was separated by the column chromatography (silica gel 60g, eluent solvent; chloroform: methanol=100:1) to obtain 600 mg of the subject compound (133) in a 36% yield.

Slightly yellowish powder:
Melting point: 199° C. (decomp.)
$^1$H-NMR (CDCl$_3$)
2.86 (s, 3H), 3.07 (t, J=5.8 Hz, 2H), 3.49 (t, J=5.9 Hz, 2H), 3.92 (s, 3H), 8.42 (d, J=8.0 Hz, 1H), 8.60 (s, 1H)

EXAMPLE 26

5-Chloro-4-fluoro-2,3-dihydro-1-methyl-7-oxo-1H,7H -pyrido[3,2,1-ij]cinnoline-8-carboxylic acid (134)

To 600 mg (1.9 mmol) of the compound (133) obtained in Example 25, 5 ml of concentrated hydrochloric acid and 20 ml of acetic acid were added, and the solution was heated at reflux for 2 hours. After air-cooling, 20 ml of water was added to the solution, and solids were filtered off and washed with ethanol and ether in this order to obtain 461 mg of the subject compound (134) in a 80% yield.

Slightly yellowish powder:
Melting point: 223°–225° C.
$^1$H-NMR (DMSO-$d_6$)
2.88 (s, 3H), 3.11 (brs, 2H), 3.53 (t, J=5.5 Hz, 2H), 8.33 (d, J=7.3 Hz, 1H), 8.83 (s, 1H)

EXAMPLE 27

5-Chloro-4-fluoro-2,3-dihydro-1-methyl-7-oxo-1H,7H-pyrido[3,2,1-ij]cinnoline-8-carboxylic acid BF$_2$ chelate (135)

300 mg (1 mmol) of the compound (134) obtained in Example 26 was added to 6 ml of ether, and 9 ml of boron trifluoride-ether complex was added to the solution. The solution was stirred at room temperature for 4 hours. The deposited solids were filtered off and washed with ether to obtain the subject compound (135) in a 63% yield.

Colorless powder
Melting point: 275° C. (decomp.)
$^1$H-NMR (DMSO-$d_6$)
3.01 (s, 3H), 3.23 (t, J=4.9 Hz, 2H), 3.63 (t, J=6.3 Hz, 2H), 8.65 (d, J=7.8 Hz, 1H), 9.41 (s, 1H)

EXAMPLE 28

5-Chloro-4-(1-pyrrolidinyl)-2,3-dihydro-1-methyl-7-oxo -1H,7H-pyrido[3,2,1-ij]cinnoline-8-carboxylic acid (136)

100 mg (0.29 mmol) of the compound (135) obtained in Example 27 was 0.5 ml of dimethylsulfoxide, and 55 mg (0.64 mmol) of pyrrolidine was added to the solution. The solution was stirred for 24 hours at room temperature. Then, 1 ml of ether and 2 ml of ethanol were added to the solution to crystallize. Crystals were filtered off and washed with ethanol and ether in this order to obtain 80 mg of the crystals. To the obtained crystals, 5 ml of 80% methanol and 0.5 ml of triethylamine were added, and the solution was heated at reflux for 4 hours. After the solvent was removed by distillation, the crystals were dispersed in ethanol and filtered off and were washed with ethanol and ether in this order to obtain 55 mg of the subject compound (136) in a 52% yield.

Slightly yellowish prisms:
Melting point: 244° C. (decomp.)
$^1$H-NMR (DMSO-$d_6$)
2.00 (brs, 4H), 2.90 (s, 3H), 3.01 (brs, 2H), 3.41 (brs, 4H), 3.47 (brs, 2H), 8.20 (s, 1H), 8,75 (s, 1H)

REFERENCE EXAMPLE 14

2-Chloro-6-nitrophenylacetic acid (137)

8.08 g (202 mmol) of 60% sodium hydride was added to 30 ml of tetrahydrofuran, and while cooling on a freezing mixture, 60 ml of tetrahydrofuran solution containing 32.0 g (200 mmol) of diethyl malonate was dropped to the solution below 20° C. over 1 hour, then the solution was stirred for 1 hour. 60 ml of Tetrahydrofuran solution containing 19.2 g (100 mmol) of 2,3-dichloronitrobenzene was dropped to the solution below 10° C. over 10 minutes. After the solution was stirred for 3.5 hours at room temperature, it was heated at reflux for 48 hours. 18 ml of acetic acid was added to the solution, and the solvent was removed by distillation. The solution was extracted over 200 ml of chloroform, and after drying over magnesium sulfate, the solvent was removed by distillation. To the residue, 30 ml of 4N hydrochloric acid and 25 ml of acetic acid were added, and the solution was heated at reflux for 24 hours. After air-cooling, the deposited crystals were filtered off and washed with water, and they were dissolved in 250 ml of ethyl acetate. The filtrate was extracted with 250 ml of ethyl acetate. The organic layers were combined, and after drying over magnesium sulfate, the solvent was removed by distillation. The crystals were washed with n-hexane to obtain 6.78 g of the subject compound (137) in a 31% yield.

REFERENCE EXAMPLE 15

3-Chloro-2-(2-hydroxyethyl)nitrobenzene (138)

2.26 g (59.8 mmol) of sodium borohydride was added to 7 ml of tetrahydrofuran, and while cooling on ice, 15 ml of tetrahydrofuran solution containing 6.78 g (31.5 mmol) of the compound (137) obtained above was dropped to the solution through 20 minutes. Then, 15 ml of tetrahydrofuran solution containing 10 ml of borontrifluoride-ether complex was dropped to the solution through 10 minutes, and after stirring for 30 minutes as was, the solution was stirred for 1 hour at room temperature. To 130 ml of water containing 9.6 g of sodium hydrogen carbonate and 170 ml of methylene chloride, the reaction solution was added slowly, and the obtained solution was stirred overnight at room temperature. The organic layer was separated, and after drying over magnesium sulfate, the solvent was removed by distillation. To the residue, n-hexane was added to crystallize, and the crystals were filtered off and washed with n-hexane to obtain 5.43 g of the subject compound (138) in a 86% yield.

REFERENCE EXAMPLE 16

3-Chloro-2-(2-hydroxyethyl)aniline (139)

4.5 g of iron powder and 0.45 ml of concentrated hydrochloric acid were added to a mixture solvent of 50 ml of water and 10 ml of ethanol, and the solution was heated at 80°-90° C. 5.43 g of the compound (138) obtained above was added to the solution through 10 minutes, and the solution was heated for 30 minutes as was. After air-cooling, 100 ml of ethyl acetate was added to the solution, and insoluble matter was filtered. The organic layer was separated from the solution and was washed with 10% sodium hydrogen carbonate solution, and after drying over magnesium sulfate, the solvent was removed by distillation. The crystals obtained were washed with n-hexane to obtain 4.40 g of the subject compound (139) in a 95% yield.

REFERENCE EXAMPLE 17

Diethyl {3-Chloro-2-(2-hydroxyethyl)anilino}methylene malonate (140)

To 4.40 g (25.6 mmol) of the compound (139) obtained above, 5.55 g (25.6 mmol) of diethyl ethoxymethylenemalonate was added, and the solution was heated at 120° C. for 4 hours. After air-cooling, crystals were dispersed in n-hexane and filtered off to obtain 8.52 g of the subject compound (140) in a 97% yield.

REFERENCE EXAMPLE 18

Diethyl {3-Chloro-2-(2-t-butyldimethylsilyloxyethyl)anilino} methylene malonate (141)

8.52 g (25 mmol) of the compound (140) and 1.77 (26 mmol) of imidazole were added to 50 ml of methylene chloride, and 10 ml of methylene chloride containing 3.92 (26 mmol) of t-butyldimethylchlorosilane was dropped to the solution through 10 minutes. The solution was stirred for 1 hour at room temperature. 0.30 g of imidazole and 0.67 g of t-butyldimethylchlorosilane were supplemented to the solution, and the solution was stirred for 1 hour. The solution was washed with 50 ml of water, and after drying over magnesium sulfate, the solvent was removed by distillation. The solid matter was separated by column chromatography (silica gel 200 g, eluent solvent; chloroform) to obtain 11.5 g of oily subject compound (141).

REFERENCE EXAMPLE 19

Ethyl 7-Chloro-8-(2-hydroxyethyl)-4-hydroxyquinoline-3-carboxylate (142)

To 11 g of the compound (141) obtained above, 80 ml of Dowtherm A (Trademark) was added, and the solution was heated until a fraction of 200° C. was taken out. Further, the solution was heated at reflux for 20 minutes. After air-cooling, 10 ml of concentrated hydrochloric acid was added to the solution. After stirring for 80 minutes at room temperature, the deposited crystals were filtered off and washed with ethanol and ether in this order to obtain 4.96 g of the subject compound (142) in a 70% yield.

REFERENCE EXAMPLE 20

Ethyl 1-Amino-7-chloro-8-(2-hydroxyethyl)-1,4-dihydro-4-oxoquinoline-8-carboxylate (148)

4.96 g (16.8 mmol) of the compound (140) obtained above and 4.65 g of anhydrous potassium carbonate were added to 90 ml of N,N-dimethylformamide, and the solution was stirred for 2 hours at room temperature. 9.60 g of ethyl o-(mesitylene-sulfonyl)acetohydroxamate was added to 13 ml of dioxane, and while cooling on ice, 3.4 ml of 70% perchloric acid was dropped below 10° C. through 15 minutes. The solution was stirred for 20 minutes as was, and added to 50 ml of ice/water. Crystals were filtered off and washed with ice/water and dissolved in 50 ml of methylene chloride. The organic layer was separated and was dropped to the previously prepared reaction solution of the dimethylformamide through 5 minutes, while cooling on ice, after drying over magnesium sulfate. The solution was stirred for 1 hour as was, and 100 ml of water was added to the solution. Crystals were filtered off and washed with ethanol and ether in this order to obtain 0.69 g of the subject compound (143) in a 13% yield.

EXAMPLE 29

Ethyl 4-Chloro-2,3-dihydro-7-oxo-1H,7H-pyrido[3,2,1-ij]cinnoline-8-carboxylate (144)

1.02 g (3.3 mmol) of the compound (143) obtained in Reference Example 20 and 1.37 g (5.2 mmol) of triphenylphosphine were added to 25 ml of tetrahydrofuran, and 25 ml of tetrahydrofuran solution containing 0.91 g (5.2 mmol) of diethyl azodicarboxylate was dropped to the solution at room temperature through 1 hour. After 20 minutes, the solvent was removed by distillation. The solids obtained were dispersed in ethanol and filtered off and then washed with ethanol and ether in this order to obtain 0.81 g of the subject compound (144) in a 84% yield.

Colorless powder:
Melting point: 210.5°–213° C. (decomp.)
$^1$H-NMR (DMSO-d$_6$)
1.27 (t, J=7.3 Hz, 3H), 2.93 (t, J=5.9Hz, 2H), 3.44 (dt, J=2.9 Hz, 6.2 Hz, 2H), 4.21 (q, J=7.0 Hz, 2H), 6.84 (t, J=7.3 Hz, 1H), 7.55 (d, J=8.8 Hz, 1H), 8.05 (d, J=8.4 Hz, 1H), 8.44 (s, 1H)

EXAMPLE 30

Methyl 4-Chloro-2,3-dihydro-1-methyl-7-oxo-1H,7H-pyrido-[3,2,1-ij]cinnoline-8-carboxylate (145)

To 810 mg (2.8 mmol) of the compound (144) obtained in Example 29, 5 ml (55 mmol) of dimethyl sulfate was added, and the solution was heated for at 120° C. for 5.5 hours. After air-cooling, to 45 ml of ice/water containing 7.5 g (55 mmol) of anhydrous potassium carbonate, was added the solution, and was stirred for 1 hour. The solution was extracted with 50 ml of chloroform, and after drying over magnesium sulfate, the solvent was removed by distillation. The residue was separated by the column chromatography (silica gel 8 g, eluent solvent; chloroform: methanol=100:1) to obtain 371 mg of the subject compound (145) in a 46% yield.

Colorless powder:
Melting point: 225° C. (decomp.)
$^1$H-NMR (CDCl$_3$)
2.85 (s, 3H), 3.09 (t, J=6.2 Hz, 2H), 3.51 (t, J=5.9 Hz, 2H), 3.93 (s, 3H), 7.45, 8.33 (each d, each J=8.8 Hz, each 1H), 8.62 (s, 1H)

EXAMPLE 31

4-Chloro-2,3-dihydro-1-methyl-7-oxo-1H,7H-pyrido[3,2,1-ij]cinnoline-8-carboxylic acid (146)

To 370 mg (1.3 mmol) of the compound (145) obtained in Example 30, 2 ml of concentrated hydrochloric acid and 10 ml of acetic acid were added, and the solution was heated at reflux for 2 hours. The solvent was removed by distillation. Crystals were dispersed in ethanol and filtered and washed with ethanol and ether in this order to obtain 270 mg of the subject compound (146) in a 77% yield.

Colorless prisms:
Melting point: >240° C. (decomp.)
$^1$H-NMR (DMSO-d$_6$)
2.88 (s, 3H), 3.10, 3.57 (each brs, each 2H), 7.77, 8.25 (each d, each J=8.4 Hz, each 1H), 8.81 (s, 1H)

EXAMPLE 32

4-Chloro-2,3-dihydro-1-methyl-7-oxo-1H, 7H-pyrido[3,2,1-ij]cinnoline-8-carboxylic acid BF$_2$ chelate (147)

240 mg (0.86 mmol) of the compound (146) obtained in Example 31 was added to 6 ml of ether, and 9 ml of borontrifluoride-ether complex was added to the solution. The solution was stirred overnight at room temperature. The deposited crystals were filtered off and washed on ether to obtain 266 mg of the subject compound (147) in a 94% yield.

Colorless powder:
Melting point: >285° C. (decomp.)
$^1$H-NMR (DMSO-d$_6$)
3.02 (s, 3H), 3.23, 3.67 (each brs, each 2H), 8.06, 8.46 (each d, each J=9.4 Hz, each 1H), 9.37 (s, 1H)

REFERENCE EXAMPLE 21

3,4-Difluoro-2-(2-oxopropyl)nitrobenzene (148)

12.1 g (303 mmol) of 60% sodium hydride was added to 45 ml of tetrahydrofuran, and while cooling with a freezing mixture, 90 ml of tetrahydrofuran containing 39.0 g (300 mmol) of ethyl acetoacetate was dropped to the solution below 20° C. through 30 minutes. After the solution was stirred for 1 hour as was, 90 ml of tetrahydrofuran solution containing 26.6 g (150 mmol) of 2,3,4-trifluoronitrobenzene was dropped to the solution below 10° C. through 30 minutes, and the solution was stirred overnight at room temperature. 27 ml of acetic acid was added to the solution, and the solvent was removed by distillation. The solution was extracted with 500 ml of chloroform, and after drying over magnesium sulfate, the solvent was removed by distillation. 30 ml of 4N hydrochloric acid and 25 ml of acetic acid were added to the solution, and the solution was heated at reflux for 24 hours. 550 ml of concentrated hydrochloric acid and 550 ml of acetic acid were added to the solution, and the solution was heated at reflux for 16 hours. After air-cooling, the solution was extracted with 1 l of chloroform and was washed with 500 ml of water two times. The solution was further washed with 300 ml of aqueous saturated sodium hydrogen carbonate solution two times, and after drying over magnesium sulfate, the solvent was removed by distillation. The residue was separated by the column chromatography (silica gel 300 g, eluent solvent; chloroform: n-hexane=1:3) to obtain 31.2 g of the subject compound (148) in a 90% yield.

REFERENCE EXAMPLE 22

3,4-Difluoro-2-(2-hydroxypropyl)nitrobenzene (149)

31.2 g (145 mmol) of the compound (148) obtained above was added to 500 ml of methanol, and while cooling on ice, 6.04 g (160 mmol) of sodium borohydride was added to the solution through 5 minutes. After the solution was stirred for 30 minutes as was, the solution was stirred overnight at room temperature. 100 ml of 4N hydrochloric acid was added slowly to the solution and the solution was stirred for 30 minutes at room temperature. Then, the solvent was removed by distillation. The solution was extracted with 400 ml of chloroform, and after drying over magnesium sulfate, the solvent was removed by distillation to obtain 27.7 g of the subject compound (149) in a 89% yield.

REFERENCE EXAMPLE 23

3,4-Difluoro-2-(2-hydroxypropyl)aniline (150)

23 g of iron powder and 2.3 ml of concentrated hydrochloric acid were added to a mixture solvent of 250 ml of water and 50 ml of ethanol, and the solution was heated at 80°–90° C. 27.7 g (128 mmol) of the compound (149) obtained above was added to the solution through 30 minutes, and the solution was heated for 40 minutes as was. After air-cooling, 200 ml of ethyl acetate was added to the solution, and insoluble matter was filtered. The organic layer was separated and the aqueous solution was extracted with 200 ml of ethyl acetate. The organic layers were combined and after drying over magnesium sulfate, the solvent was removed by distillation to obtain 21.1 g of the subject compound (150) in a 89% yield.

REFERENCE EXAMPLE 24

Diethyl {3,4-Difluoro-2-(2-hydroxypropyl)anilino}methylenemalonate (151)

To 21.1 g (113 mmol) of the compound (150) obtained above, 24.4 g (113 mmol) of diethyl ethoxymethylenemalonate was added, and the solution was heated at 120° C. for 3 hours. After air-cooling, crystals deposited were dispersed in n-hexane and filtered off to obtain 25.0 g of the subject compound (151) in a 62% yield.

REFERENCE EXAMPLE 25

Diethyl {3,4-Difluoro-2-(2-t-butyldimethylsilyloxypropyl)anilino}methylenemalonate (152)

14.2 g (40 mmol) of the compound (151) and 3.27 g (48 mmol) of imidazole were added to 100 ml of methylene chloride, and 20 ml of methylene chloride containing 7.23 g (48 mmol) of t-butyldimethylchlorosilane was dropped to the solution through 30 minutes. After the solution was stirred for 2.5 hours at room temperature, it was heated at reflux for 2 hours. 3.27 g of imidazole and 7.23 g of t-butyldimethylchlorosilane were supplemented to the solution, and the solution was heated at reflux for 11 hours. The solution was washed 100 ml of water, 50 ml of aqueous citric acid solution and 50 ml of saturated aqueous sodium hydrogen carbonate solution in this order, and after drying over magnesium sulfate, the solvent was removed by distillation. The solid matter was separated by column chromatography (silica gel 600 g, eluent solvent; chloroform:n-hexane=1:1) to obtain 14.2 g of an oily subject compound (152) in a 76% yield.

REFERENCE EXAMPLE 26

Ethyl 6,7-Difluoro-8-(2-hydroxypropyl)-4-hydroxyquinoline-3-carboxylate (153)

To 14.2 g (30 mmol) g of the compound (152) obtained above, 130 ml of Dowtherm A (Trademark) was added, and the solution was heated until a fraction of 200° C. was taken out. Further, the solution was heated at reflux for 20 minutes. After air-cooling, 15 ml of concentrated hydrochloric acid was added to the solution. After stirring for 1.5 hours at room temperature, deposited crystals were filtered off and washed with ethanol and ether in this order to obtain 5.32 g of the subject compound (153) in a 57% yield.

REFERENCE EXAMPLE 27

Ethyl 1-Amino-6,7-difluoro-8-(2-hydroxypropyl)-1,4-dihydro-4-oxoquinoline-3-carboxylate (154)

2.40 g (7.7 mmol) of the compound (153) obtained above and 2.13 g (15.4 mmol) of anhydrous potassium carbonate were added to 50 ml of dimethylformamide, and the solution was stirred for 4 hours at room temperature. 6.58 g (23.1 mmol) of ethyl o-(mesitylene-sulfonyl)acetohydroxamate was added to 10 ml of dioxane, and while cooling on ice, 2.5 ml of 70% perchloric acid was dropped below 10° C. through 15 minutes. The solution was stirred for 20 minutes, and was added to 50 ml of ice/water. Crystals were filtered off and washed with ice/water and was dissolved in 50 ml of methylene chloride. The organic layer was separated and was dropped to the previously prepared reaction solution of the dimethylformamide through 5 minutes, while cooling on ice, after drying over magnesium sulfate. The solution was stirred for 1 hour, and 100 ml of water was added to the solution. Crystals were filtered off and washed with water, ethanol and ether in this order to obtain 1.00 g of the subject compound (154) in a 40% yield.

EXAMPLE 33

Ethyl 4,5-Difluoro-2-methyl-2,3-dihydro-7-oxo-1H,7H-pyrido[3,2,1-ij]cinnoline-8-carboxylate (155)

2.35 g (7.2 mmol) of the compound (154) obtained in Reference Example 27 and 2.98 g (11.3 mmol) of triphenylphosphine were added to 50 ml of tetrahydrofuran, and 50 ml of tetrahydrofuran solution containing 1.97 g (11.3 mmol) of diethyl azodicarboxylate was dropped to the solution at room temperature through 2 hours. After 20 minutes, the solvent was removed by distillation. Solids were dispersed to ethanol and filtered off and washed with ethanol and ether in this order to obtain 1.45 g of the subject compound (155) in a 65% yield.

Colorless powder:

Melting point: 226°–230° C. (decomp.)

$^1$H-NMR (DMSO-$d_6$)

1.25 (t, J=5.9 Hz, 3H), 1.29 (t, J=7.0 Hz, 3H), 2.61 (dd, J=8.4 Hz, 17.0 Hz, 1H), 3.12 (q, J=16.8 Hz, 1H), 3.27–3.51 (m, 1H), 4.20 (q, J=7.0 Hz, 2H), 6.77 (d, J=9.9 Hz, 1H), 7.90 (dd, J=10.2 Hz, 10.2 Hz, 1H), 8.44 (s, 1H)

EXAMPLE 34

Methyl 4,5-Difluoro-2,3-dihydro-1,2-dimethyl-7-oxo-1H,7H-pyrido[3,2,1-ij]cinnoline-8-carboxylate (156)

To 1.45 g (4.7 mmol) of the compound (155) obtained in Example 33, 10 ml (109 mmol) of dimethyl sulfate was added, and the solution was heated 3.5 hours at 120° C. After air-cooling, to 90 ml of ice/water containing 15 g (109 mmol) of anhydrous potassium carbonate, the solution was added, and the solution was stirred overnight. The solution was extracted with 50 ml of chloroform, and after drying over magnesium sulfate, the solvent was removed by distillation. The residue was separated by column chromatography (silica gel 8 g, eluent solvent; chloroform:methanol=100:1) to obtain 830 mg of the subject compound (156) in a 57% yield.

Colorless powder:
Melting point: 184°–185° C.
¹H-NMR (CDCl₃)
1.27 (d, J=6.9 Hz, 3H), 2.77 (s, 3H), 2.82 (dd, J=5.5 Hz, 18.3 Hz, 1H), 3.16 (dd, J=5.1 Hz, 17.6 Hz, 1H), 3.93 (s, 3H), 3.54–3.66 (m, 1H), 8.15 (dd, J=9.2 Hz, 9.2 Hz, 1H), 8.59 (s, 1H)

EXAMPLE 35

4,5-Difluoro-2,3-dihydro-1,2-dimethyl-7-oxo-1H,7H-pyrido[3,2,1-ij]cinnoline-8-carboxylic acid (157)

To 830 mg (2.7 mmol) of the compound (156) obtained in Example 34, 4 ml of concentrated hydrochloric acid and 16 ml of acetic acid were added and the solution was heated at reflux for 3 hours. 10 ml of water was added to the solution. Solids were filtered off and washed with ethanol and ether in this order to obtain 700 mg of the subject compound (157) in a 88% yield.
Colorless powder:
Melting point: 270°–271° C.
¹H-NMR (DMSO-d₆)
1.13 (d, J=7.0 Hz, 3H), 2.80 (s, 3H), 2.91 (dd, J=5.1. Hz, 18.5 Hz, 1H), 3.25 (dd, J=4.8 Hz, 18.1 Hz, 1H), 3.71–3.78 (m, 1H), 8.19 (dd, J=8.4 Hz, 8.4 Hz, 1H), 8.79 (s, 1H)

EXAMPLE 36

5-Fluoro-4-{(cis (−)-3-amino-4-methylpyrrolidin)-1-yl}-2,3-dihydro-1,2α,62-dimethyl-7-oxo-1H,7H-pyrido[3,2,1-ij]cinnoline-8-carboxylic acid (158)

100 mg (0.34 mmol) of the compound (157) obtained in Example 35, 118 mg (0.68 mmol) of cis (−)-3-amino-4-methylpyrrolidine dihydrochloride and 310 mg (2.04 mmol) of 1,8-diazabicyclo[5.4.0]-7-undecene were added to 1 ml of acetonitrile, and the solution was heated at reflux for 3 hours. Then, the solvent was removed by distillation, and the solid matter was extracted over 40 ml of chloroform. After drying over magnesium sulfate, the solvent was removed by distillation. The solid matter was dispersed in ethanol and ether and filtered off to obtain 80 mg of the subject compound (158) in a 64% yield.
Slightly brown powder:
Melting point: 228°–230° C. (decomp.)
¹H-NMR (DMSO-d₆)
1.00–1.21 (m, 6H), 2.80–2.86 (m, 4H), 3.94–4.04 (m, 1H), 7.84 (d, J=13.5Hz, 1H), 8.64 (s, 1H)

EXAMPLE 37

5-Fluoro-4-{(3R)-((1′S)-aminoethyl)pyrrolidin)-1-yl}-2,3-dihydro-1,260,62-dimethyl-7-oxo-1H,7H-pyrido[3,2,1-ij]-cinnoline-8-carboxylic acid Hydrochloride (159)

100 mg (0.34 mmol) of the compound (158) obtained in Example 36, 127 mg (0.68 mmol) of (3R)-((1′S)-aminoethyl)pyrrolidine dihydrochloride and 310 mg (2.04 mmol) of 1,8-diazabicyclo[5,4,0]-7-undecene were added to 1 ml of acetonitrile, and the solution was heated at reflux for 3 hours. Then, the solvent was removed by distillation. 5 ml of ethanol and 1 ml concentrated hydrochloric acid were added to the solid and the solvent was removed by distillation. The deposited solids were dispersed in ethanol and filtered to obtain 10 mg of the subject compound (159) in a 8% yield.

Yellowish powder:
Melting point: >210° C. (decomp.)
¹H-NMR (DMSO-d₆)
1.01, 1.23 (each d, each J=8.1 Hz, each 1.5 H), 1.32 (d, J=8.1 Hz, 3H) 1.67–1.79 (m, 1H), 2.10 (brs, 1H), 2.39–2.48 (m, 1H), 2.79–3.00 (m, 4H), 3.30 (brs. 1H), 3.49–3.80 (m, 6H), 7.85 (d, J=13.5 Hz, 1H), 8.30 (brs, 1H), 8.65 (s, 1H)

EXAMPLE 38

5-Fluoro-4-(pyrrolidin-1-yl)-2,3-dihydro-1,2-dimethyl-7-oxo-1H,7H-pyrido[3,2,1-ij]cinnoline-8-carboxylic acid (160)

100 mg (0.34 mmol) of the compound (157) obtained in Example 35 and 88 mg (1.24 mmol) of pyrrolidine were added to 1 ml of acetonitrile, and the solution was heated at reflux for 3 hours. Then, the solvent was removed by distillation, and the residue was extracted with 20 ml of chloroform, and after drying over magnesium sulfate, the solvent was removed by distillation. The residue was solidified with ether and the solids were filtered off to obtain 70 mg of the subject compound (160) in a 60% yield.
Colorless powder:
Melting point: 224°–225° C. (decomp.)
¹H-NMR (CDCl₃)
1.19 (d, J=7.0 Hz, 3H), 2.01 (brs, 4H), 2.68 (dd, J=5.9 Hz, 16.8 Hz, 1H), 2.82 (s, 3H), 3.01 (dd, J=5.1 Hz, 17.0 Hz, 1H), 3.52 (brs, 5H), 7.97 (d, J=13.9 Hz, 1H), 8.77 (s, 1H)

EXAMPLE 39

(1) Ethyl 5-Fluoro-4-{cyano(ethoxycarbonyl)methyl}-2,3-dihydro-1-methyl-7-oxo-1H,7H-pyrido[3,2,1-ij]cinnoline-8-carboxylate (161)

168 mg (4.2 mmol) of 60% sodium hydride was added to 20 ml of N,N-dimethylformamide, and while cooling on ice, 452 mg (4 mmol) of ethyl cyanoacetate was dropped to the solution. The solution was stirred for 1 hour at room temperature. 612 mg (2 mmol) of ethyl 4,5-difluoro-2,3-dihydro-1-methyl-7-oxo-1H,7H-pyrido[3,2,1-ij]cinnoline-8-carboxylate was added to the solution, and the solution was stirred overnight at room temperature. The solution was heated at 70° C. for 2 hours, and the solvent was removed by distillation. 80 ml of chloroform and 20 ml of water were added to the residue, and the solution was acidified with citric acid. The organic layer was separated and after drying over magnesium sulfate, the solvent was removed by distillation. The residue was purified by column chromatography (silica gel 20 g, eluent solvent; ethyl acetate) to obtain 450 mg of the subject compound (161).
Colorless prisms:
Melting point: 153°–154.5° C.
¹H-NMR (CDCl₃)
1.33, 1.42 (each t, each J=7.0 Hz, each 3H), 2.87 (s, 8H), 2.91–2.96, 3.27–8.39 (each m, each 1H), 3.55 (brs, 2H), 4.80–4.41 (m, 4H), 5.35 (s, 1H), 8.18 (d, J=10.3 Hz, 1H), 8.62 (s, 1H)

(2) The following compound was obtained in the similar manner as Example 39 (1).

Ethyl 5-Fluoro-4-{cyano(t-butoxycarbonyl)methyl}-2,3-dihydro-1-methyl-7-oxo-1H,7H-pyrido[3,2,1-ij]cinnoline-8-carboxylate (162)

Colorless needles:
Melting point: 169°–170.5° C.
$^1$H-NMR (CDCl$_3$)
1.41 (t, J=7.3 Hz, 3H), 1.50 (s, 9H), 2.87 (s, 3H), 2.92–3.00, 3.29–3.40 (each m, each 1H), 3.55 (brs, 2H), 4.40 (q, J=6.9 Hz, 2H), 5.27 (s, 1H), 8.17 (d, J=10.3 Hz, 1H), 8.62 (s, 1H)

EXAMPLE 40

8-Carboxy-5-fluoro-2,3-dihydro-1-methyl-7-oxo-1H,7H-pyrido[3,2,1-ij]cinnoline-4-acetic acid (163)

To 450 mg of the compound (161) obtained in Example 39, 4 ml of concentrated hydrochloric acid and 16 ml of acetic acid were added, and the solution was heated at reflux for 7.5 hours. The solvent was removed by distillation, and crystals were filtered off and washed with ethanol and ether in this order to obtain 124 mg of the subject compound (163).

Colorless prisms:
Melting point: 215° C. (decomp.)
$^1$H-NMR (DMSO-d$_6$)
2.85 (s, 3H), 3.09, 3.56, 3.92 (each brs, each 2H), 7.95 (d, J=9.5 Hz, 1H), 8.78 (s, 1H)

EXAMPLE 41

5-Fluoro-1,4-dimethyl-2,3-dihydro-7-oxo-1H,7H-pyrido[3,2,1-ij]cinnoline-8-carboxylic acid (164)

100 mg of the compound (163) obtained in Example 40 and 1.4 ml of triethylamine were added to 5 ml of ethanol, and the solution was heated at reflux for 15.5 hours. After air-cooling, the solids were filtered and washed successively with ethanol and ether to obtain 65 mg of the subject compound (164).

Colorless powder:
Melting point: >260° C. (decomp.)
$^1$H-NMR (DMSO-d$_6$)
2.38, 2.86 (each s, each 3H), 3.07 (t, J=5.5 Hz, 2H), 3.31 (t, J=3.3 Hz, 2H), 7.91 (d, J=9.5 Hz, 1H), 8.76 (s, 1H)

EXAMPLE 42

Ethyl 4-Cyanomethyl-5-fluoro-1-methyl-2,3-dihydro-7-oxo-1H,7H-pyrido[3,2,1-ij]cinnoline-8-carboxylate (165)

1.60 g of the compound (162) obtained in Example 39 (2) was added to 20 ml of methylene chloride, and 6 ml of trifluoroacetic acid was added to the solution. The solution was stirred for 1.5 hours. 4 ml of trifluoroacetic acid was added to the solution, and the solution was stirred overnight. The solvent was removed by distillation, and the residue was crystallized from ethyl ether. Crystals were filtered off to obtain 410 mg of the subject compound (165).

Slightly brown powder:
Melting point: 208.5°–210.5° C. (decomp.)
$^1$H-NMR (CDCl$_3$)
1.42 (t, J=7.0 Hz, 3H), 2.88 (s, 3H), 3.13 (t, J=5.9 Hz, 2H), 3.58 (t, J=5.9 Hz, 2H), 3.88 (s, 2H), 4.40 (q, J=7.0 Hz, 2H), 8.11 (d, J=9.5 Hz, 1H), 8.61 (s, 1H)

IR (KBr) 2250 cm$^{-1}$ (CN)

EXAMPLE 43

5-Fluoro-4-hydroxy-2,3-dihydro-1-methyl-7-oxo-1H,7H-pyrido[3,2,1-ij]cinnoline-8-carboxylic acid (166)

2.78 g of the compound (8) obtained in Example 3 was added to 10 ml of aqueous 30% potassium hydroxide solution, and the solution was heated at reflux for 6 hours. After air-cooling, the solution was acidified with 6N hydrochloric acid, and the deposited solids were filtered off and washed with water, ethanol and isopropyl ether in this order to obtain 2.60 g of the subject compound (166).

Colorless powder:
Melting point: >290° C.
$^1$H-NMR (DMSO-d$_6$)
2.84 (s, 3H), 2.94 (brs, 2H), 3.49 (brs, 2H), 7.90 (d, J=11.0 Hz, 1H), 8.70 (s, 1H)

EXAMPLE 44

Methyl 5-Fluoro-4-hydroxy-2,3-dihydro-1-methyl-7-oxo-1H,7H-pyrido[3,2,1-ij]cinnoline-8-carboxylate (167)

To 100 ml of methanol, while cooling on ice, 9 ml of thionyl chloride was added, and the solution was stirred for 30 minutes at the same temperature. 2.60 g of the compound (166) obtained in Example 43 was added to the solution, and the solution was heated at reflux for 24 hours. After air-cooling, insoluble matter was removed by filtering, and the filtrate was removed by distillation. To the residue, chloroform was added, and the formed solid matter was filtered off to obtain 2.20 g of the subject compound (167).

Slightly yellowish powder:
Melting point: >290° C. (decomp.)
$^1$H-NMR (DMSO-d$_6$)
2.78 (s, 3H), 2.90, 3.43 (each brs, each 2H), 3.74 (s, 3H), 7.74 (d, J=11.4 Hz, 1H), 8.46 (s, 1H)

EXAMPLE 45

Methyl 5-Fluoro-4-methanesulfonyloxy-2,8-dihydro-1-methyl-7-oxo-1H,7H-pyrido[3,2,1-ij]cinnoline-8-carboxylate (168)

304 mg of the compound (167) obtained in Example 44 was added to 2 ml of pyridine, and 120 mg of methane-sulfonyl chloride was added to the solution. The solution was stirred for 3 hours at room temperature. 50 ml of chloroform was added to the solution, and the solution was washed with aqueous 5% citric acid solution. The organic layer was separated, and after drying over magnesium sulfate, the solvent was removed by distillation. To the residue, ethanol was added, and the solid matter was filtered off and washed with isopropyl ether to obtain 260 mg of the subject compound (168).

Colorless powder:
Melting point: 247°–250° C.
$^1$H-NMR (DMSO-d$_6$)
2.82 (s, 3H), 3.11, 3.48 (each brs, each 2H), 3.70, 3.76 (each s, each 3H), 7.95 (d, J=10.3 Hz, 1H), 8.57 (s, 1H)

EXAMPLE 46

Methyl 5-Fluoro-4-(4-methylphenylsulfonyloxy)-2,3-dihydro-1-methyl-7-oxo-1H,7H-pyrido[3,2,1-ij]cinnoline-8-carboxylate (169)

304 mg of the compound (168) obtained in Example 45 was added to 2 ml of pyridine, and 260 mg of p-toluene-sulfonyl chloride was added to the solution. The solution was stirred for 2 hours at room temperature. 50 ml of chloroform was added to the solution, and the solution was washed with water and aqueous 5% citric acid solution. The organic layer was separated, and after drying over magnesium sulfate, the solvent was removed by distillation. To the residue, ethanol was added, and the solid matter was filtered off and washed with isopropyl ether to obtain mg of the subject compound (169).

Slightly yellowish powder:
Melting point: 182°–186° C.
$^1$H-NMR (CDCl$_3$)
2.51 (s, 3H), 2.88 (s, 3H), 3.23, 3.47 (each t, each J=6.0 Hz, each 2H), 3.92 (s, 3H), 7.40, 7.86 (each d, each J=8.1 Hz, each 2H), 8.04 (d, J=9.9 Hz, 1H), 8.64 (s, 1H)

EXAMPLE 47

Methyl 5-Fluoro-4-(trifluoromethanesulfonyloxy)-2,3-dihydro-1-methyl-7-oxo-1H,7H-pyrido[3,2,1-ij]cinnoline-8-carboxylate (170)

2.8 g of the compound (169) obtained in Example 46 was added to 10 ml of pyridine, and while cooling on ice, 2.35 ml of trifluoromethanesulfonic anhydride was added to the solution through 20 minutes. The solution was stirred for 24 hours at room temperature. 200 ml of chloroform was added to the solution, and the solution was washed with aqueous 5% citric acid solution. The organic layer was separated and after drying over magnesium sulfate, the solvent was removed by distillation. To the residue, ethanol was added, and the solid matter was filtered off and purified by column chromatography (silica gel, eluent solvent; chloroform: ethyl acetate=1:1). The solid matter was filtered off and washed with isopropyl ether to obtain 1.2 g of the subject compound (170).

Colorless powder:
Melting point: 170°–172° C.
$^1$H-NMR (CDCl$_3$)
2.90 (s, 3H), 3.20, 3.55 (each t, each J=6.0 Hz, each 2H), 3.95 (s, 3H), 8.25 (d, J=10.0 Hz, 1H), 8.65 (s, 1H)

EXAMPLE 48

Methyl 5-Fluoro-4-(3-oxo-1-cyclohexen-1-yl)-2,3-dihydro-1-methyl-7-oxo-1H,7H-pyrido[3,2,1-ij]cinnoline-8-carboxylate (171)

424 mg of the compound (170) obtained in Example 47, 404 mg of 3-tributylstanyl-2-cyclohexen-1-one, 127 mg of lithium chloride and 14 mg of bis(triphenylphosphine)palladium (II) chloride were added to 5 ml of tetrahydrofuran, and the solution was heated at reflux for three days under nitrogen. The solvent was removed by distillation. To the residue, n-hexane was added, and the solid matter was filtered off. The obtained solid matter was separated by column chromatography (silica gel, eluent solvent; chloroform: ethyl acetate=8:1) to obtain 120 mg of the subject compound (171).

Slightly yellowish oily material:
$^1$H-NMR (DMSO-d$_6$)
2.05–2.20 (m, 2H), 2.59 (s, 2H), 2.84 (s, 3H), 2.85–3.03 (m, 2H), 3.44 (brs, 2H), 3.75 (s, 3H), 6.13 (s, 1H), 7.83 (d, J=10.0 Hz, 1H), 8.56 (s, 1H)

EXAMPLE 49

5-Fluoro-4-(3-oxo-1-cyclohexen-1-yl)-2,3-dihydro-1-methyl-7-oxo-1H,7H-pyrido[3,2,1-ij]cinnoline-8-carboxylic acid (172)

120 mg of the compound (171) obtained in Example 48 was added to a mixture solution of 3 ml of tetrahydrofuran, 1 ml of 6N hydrochloric acid and 1 ml of water, and the solution was stirred for four days at room temperature. The deposited solid matter was filtered off and washed with water and ethanol in this order to obtain 44 mg of the subject compound (172).

Colorless needles:
Melting point: >300° C.
H-NMR (DMSO-d$_6$)
2.00–2.20 (m, 2H), 2.60 (brs, 2H), 2.91 (s, 3H), 3.05 (brs, 2H), 3.45–3.55 (m, 2H), 6.17 (s, 1H), 8.01 (d, J=10.0 Hz, 1H), 8.81 (s, 1H)

EXAMPLE 50

Ethyl 3,4-Difluoro-1,2-dihydro-6-oxo-1H,6H-pyrido[3,2,1-hi]indazole-7-carboxylate (173)

1.29 g (4 mmol) of the compound (99) obtained in Example 16 was added to 8 ml of a mixture solution of concentrated hydrochloric acid-acetic acid (at a ratio of 1:4 by volume), and the solution was heated at reflux for 30 minutes. After air-cooling, the solution was diluted with 50 ml of water, and deposited solids were filtered off and washed with water, ethanol and ether in this order to obtain 1.07 g of the subject compound (173) in a 97% yield.

Slightly yellowish powder:
Melting point: 192°–197° C. (decomp.)
$^1$H-NMR (DMSO-d$_6$)
1.27 (t, J=7.0 Hz, 3H), 4.19 (q, J=7.0 Hz, 2H), 4.88 (d, J=7.5 Hz, 2H), 7.77 (dd, J=7.0 Hz, 10.6 Hz, 1H), 7.98 (t, J=7.5 Hz, 1H), 8.68 (s, 1H)

EXAMPLE 51

Ethyl 3,4-Difluoro-1,2-dihydro-1-hydroxymethyl-6-oxo-1H,6H-pyrido[3,2,1-hi]indazole-7-carboxylate (174)

1.07 g (3.9 mmol) of the compound (178) obtained in Example 50 was added to a mixture solution of 20 ml of formic acid and 10 ml of 37% formaldehyde solution, and the solution was heated at reflux for 2 hours. After air-cooling, the solution was diluted with 50 ml of water, and deposited crystals were filtered off and washed with water, cooled ethanol and ether in this order to obtain 1.14 g of the subject compound (174) in a 96% yield.

Colorless needles:
Melting point: 194°–201° C. (decomp.)
$^1$H-NMR (DMSO-d$_6$)
1.28 (t, J=7.0 Hz, 3H), 4.22 (q, J=7.0 Hz, 2H), 4.71 (d, J=7.0 Hz, 2H), 4.93 (s, 2H), 6.26 (t, J=7.0 Hz, 1H), 7.75 (dd, J=7.0 Hz, 10.6 Hz, 1H), 8.83 (s, 1H)

EXAMPLE 52

3,4-Difluoro-1,2-dihydro-1-hydroxymethyl-6-oxo-1H,6H-pyrido[3,2,1-hi]indazole-7-carboxylic acid (175)

61 mg (0.2 mmol) of the compound (174) obtained in Example 51 was added to a mixture solution of 1 ml of formic acid and 1 ml of water, and the solution was heated at reflux for 6 hours. After air-cooling, the solution was diluted with 50 ml of water, and deposited crystals were filtered off and washed with water, ethanol and ether in this order to obtain 41 mg of the subject compound (175) in a 73% yield.

Colorless needles:
Melting point: 265°–277° C. (decomp.)
$^1$H-NMR (DMSO-$d_6$)
4.85 (d, J=7.0 Hz, 2H), 5.04 (s, 2H), 6.31 (t, J=7.0 Hz, 1H), 8.02 (dd, J=7.0 Hz, 10.6 Hz, 1H), 9.30 (s, 1H)

EXAMPLE 53

Ethyl 3,4-Difluoro-1,2-dihydro-1-methoxymethyl-6-oxo-1H,6H-pyrido[3,2,1-hi]indazole-7-carboxylate (176)

61 mg (0.2 mmol) of the compound (175) obtained in Example 52 was added to 2 ml of dimethylsulfate, and the solution was stirred at 120° C. for 6 hours. After air-cooling, the content was added to 50 ml of saturated aqueous sodium carbonate solution, and the solution was stirred for 4 hours at room temperature. The solution was extracted with chloroform, and after the extract was dried over magnesium sulfate, the solvent was removed under reduced pressure by distillation. The solid residue was dispersed in ether, and the precipitate was filtered off and washed with ether to obtain 57 mg of the subject compound (176) in a 89% yield.

Yellowish powder:
Melting point: 183°–199° C. (decomp.)
$^1$H-NMR (DMSO-$d_6$)
1.28 (t, J=7.0 Hz, 3H), 3.34 (s, 3H), 4.24 (q, J=7.0 Hz, 2H), 4.67 (s, 2H), 4.98 (s, 2H), 7.79 (dd, J=7.0 Hz, 10.6 Hz, 1H), 8.88 (s, 1H)

EXAMPLE 54

Ethyl 4,5-Difluoro-1-hydroxymethyl-2,3-dihydro-7-oxo-1H,7H-pyrido[3,2,1-ij]cinnoline-8-carboxylate (177)

100 mg of the compound (5) obtained in Example 1 was dissolved in 3 ml of acetic acid, and while stirring, 1.5 ml of formalin was added to the solution. The solution was stirred for 30 minutes, and the deposited solid matter was filtered off and washed with ether to obtain 64 mg of the subject compound (177).

Colorless needles:
Melting point: >245° C. (decomp.)
$^1$H-NMR (DMSO-$d_6$)
1.27 (t, J=7.0 Hz, 3H), 3.01 (brs, 2H), 3.63 (t, J=6.4 Hz, 2H), 4.21 (q, J=7.0 Hz, 2H), 4.50 (d, J=6.3 Hz, 2H), 6.20 (t, J=6.3 Hz, 1H), 7.92 (dd, J=8.8 Hz, 10.7 Hz, 1H), 8.48 (s, 1H)

EXAMPLE 55

4,5-Difluoro-1-hydroxymethyl-2,3-dihydro-7-oxo-1H,7H-pyrido[3,2,1-ij]cinnoline-8-carboxylic acid (178)

50 mg of compound (10) obtained in Example 3(4) was suspended in 3 ml of acetic acid, and while stirring, 1.5 ml of formalin was added to the solution. The solution was stirred for 1 hour, and ether was added to the solution. The deposited solid matter was filtered off and washed with ether to obtain 40 mg of the subject compound (178).

Colorless needles:
Melting point: >255° C. (decomp.)
$^1$H-NMR (DMSO-$d_6$)
3.01 (brs, 2H), 3.69 (t, J=5.9 Hz, 2H), 4.57 (d, J=7.0 Hz, 2H), 6.22 (t, J=7.0 Hz, 1H), 8.17 (dd, J=8.8 Hz, 10.3 Hz, 1H), 8.77 (s, 1H)

EXAMPLE 56

5-Fluoro-4-(pyrrolidin-1-yl)-1-hydroxymethyl-2,3-dihydro-7-oxo-1H,7H-pyrido[3,2,1-ij]cinnoline-8-carboxylic acid (179)

200 mg of the compound (160) obtained in Example 38 was added to a mixture solvent of 8 ml of acetic acid and 4 ml of formalin, and the solution was heated at 80° C. for 2 hours. The deposited solid matter was filtered off and washed with ether to obtain 50 mg of the subject compound (179).

Yellowish powder:
Melting point: 258°–261° C. (decomp.)
$^1$H-NMR (DMSO-$d_6$)
2.51 (brs, 2H), 2.90 (t, J=5.9 Hz, 2H), 3.24–3.72 (m, 6H), 4.55 (d, J=6.8 Hz, 2H), 6.25 (t, J=6.8 Hz, 1H), 7.82 (d, J=14.2 Hz, 1H), 8.62 (s, 1H)

EXAMPLE 57

Ethyl 4,5-Difluoro-1-methoxymethyl-2,3-dihydro-7-oxo-1H,7H-pyrido[3,2,1-ij]cinnoline-8-carboxylate (180)

65 mg of the compound (177) obtained in Example 54 was suspended in 5 ml of tetrahydrofuran, and 270 μl of diethylaminosulfurtrifluoride was added to the solution. The solution was stirred for 4 hours, and 1 ml of methanol was added to the solution. The deposited solid matter was filtered off and washed with ether to obtain 34 mg of the subject compound (180).

Colorless needles:
Melting point: >240° C. (decomp.)
$^1$H-NMR (CDCl$_3$)
1.41 (t, J=7.0 Hz, 3H), 3.05 (t, J=5.9 Hz, 2H), 3.36 (s, 3H), 3.63 (t, J=6.4 Hz, 2H), 4.35–4.42 (m, 4H), 8.13 (dd, J=8.8 Hz, 10.3 Hz, 1H), 8.50 (s, 1H)

EXAMPLE 58

Ethyl 4,5-Difluoro-1-ethoxymethyl-2,3-dihydro-7-oxo-1H,7H-pyrido[3,2,1-ij]cinnoline-5-carboxylate (181)

65 mg of the compound (177) obtained in Example 54 was suspended in 5 ml of tetrahydrofuran, and 270 μl of diethylaminosulfurtrifluoride was added to the solution. The solution was stirred for 4 hours, and 1 ml of ethanol was added to the solution. The deposited solid matter was filtered off and washed with ether to obtain 28 mg of the subject compound (181).

Colorless powder:
Melting point: >190° C. (decomp.)
$^1$H-NMR (CDCl$_3$)
1.11 (t, J=7.3 Hz, 3H), 1.40 (t, J=7.0 Hz, 3H), 3.05 (t, J=5.9 Hz, 2H), 3.55 (q, J=7.3 Hz, 2H), 3.64 (t, J=6.4 Hz, 2H), 4.34–4.46 (m, 4H), 8.13 (dd, J=8.8 Hz, 10.3 Hz, 1H), 8.50 (s, 1H)

EXAMPLE 59

4,5-Difluoro-1-benzyl-2,3-dihydro-7-oxo-1H, 7H-pyrido [3,2,1-ij]cinnoline-8-carboxylic acid (182)

530 mg of compound (10) obtained in Example 3(4) was added to 15 ml of toluene, and then 1 ml of benzyl alcohol and 456 mg of p-toluenesufonic acid monohydrate were added to the solution. While the produced water was removed, the solution was heated at 130° C. for 48 hours. The solvent was removed by distillation. To the residue, ether was added, and the solid matter was filtered off and washed with ether to obtain 370 mg of the subject compound (182).

Slightly yellowish needles:
Melting point: >194° C. (decomp.)
$^1$H-NMR (CDCl$_3$)
3.18 (t, J=5.9 Hz, 2H), 3.59 (t, J=6.4 Hz, 2H), 4.11 (s, 2H), 7.27–7.40 (m, 5H), 8.20 (dd, J=8.8 Hz, 9.8 Hz, 1H), 8.49 (s, 1H)

EXAMPLE 60

5-Fluoro-4-(pyrrolidin-1-yl)-1-benzyl-2,3-dihydro-7-oxo-1H,7H-pyrido[3,2,1-ij]cinnoline-8-carboxylic acid (183)

50 mg of compound (182) obtained in Example 59, 26 mg of pyrrolidine and 10 mg of triethylamine were added to 3 ml of acetonitrile, and the solution was heated at 80° C. for 3 hours. The solvent was removed by distillation. To the residue, ethanol was added, and the solid matter was filtered off and washed with ethanol and ether in this order to obtain 33 mg of the subject compound (183).

Slightly yellowish needles:
Melting point: 174°–180° C.
$^1$H-NMR (CDCl$_3$)
2.04 (brs, 4H), 2.97 (t, J=5.9 Hz, 2H), 3.46 (t, J=6.4 Hz, 2H), 3.58 (brs, 4H), 4.16 (s, 2H), 7.26–7.39 (m, 5H), 7.99 (d, J=13.7 Hz, 1H), 8.46 (s, 1H)

EXAMPLE 61

4-(2-Aminoethylthio)-5-fluoro-1-methyl-2,3-dihydro-7-oxo-1H,7H-pyrido[3,2,1-ij]cinnoline-8-carboxylic acid (184)

100 mg of compound (8) obtained in Example 3 (1), 56 mg of 2-amino-ethanethiol and 109 mg of triethylamine were added to 2 ml of acetonitrile, and the solution was heated at reflux for 2 hours. After air-cooling, the solvent was removed by distillation. To the residue, ethanol was added, and the deposited solids were filtered off and washed with ether to obtain 60 mg of the subject compound (184).

Colorless powder:
Melting point: >200° C. (decomp.)
$^1$H-NMR (DMSO-d$_6$)
2.68 (t, J=6.4 Hz, 2H), 2.87 (s, 3H), 3.07 (t, J=6.8 Hz, 2H), 3.22–3.30, 3.51–3.62 (each m, each 2H), 7.99 (d, J=9.8 Hz, 1H), 8.79 (s, 1H)

REFERENCE EXAMPLE 28

3-Fluoro-2-(2-hydoxyethyl)nitrobenzene (185)

While cooling on ice, 6.52 g (94.5 mmol) of sodium nitrite was added to 45 ml of concentrated sulfuric acid through 30 minutes. Then, 180 ml of acetic acid solution containing 14.5 g (72.9 mmol) of the compound (124) obtained in Reference Example 6 was dropped to the solution through 1.5 hours below 20° C. The solution was stirred for 20 minutes. The solution was dropped to 300 ml ethanol suspension containing 40.9 g (285.8 mmol) of cuprous oxide. The reaction solution was heated at 50° C. and was stirred for minutes. The solution was added to 1.0 l of ice/water, and 1.0 l of chloroform was added to the solution. The insoluble matter was filtered off, and the organic layer was separated. After drying over magnesium sulfate, the solvent was removed by distillation, and the residue was separated by column chromatography (silica gel 500 g, eluent solvent; chloroform) to obtain 6.22 g of the subject compound (185) in a 46% yield.

REFERENCE EXAMPLE 29

Diethyl {3-Fluoro-2-(2-hydroxyethyl)anilino}-methylene malonate (186)

15.4 g of iron powder and 1.4 ml of concentrated hydrochloric acid were added to a mixture solvent of 160 ml of water and 30 ml of ethanol, and the solution was heated at 80°–90° C. 20.3 g (110 mmol) of the compound (185) obtained above was added to the solution through 15 minutes, and the solution was heated for 10 minutes. After air-cooling, 200 ml of ethyl acetate was added to the solution, and insoluble matter was filtered. The organic layer was separated and was washed with aqueous 10% sodium hydrogen carbonate solution. After drying over magnesium sulfate, the solvent was removed by distillation. To the obtained oily material, 23.2 g (107 mmol) of diethyl ethoxymethylenemalonate was added, and the solution was heated at 120° C. for 4 hours. After air-cooling, crystals were dispersed in n-hexane and filtered off to obtain 21.9 g of the subject compound (186) in a 61% yield.

REFERENCE EXAMPLE 30

Ethyl 7-Fluoro-8-(2-hydroxyethyl)-4-hydroxyquinoline-3-carboxylate (187)

To 120 ml of methylene chloride solution containing 20.0 g (61.7 mmol) of compound (186) obtained above and 5.11 g (75 mmol) of imidazole, 25 ml of methylene chloride solution containing 11.2 g (74.4 mmol) of t-butyldimethylchlorosilane was dropped through 5 minutes, and the solution was stirred for 40 minutes at room temperature. The solution was washed with 50 ml of water, and after drying over magnesium sulfate, the solvent was removed by distillation. To the obtained oily material, 210 ml of Dowtherm A (Trademark) was added, and the solution was heated until a fraction of 200° C. was taken off. The solution was further heated at reflux for 20 minutes. After air-cooling, 30 ml of concentrated hydro-chloric acid was added to the solution. After stirring for 20 minutes at room temperature, the solution was neutralized with sodium hydrogen carbonate. The deposited crystals were filtered off and washed with water, ethanol and ether in this order to obtain 8.99 g of the subject compound (187) in a 52% yield.

REFERENCE EXAMPLE 31

Ethyl 1-Amino-7-fluoro-8-(2-hydroxyethyl)-1,4-dihydro-4-oxoquinoline-5-carboxylate (188)

8.99 g (32.2 mmol) of the compound (187) obtained above and 8.89 g (64.4 mmol) of anhydrous potassium carbonate were added to 210 ml of N,N-dimethylformamide, and the solution was stirred at room temperature for 4 hours. 27.6 g (96.7 mmol) of ethyl o-(mesitylenesulfonyl)acetohydoxamate was added to 40 ml of dioxane, and while cooling on ice, 10.5 ml of 70% perchloric acid was dropped to the solution below 10° C. over 30 minutes. The solution was stirred for 20 minutes, and was then added to 400 ml of ice/water. Crystals were filtered off and washed on ice/water and was dissolved in 150 ml of methylene chloride. The organic layer was separated and after drying over magnesium sulfate, while cooling on ice, the solution was dropped into the previously prepared reaction solution of N,N-dimethylformamide through 10 minutes. The solution was stirred for 1 hour, and 200 ml of water was added to the solution. Crystals were filtered off and washed with water, ethanol and ether in this order to obtain 1.81 g of the subject compound (188) in a 19% yield.

EXAMPLE 62

Ethyl 4-Fluoro-2,3-dihydro-7-oxo-1H,7H-pyrido[3,2,1-ij]cinnoline-8-carboxylate (189)

1.81 g (6.2 mmol) of the compound (188) obtained in Reference Example 31 and 2.55 (9.7 mmol) of triphenylphosphine were added to 40 ml of tetrahydrofuran, and 40 ml of tetrahydrofuran solution containing 1.69 (9.7 mmol) of diethyl azodicarboxylate was dropped to the solution at room temperature through 1.5 hours. After 30 minutes, the solvent was removed by distillation. Solids were dispersed in ethanol, filtered off and washed with ethanol and ether in this order to obtain 1.24 g of the subject compound (189) in a 72% yield.
Colorless powder:
Melting point: 224°-225° C. (decomp.)
$^1$H-NMR (DMSO-$d_6$)
1.27 (t, J=6.9 Hz, 3H), 2.88 (brs, 2H), 3.39 (brs, 2H), 4.20 (q, J=7.0 Hz, 2H), 6.85 (brs, 1H), 7.34 (dd, J=8.8 Hz, 8.8 Hz, 1H), 8.09 (dd, J=6.6 Hz, 6.6 Hz, 1H), 8.42 (s, 1H)

EXAMPLE 63

Methyl 4-Fluoro-2,3-dihydro-1-methyl-7-oxo-1H,7H-pyrido[3,2,1-ij]cinnoline-8-carboxylate (190)

To 1.24 g (4.5 mmol) of the compound (189) obtained in Example 62, 8 ml (87 mmol) of dimethylsulfate was added, and the solution was heated at 120° C. for 3 hours. After air-cooling, the solution was added to 70 ml of ice/water to which 12 g (87 mmol) of anhydrous potassium carbonate was added, and the solution was stirred for 1 hour. The solution was extracted with 100 ml of chloroform, and after drying over magnesium sulfate, the solvent was removed by distillation. The residue was separated by column chromatography (silica gel 40 g, eluent solvent; chloroform:methanol=100:1) to obtain 571 mg of the subject compound (190) in a 46% yield.
Colorless powder:
Melting point: 199°-203° C. (decomp.)
$^1$H-NMR (CDCl$_3$)
2.87 (s, 3H), 3.04 (t, J=5.9 Hz, 2H), 3.50 (t, J=5.9 Hz, 2H), 3.92 (s, 3H), 7.15 (dd, J=8.4 Hz, 8.4 Hz, 1H), 8.35 (dd, J=6.2 Hz, 9.0 Hz, 1H), 8.59 (s, 1H)

EXAMPLE 64

4-Fluoro-2,3-dihydro-1-methyl-7-oxo-1H,7H-pyrido[3,2,1-ij]cinnoline-8-carboxylic acid (191)

To 40 mg (0.14 mmol) of the compound (190) obtained in Example 63, 0.3 ml of concentrated hydrochloric acid and 1.2 ml of acetic acid were added, and the solution was heated at reflux for 3 hours. After air-cooling, 5 ml of water was added to the solution, and deposited crystals were filtered off and washed with water, ethanol and ether in this order to obtain 30 mg of the subject compound (191) in a 79% yield.
Colorless needles:
Melting point: 213° C. (decomp.)
$^1$H-NMR (DMSO-$d_6$)
2.89 (s, 3H), 3.07 (t, J=5.9 Hz, 2H), 3.53 (t, J=6.2 Hz, 2H), 7.59 (dd, J=8.8 Hz, 8.8 Hz, 1H), 8.32 (dd, J=6.9 Hz, 9.2 Hz, 1H), 8.81 (s, 1H)

EXAMPLE 65

4-(Pyrrolidin-1-yl)-2,3-dihydro-1-methyl-7-oxo-1H,7H-pyrido[3,2,1-ij]cinnoline-8-carboxylic acid (192)

15 mg (0.06 mmol) of the compound (191) obtained in Example 64 and 0.1 ml of pyrrolidine were added to 5 ml of acetonitrile, and the solution was heated at reflux for 2 hours. After the solvent was removed by distillation, obtained crystals were dispersed in ethanol and filtered off and washed with ethanol and ether in this order to obtain 15 mg of the subject compound (192) in a 84% yield.
Slightly yellowish prisms:
Melting point: 272° C. (decomp.)
$^1$H-NMR (DMSO-$d_6$)
1.94 (brs, 4H), 2.92 (s, 3H), 3.01 (brs, 2H), 3.54 (brs, 4H), 7.15 (d, J=10.6 Hz, 1H), 8.08 (d, J=9.5 Hz, 1H), 8.60 (s, 1H)

REFERENCE EXAMPLE 32

Ethyl 1-(N-t-Butyloxycarbonyl-N-methylamino)-5,6,7,8-tetrafluoro-1,4-dihydro-4-oxoquinoline-3-carboxylate (193)

A mixture of 28.6 g ethyl 2,3,4,5,6-pentafluorobenzoyl acetate, 23.2 g of ethyl orthoformate and 32.3 g of acetic anhydride was heated at reflux for 8 hours. The solvent was removed by distillation. The obtained oily material was dissolved in 100 ml of methylene chloride, and while cooling on ice, 30 ml of methylene chloride solution containing 14.6 g N-(t-butyloxycarbonyl)-N-methyl-hydrazine was dropped to the solution. The solution was stirred for 2 hours, and the solvent was removed by distillation. The obtained oily material was crystallized from n-hexane, and crystals were filtered off to obtain 18.2 g of ethyl 2-(2,3,4,5,6,-pentafluorobenzoyl)-3-(2-t-butyloxycarbonyl-2-methylhydrazino) acrylate.

The obtained ethyl acrylate and 6.2 g of anhydrous potassium carbonate were added to 50 ml of N,N-dimethylformamide, and the solution was heated at 70° C. for 1 hour. The reaction solution was added to 200 ml of ice/water, and the precipitate was filtered off. The precipitate was dissolved in 200 ml of chloroform, and the solution was washed with water. After drying over magnesium sulfate, the solvent was removed by distillation. The obtained oily material was crystallized from n-hexane to obtain 13.7 g of the subject compound (1.93) in a 33% yield.

REFERENCE EXAMPLE 33

Ethyl 1-(N-Methylamino)-5,6,7,8-tetrafluoro-1,4-dihydro-4-oxoquinoline-3-carboxylate (194)

4.2 g of the compound (193) obtained above was dissolved in 30 ml of ethyl acetate, and while cooling with ice, 40 ml of 4N hydrochloric acid solution in dioxane was added to the solution. The solution was stirred overnight at room temperature, and the solvent was removed by distillation. The residue was dissolved in 100 ml of chloroform, and 50 ml of aqueous 10% sodium carbonate solution was added to the solution. The solution was stirred for 30 minutes at room temperature. The organic layer was separated and after drying over magnesium sulfate, the solvent was removed by distillation. Crystals were dispersed in ether and filtered to obtain 2.9 g of the subject compound (194) in a 91% yield.

EXAMPLE 66

Ethyl 1-[N-{2,2-Bis-(t-butyloxycarbonyl)ethyl}-N-methyl]-amino-5,6,7,8-tetrafluoro-1,4-dihydro-4-oxoquinoline-3-carboxylate (195)

9.5 g of the compound (194) obtained above and 13.7 of di-t-butyl methylenemalonate were added to 90 ml of methylene chloride, and while cooling on ice, 3.3 ml of titanium tetrachloride was dropped to the solution through 40 minutes. The solution was further stirred for 1 hour. The reaction solution was poured into ice/water, and the organic layer was separated. After drying over magnesium sulfate, the solvent was removed by distillation. The obtained oily material was separated by column chromatography (silica gel, eluent solvent; ethyl acetate:methylene chloride=1:20) to obtain 8.6 g of the subject compound (195) in a 47% yield.

Colorless powder:
Melting point: 118°–122° C.
$^1$H-NMR (CDCl$_3$)
1.39 (s,12H), 1.46 (s, 9H), 3.00 (s, 3H), 3.19–3.23 (m, 1H), 3.48–3.62 (m, 2H), 4.40 (q, J=7.1 Hz, 2H), 8.52 (s, 1H)

EXAMPLE 67

Ethyl 3,3-Bis-(t-butyloxycarbonyl)-4,5,6-trifluoro-2,3-dihydro-1-methyl-7-oxo-1H,7H-pyrido[3,2,1-ij]cinnoline-8-carboxylate (196)

10.0 g of the compound (195) obtained in Example 66 was dissolved in 150 ml of dimethylsulfoxide, and the solution was stirred at room temperature. 3.0 g of cesium carbonate was added to the solution, and the solution was stirred at 80° C. for 3 hours. After air-cooling, the reaction solution was added to 500 ml of aqueous 5% citric acid solution and 500 ml of ethyl acetate, and the organic layer was separated from the solution. After drying over magnesium sulfate, the solvent was removed by distillation. The residue was dissolved in ether, and insoluble matter was filtered. The filtrate was removed by distillation, and the residue was separated by column chromatography (silica gel, eluent solvent: chloroform) to obtain 1.6 g of the subject compound (196) in a 17% yield.

Colorless powder:
Melting point: 169°–173° C.
$^1$H-NMR (CDCl$_3$)
1.40 (t, J=7.1 Hz, 3H), 1.49 (s, 18H), 2.76 (s, 3H), 4.04 (s, 2H), 4.39 (q, J=7.1 Hz, 2H), 8.47 (s, 1H)

EXAMPLE 68

4,5,6-Trifluoro-2,3-dihydro-1-methyl-7-oxo-8-ethoxycarbonyl-1H,7H-pyrido[3,2,1-ij]cinnoline-3-carboxylic acid (197)

1.0 g of the compound (196) obtained in Example 67 was dissolved in 2 ml of trifluoroacetic acid, and the solution was heated at 60° C. for 2 hours. The reaction solution was added to 50 ml of isopropyl ether, and deposited solids were filtered off to obtain 0.67 g of the subject compound (197) in a 99% yield.

Colorless powder:
Melting point: 219°–223° C. (decomp.)
$^1$H-NMR (DMSO-d$_6$)
1.28 (t, J=7.1 Hz, 3H), 2.78 (s, 3H) 3.73–3.76 (m, 2H), 4.18–4.25 (m, 3H), 8.45 (s, 1H)

EXAMPLE 69

Ethyl 4,5,6-Trifluoro-2,8-dihydro-1-methyl-7-oxo-1H,7H-pyrido[3,2,1-ij]cinnoline-8-carboxylate (198)

300 mg of the compound (197) obtained in Example 68 was dissolved in 6 ml of N-methylpyrrolidone, and the solution was heated at 160° C. for 3 hours. After air-cooling, the water was added to the reaction solution, and the solution was extracted with chloroform three times. After drying over magnesium sulfate, the solvent was removed by distillation. The residue was separated by column chromatography (silica gel, eluent solvent; chloroform) to obtain 128 mg of the subject compound (198) in a 49% yield.

Colorless powder:
Melting point: 236°–240° C.
$^1$H-NMR (CDCl$_3$)
1.40 (t, J=7.1Hz, 3H), 2.83 (s, 3H), 3.00–3.08, 3.44–3.51 (each m, each 2H), 4.38 (q, J=7.1 Hz, 2H), 8.49 (s, 1H)

EXAMPLE 70

4,5,6-Trifluoro-2,3-dihydro-1-methyl-7-oxo-1H,7H-pyrido[3,2,1-ij]cinnoline-8-carboxylic acid (199)

30 mg of the compound (198) obtained in Example 69 was added to 0.4 ml of acetic acid and 0.1 ml of 12N hydrochloric acid, and the solution was heated at 100° C. for 2 hours. After air-cooling, water was added to the reaction solution, and deposited solids were filtered off and washed with water, ethanol and ether in this order to obtain 22 mg of the subject compound (199) in a 81% yield.

Colorless powder:
Melting point: 255°–260° C. (decomp.)
$^1$H-NMR (DMSO-d$_6$)
2.85 (s, 3H), 3.07–3.10, 3.49–3.55 (each m, each 2H), 8.78 (s, 1H)

EXAMPLE 71

Ethyl 4,5-Difluoro-6-benzylamino-2,3-dihydro-1-methyl-7-oxo-1H,7H-pyrido[3,2,1-ij]cinnoline-8-carboxylate (200)

62 mg of the compound (198) obtained in Example 69 and 50 mg of benzylamine were added to 2 ml of toluene, and the solution was heated at 80° C. for 24 hours. The reaction solution was added to chloroform and was washed with aqueous 5% citric acid solution. After drying over magnesium sulfate, the solvent was removed by distillation. Obtained solids were dispersed in ether and filtered off to obtain 59 mg of the subject compound (200) in a 74% yield.

Colorless powder:
Melting point: 186°–190° C.
$^1$H-NMR (CDCl$_3$)
1.38 (t, J=7.3 Hz, 3H), 2.78 (s, 3H), 2.83–2.90, 3.33–3.39 (each m, each 2H), 4.36 (q, J=7.3 Hz, 2H), 4.68, 4.70 (each d, each J=3.9 Hz, each 1H), 7.22–7.38 (m, 5H), 8.40 (s, 1H), 10.81 (brs, 1H)

EXAMPLE 72

Ethyl 4,5-Difluoro-6-amino-2,3-dihydro-1-methyl-7-oxo-1H,7H-pyrido[3,2,1-ij]cinnoline-8-carboxylate (201)

59 mg of the compound (200) obtained in Example 71 was dissolved in 10 ml of ethanol and 10 ml of acetic acid, and 5 mg of 10% palladium on carbon was added to the solution. the solution was stirred for 24 hours under hydrogen. The catalyst was filtered, and the filtrate was evaporated. The residue was dissolved in chloroform and was washed with saturated aqueous sodium hydrogen-carbonate solution. After drying over magnesium sulfate, the solvent was removed by distillation. Solids were dispersed in ether and filtered off to obtain 27 mg of the subject compound (201) in a 59% yield.

Yellowish powder:
Melting point: 255°–257° C.
$^1$H-NMR (CDCl$_3$)
1.39 (t, J=7.1 Hz, 3H), 2.80 (s, 3H), 2.89, 3.39 (each t, each J=6.0 Hz, each 2H), 4.38 (q, J=7.1 Hz, 2H), 7.03 (brs, 2H), 8.44 (s, 1H)

EXAMPLE 73

6-Amino-4,5-difluoro-2,3-dihydro-1-methyl-7-oxo-1H,7H-pyrido[3,2,1-ij]cinnoline-8-carboxylic acid (202)

20 mg of the compound (201) obtained in Example 72 was added to 0.4 ml of acetic acid and 0.1 ml of 12N hydrochloric acid, and the solution was heated at 100° C. for 2 hours. After air-cooling, the water was added to the reaction solution, and the deposited solids were filtered off and washed consecutively with water, ethanol and ether to obtain 13 mg of the subject compound (202) in a 72% yield.

Slightly yellowish powder:
Melting point: >290° C.
$^1$H-NMR (DMSO-d$_6$)
2.80 (s, 3H), 2.86–2.91, 3.40–3.45 (each m, each 2H), 7.71 (brs, 2H), 8.61 (s, 1H)

EXAMPLE 74

6-Amino-5-fluoro-4-(pyrrolidin-1-yl)-2,3-dihydro-1-methyl-7-oxo-1H,7H-pyrido[3,2,1-ij]cinnoline-8-carboxylic acid (203)

4 mg of the compound (202) obtained in Example 73 and 10 μl of pyrrolidine were added to 1 ml of acetonitrile, and the solution was heated at 80° C. for 3 hours. After air-cooling, the solvent was removed by distillation, and the residue was filtered off and washed with ethanol and ether in this order to obtain 2 mg of the subject compound (203).

Slightly yellowish powder:
Melting point: >290° C.
$^1$H-NMR (CDCl$_3$)
1.97–2.06 (m, 4H), 2.79–2.85 (m, 2H), 2.86 (s, 3H), 3.30–3.35 (m, 2H), 3.44–3.53 (m, 4H), 6.57 (brs, 2H), 8.66 (s, 1H)

EXAMPLE 75

5-Fluoro-4-(3-hydroxy-2-methylazetidin-1-yl)-2,3-dihydro-1-methyl-7-oxo-1H,7H-pyrido[3,2,1-ij]cinnoline-8-carboxylic acid (204)

Procedures of Example 61 were followed to obtain a title compound (204).

Slightly yellowish powder:
Melting point: 261°–263° C.
$^1$H-NMR (DMSO-d$_6$)
1.41 (d, J=6.4 Hz, 3H), 2.87 (s, 3H), 3.82–3.97 (m, 1H), 4.06 (brs, 1H), 4.52–4.70, 4.70–4.87 (each m, each 1H), 5.76 (brs, 1H), 7.78 (d, J=14.7 Hz, 1H), 8.61 (s, 1H)

EXAMPLE 76

4-(3-Amino-2-methylazetidin-1-yl)-5-fluoro-2,3-dihydro-1-methyl-7-oxo-1H,7H-pyrido[3,2,1-ij]cinnoline-8-carboxylic acid Hydro chloride (205)

Procedures of Example 61 were followed to obtain a title compound (205).

Yellowish powder:
Melting point: 205°–210° C.
$^1$H-NMR (DMSO-d$_6$)
1.48 (d, J=6.0 Hz, 3H), 2.56–2.75 (m, 1H), 2.88 (s, 3H), 3.00–3.22 (m, 1H), 3.72 (brs, 1H) 4.10–4.28, 4.75–4.90, 4.90–5.10 (each m, each 1H), 7.81 (d, J=14.2 Hz, 1H), 8.63 (s, 1H), 8.70 (brs, 3H)

EXAMPLE 77

Ethyl 8-Acetoxymethyl-1-(N,N-diacetylamino)-6,7-difluoro-1,4-dihydro-4-oxo-quinoline-3-carboxylate(206)

680 mg(2 mmol) of compound(97) obtained in Example 14 was added to 10 ml of acetic anhydride, and the solution was heated at 110° C. for 4 hours. After air-cooling, the solvent was condensed under reduced pressure and triturated with petroleum ether and filtered off. 776 mg of the title compound (206) was obtained. (yield 90%)

brown amorphous
$^1$H-NMR(DMSO-d$_6$)
1.30(t, J=7.0 Hz, 3H), 2.00(s, 3H), 2.39(s, 6H), 4.28 (q,J=7.0 Hz, 2H), 5.07(s, 2H), 8.30(dd, J=7.0 Hz, J=10.6 Hz,1H), 9.01(s, 1H)

EXAMPLE 78

Ethyl 8-Acetoxymethyl-1-(N-acetylamino)-6,7-difluoro-1,4-dihydro-4-oxo-quinoline-3-carboxylate(207)

424 mg(1 mmol) of compound(206) obtained in Example 77 was dissolved in 10 ml of dimethylsulfoxide. 71 mg(1 mmol) of pyrrolidine dissolved in 1 ml of dimethylsulfoxide was added to the solution through 2 hours, while stirring this solution at room temperare. After stirring at room temperature for 20 hours, 50 ml of water was added to the solution, and stirring was continued for 2 hours. Precipitated crystals were filtrated off and washed with water and ether in this order. After drying in vacuo, 353 mg of the title compound(207) was obtained. (yield 97%)

Slightly yellowish prisms
Melting point: 119°–121° C.
$^1$H-NMR(DMSO-$d_6$)
1.29(t, J=7.0 Hz, 3H), 2.03(s, 6H), 4.27(q, J=7.0 Hz, 2H), 5.40(s, 2H), 8.22(dd, J=7.0 Hz, J=10.6 Hz, 1H), 8.59(s, 1H)

EXAMPLE 79

Ethyl 8-Acetoxymethyl-1-(N-acetyl-N-methylamino)-6,7-difluoro-1,4-dihydro-4-oxoquinoline-3-carboxylate(208)

650 mg(1.7 mmol) of compound(207) obtained in Example 78 was dissolved in 17 ml of N,N-dimethylformamide, and then 510 mg of anhydrous potassium carbonate was added to the solution. 374 mg(2.55 mmol) of methyl iodide was added to the solution while stirring at room temperate. After stirring at room temperature for 20 hours. 50 ml of water was added to the solution, and stirring was continued for 2 hours. Precipitated crystals were filtered out and washed with water and ether in this order. After drying in vacuo 362 mg of the title compound (208) was obtained. (yield 54%)

Slightly yellowish needles
Melting point; 196°–198° C.
$^1$H-NMR(DMSO-$d_6$)
1.30(t, J=7.0 Hz, 3H), 1.72–2.23(m,6H), 3.34(s, 0.3H), 3.56(s, 0.7H), 4.18–4.25(m, 2H), 4.87–5.39(m, 2H), 8.08–8.32(m, 1H), 8.82(s, 0.7H), 8.95(s, 0.3H)

EXAMPLE 80

Ethyl (N-Methylamino)-6,7-difluoro-8-hydroxymethyl-1,4-dihydro-4-oxo-quinoline-3-carboxylate(209)

793 mg(2 mmol) of compound(208) obtained in Example 79 was added to mixture solvent of 4 ml of ethanol and 8 ml of 4N hydrochloricacid solution in dioxane, and then the reaction mixture was heated at 60° C. for 5 hours. After air-cooling, an aqueous saturated sodium hydrogen carbonate solution was dropped to neutralize, while stirring at room temperature. Stirring was continued at room temperature for 2 hours. Precipitated crystals were filtrated out and washed with water and ether in this order. After drying in vacuo 506 mg of the title compound (209) was obtained.

Slightly yellowish needles
Melting point; 217°–222° C.
$^1$H-NMR(DMSO-$d_6$)
1.30(t, J=7.0 Hz, 3H), 2.85(s, 3H), 3.37(s, 3H), 4.24 (q,J=7.0 Hz, 2H), 5.02(brs, 2H), 5.11(brs, 1H),6.93 (m, 1H), 8.10(dd, J=7.0 Hz, J=10.6Hz, 1H), 8.77 (s, 1H)

EXAMPLE 81

Ethyl 3,4-Difluro-1,2-dihydro-1-methyl-6-oxo-1H,6H-pyrido[3,2,1-ij]-indazole-7-carboxylate(210)

437 mg(1.4 mmol) of compound(209) obtained in Example 80 was added to 14 ml of tetrahydrofuran. 283 mg(2.8 mmol) of triethylamine, 266 mg(1.4 mmol) of p-toluenesulufonyl chloride and 10 mg of 4-(dimethylamino)pyridine were added to the reaction mixture, while stirring, and then the reaction mixture was heated at 60° C. for 6 hours. After air-cooling, Precipitated crystals were filtrated out and washed with tetrahydrofuran, water and tetrahydrofuran in this order. 257 mg of the title compound(210) was obtained. (yield 62%)

Colorless needles
Melting point; >215 ° C. (decomp.)
$^1$H-NMR (DMSO-$d_6$)
1.28(t, J=7.0 Hz, 3H), 3.06(s, 3H), 4.21(q, J=7.0 Hz, 2H), 4.87(s, 2H), 7.79(dd, J=7.0 Hz, J=11.4 Hz, 1H), 8.89(s, 1H)

EXAMPLE 82

3,4-Difluro-1,2-dihydro-1-methyl-6-oxo-1H,6H-pyrido[3,2,1-ij]indazole-7-carboxylic acid(211)

88 mg(0.3 mmol) of compound(210) obtained in Example 81 was added to a mixture of 2 ml of formic acid and 2 ml of water, and the reaction mixture was heated at reflux for 6 hours. After air-cooling, Precipitated crystals were filtrated out and washed with water and ether in this order. After drying in vacuo 58 mg of the title compound (211) was obtained. (yield 73 %)

Colorless needles
Melting point; >250° C. (decomp.)
$^1$H-NMR (DMSO-$d_6$)
3.21(s, 3H), 4.99(s, 2H), 8.07(dd, J=7.0 Hz, J=11.1 Hz, 1H), 9.27(s, 1H)

EXAMPLE 83

4-Fluoro-3-(pyrrolidin-1-yl)-1,2-dihydro-1-methyl-6-oxo -1H,6H-pyrido[3,2,1-hi]indazole-7-carboxylic acid(212)

25 mg of compound(211) obtained in. Example 82 and 21 mg of pyrrolidine in 0.6 ml of dimethylsulfoxide were stirred at room temperature for 1 hour. The precipitated solid was filtered off and washed with ether and n-hexane succesively. Whereby, 18 mg of the title compound(212) was obtained.

Yellowish powder
Melting point; >248° C. (decomp.)
$^1$H-NMR(CDCl$_3$/CD$_3$OD=5/1)
2.03(brs, 4H), 3.12(s, 3H), 5.04(s, 2H), 7.67(d, J=14.0 Hz, 1H), 8.70(s, 1H)

EXAMPLE 84

4-(7-Amino-5-azaspiro[2.4]heptan-5-yl)-5-fluoro-2,3-dihydro-1-methyl-7-oxo-1H,7H-pyrido[3,2,1-ij]cinnoline -8-carboxyic acid Hydrochloride(213)

Procedure of Example 6(1) were followed to obtaine the title compound(213).

Yellowish powder
Melting point; 222°–225° C. (decomp.)
$^1$H-NMR(DMSO-$d_6$)
0.75(brs, 2H), 0.87–0.95(m, 1H), 1.12–1.22(m, 1H), 2.90(s, 3H), 3.04–3.19(m, 3H), 4.07(d, J=9.5 Hz, 1H), 4.14–4.25(m, 1H), 7.89(d, J=13.9 Hz, 1H), 8.43(brs, 2H), 8.71(s, 1H)

EXAMPLE 85

4-{(3R)-((1'S)-(2-Aminopropanoylamino)ethyl)pyrrolidin-1-yl}-5-fluoro-2,3-dihydro-1-methyl-7-oxo-1H,7H-pyrido [3,2,1-ij]cinnoline-8-carboxylic acid Hydrochloride (214)

Procedure of Example 11(1) were followed to obtain the title compound(214).
Yellowish prisms:
Melting point: 189°–193° C.
$^1$H-NMR(DMSO-d$_6$)
1.18, 1.34(each d, each J=6.6Hz, each 3H), 1.60–1.75, 2.00–2.13, 2.30–2.40, 2.27–2.86(each m,each 1H), 2.90(s,3H), 3.00–3.10(m,1H), 3.33–3.52(m,5H), 3.69–3.84 (m,2H), 3.89–3.97(m,1H), 7.84(d,J=13.9Hz,1H), 8.14 (brs, 1H), 8.57(d,J=8.4Hz,1H), 8.68(s,1H)

EXAMPLE 86

4-(7-Amino-5-azaspiro[2.4]heptan-5-yl)-5-fluoro-2,3-dihydro-1-methyl-7-oxo-1H,7H-pyrido[3,2,1-ij]cinnoline -8-carboxylic acid Hydrochloride(isomer B)(215)

Procedure of Example 6(1) were followed to obtain the title compound (215).
Yellowish powder:
Melting point: 204°–210° C.
$^1$H-NMR (DMSO-d$_6$)
0.75 (brs, 2H), 0.87–0.95 (m, 1H), 1.12–1.22(m,1H), 2.90(s,3H), 3.04–3.19 (m, 3H), 4.07(d, J=9.5Hz, 1H), 4.14–4.25(m,1H), 7.89(d, J=13.9Hz, 1H), 8.43(brs, 2H), 8.71(s,1H)

EXAMPLE 87

4-(7-Amino-5-azaspiro[2.4]heptan-5-yl)-5-fluoro-2,3-dihydro-1-methyl-7-oxo-1H,7H-pyrido[3,2,1-ij]cinnoline-8-carboxylic acid Hydrochloride(isomer A) (216)

Procedure of Example 6(1) were followed to obtain the title compound(216).
Slightly yellowish powder:
Melting point: 217°–224° C.
$^1$H-NMR(DMSO-d$_6$)
0.75(brs,2H), 0.87–0.95(m,1H), 1.12–1.22(m,1H), 2.90(s,3H), 3.04–3.19(m,3H), 4.07 (d, J=9.5Hz, 1H), 4.14–4.25(m,1H), 7.89(d,J=13.9Hz,1H), 8.43(brs,2H), 8.71(s,1H)

EXAMPLE 80

4-(3-Amino-2-methylazetidin-1-yl)-5-fluoro-2,3-dihydro-1-methyl-7-oxo-1H,7H-pyrido[3,2,1-ij]cinnoline-8-carboxylic acid Hydrochloride(isomer B)(217)

Procedure of Example 61 were followed to obtain the title compound(217).
Slightly yellowish powder:
Melting point: 210°–215° C. (decomp.)
$^1$H-NMR(DMSO-d$_6$)
1.35(d,J=6.4Hz,3H), 2.82(s,3H), 3.52(brs,2H), 3.92–4.11 (m,2H), 7.86 (d,J=14.2Hz,1H), 8.64(s,1H), 8.69 (brs, 3H)

EXAMPLE 89

6-Amino-4-(cis(−)3-amino-4-methylpyrrolidin-1-yl)-5-fluoro-2,3-dihydro-1-methyl-7-oxo-1H,7H-pyrido[3,2,1-ij]cinnoline-8-carboxylic acid Hydrochloride(218)

Procedure of Example 6 were followed to obtain the title compound(218)
Brown amorphous:
$^1$H-NMR(DMSO-d$_6$)
1.13(d,J=13.5Hz,3H), 2.58–2.76(m,2H), 2.84(s,3H), 3.17–4.07(m,7H), 8.45(brs,2H), 8.51(s,1H)

EXAMPLE 90

6-Amino-4-{(3R)-((1'S)-1-aminoethyl)pyrrolidin-1-yl}-5-fluoro-2,3-dihydro-1-methyl-7-oxo-1H,7H-pyrido[3,2,1-ij]cinnoline-8-carboxylic acid Hydrochloride(219)

Procedure of Example 6 were followed to obtain the title compound(219).
Brown powder:
Melting point: 196°–206° C. (decomp.)
$^1$H-NMR(DMSO-d$_6$)
1.29(d,J=5.4Hz,3H), 1.51–1.80, 1.99–2.15, 2.31–2.47 (eac m, each 1H), 2.57–3.06(m,2H), 2.85(s,3H), 3.18–4.41 (m,7H), 8.19(brs,2H), 8.51(s,1H)

EXAMPLE 91

6-Amino-4,5-difluoro-2,3-dihydro-1-methyl-7-oxo-1H, 7H-pyrido[3,2,1-ij]cinnoline-8-carboxylic acid BF$_2$ Chelate(220)

Procedure of Example 18 were followed to obtaine the title compound(220)
Yellowish powder:
Melting point: 257°–261° C. (decomp.)
$^1$H-NMR(DMSO-d$_6$)
2.91(s,1H), 2.99, 3.50, 7.40(each brs,each 2H), 9.12(s,1H)

EXAMPLE 92

6-Amino-4-(piperazin-1-yl)-5-fluoro-2,3-dihydro-1-methyl-7-oxo-1H,7H-pyrido[3,2,1-ij]cinnoline-8-carboxylic acid(221)

Procedure of Example 19 were followed to obtain the title compound(221).
Yellowish prisms:
Melting point: >270° C. (decomp.)
$^1$H-NMR(DMSO-d$_6$)
2.81(s,3H), 2.83(brs,2H), 3.11(brs,4H), 3.34 (brs, 6H), 7.36(brs,2H), 8.54(s,1H)

EXAMPLE 93

3-((3S)-Aminopyrrolidin-1-yl)-4-fluoro-1,2-dihydro-1-methyl-6-oxo-1H,6H-pyrido[3,2,1-hi]indazole-7-carboxyl ic acid(222)

Procedure of Example 83 were followed to obtain the title compound(222).
Slightly yellowish powder:
Melting point: >270° C. (decomp.)
$^1$H-NMR (DMSO-d$_6$)
1.61–1.72, 1.89–1.72 (each m,each 1H), 3.09(s,3H), 3.69–3.94(m,3H), 5.09(s,2H), 7.56(d,J=14.5Hz,1H), 8.93(s,1H)

EXAMPLE 94

4-Fluoro-3-(4-methylpiperazin-1-yl)-1,2-dihydro-1-methyl-6-oxo-1H,6H-pyrido[3,2,1-hi]indazole-7-carboxylic acid(223)

Procedure of Example 83 were followed to obtain the title compound(223).
Colorless powder:
Melting point: >278° C. (decomp.)
1H-NMR(DMSO-d$_6$)
2.24(s,3H), 2.50(s,4H), 3.14(s,3H), 3.34(s,4H), 5.04(s,2H), (d,J=12.7Hz,1H), 9.07(s,1H)

EXAMPLE 95

4-Fluoro-3-(piperazin-1-yl)-1,2-dihydro-1-methyl-6-oxo-1H,6H-pyrido[3,2,1-hi]indazole-7-carboxylic acid(224)

Procedure of Example 83 were followed to obtain the title compound(224).
Colorless powder:
Melting point: 254°-256° C. (decomp.)
1H-NMR(DMSO-d$_6$)
2.82(s,4H), 3.15(s,3H), 3.24(s,4H), 5.02(s,2H), 7.67 (d,J=12.8Hz,1H), 9.05(s,1H)

EXAMPLE 96

4-Fluoro-3-(cis(−)3-amino-4-methylpyrrolidin-10yl)-1,2-dihydro-1-methyl-6-oxo-1H,6H-pyrido[3,2,1-hi]indazole -7-carboxylic acid(225)

Procedure of Example 83 were followed to obtain the title compound(225).
Yellowish powder:
Melting point: >196° C. (decomp.)
$^1$H-NMR(DMSO-d$_6$)
1.00(d,J=6.6Hz,3H), 2.14-2.23(m,1H), 3.09(s,3H), 3.73-3.81, 3.86-3.93(each m,each 1H), 5.09(s,2H), 7.54(d,J=14.5Hz,1H), 8.92(s,1H)

EXAMPLE 97

5-Fluoro-4-Piperidino-2,3-dihydro-1-methyl-7-oxo-1H,7H -pyrido[3,2,1-ij]cinnoline-8-carboxylic acid(226)

Procedure of Example 19 were followed to obtain the title compound(226).
Colorless powder:
Melting point: 261°-262° C. (decomp.)
$^1$H-NMR(DMSO-d$_6$)
1.65(brs,6H), 2.90(s,3H), 3.04, 3.46(each t,each J=5.9Hz, each 2H), 3.21(brs,4H), 7.90(d,J=12.8Hz,1H), 8.73(s,1H)

What is claimed is:

1. A tricyclic compound represented by formula (1) or a pharmaceutically acceptable salt thereof,

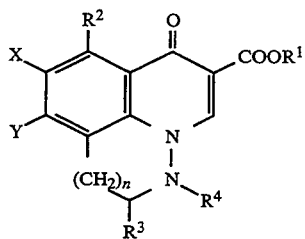

wherein R$^1$ is hydrogen, lower alkyl, benzyl, phenyl, lower alkanoyloxy-lower alkyl, lower alkoxycarbonyloxy-lower alkyl, lower alkoxymethyl, phthalidyl, di-lower alkyl, amino-lower alkyl or (5-methyl-2-oxo-1,3-dioxol-4-yl)-methyl;

wherein R$^2$ is hydrogen, halogen or amino group which may be substituted by, benzylidene, hydroxy-benzylidene, mono-, di-, or triphenyl(lower)alkyl or an acyl group selected from lower alkanoyl, mono-, di- or trihalo(lower)alkanoyl, lower-alkoxycarbonyl, carbamoyl, benzoyl, toluoyl, naphthoyl, phenyl(lower)alkanoyl, phenyloxycarbonyl, naphthyloxycarbonyl, phenoxy(lower)alkanoyl, phenylglyoxyloyl, naphthylglyoxyloyl, benzyloxycarbonyl and p-nitrobenzyloxycarbonyl;

wherein R$_3$ is hydrogen or lower alkyl;

wherein R$^4$ is hydrogen, lower alkyl which may he substituted by hydroxyl, halogen or lower alkoxy, acyl group selected from lower alkanoyl, lower alkoxycarbonyl, benzoyl and phenoxycarbonyl or phenyl-lower alkyl;

wherein X is hydrogen or halogen;

wherein Y is (i) halogen, amino, cyclo-lower alkylamino or mono- or di-lower alkylamino, (ii) a cyclic amino group represented by one of the following formulae (a')-(t):

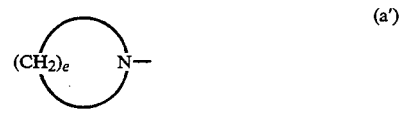

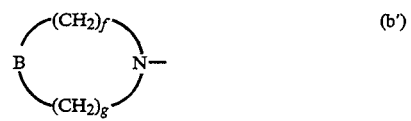

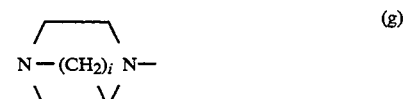

-continued (i) 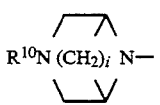

(j) 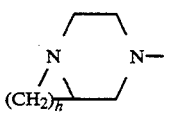

(k) 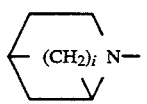

(l) 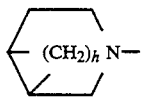

(m) 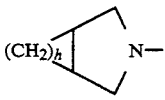

(n) 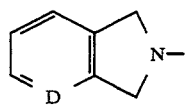

(o) 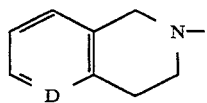

(p) 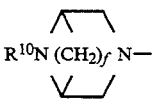

(q) 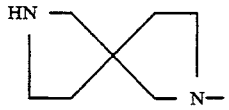

(r) 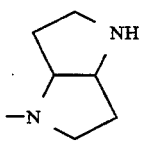

(s) 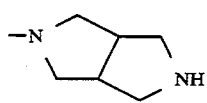

(t) 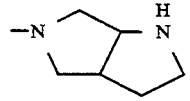

wherein B is oxygen, sulfur or $NR^{10}$,
wherein $R^{10}$ is hydrogen, hydroxyl, lower alkyl, cyclo-lower alkyl, phenyl-lower alkyl, lower alkenyl, hydroxy-lower alkyl, or phenyl-lower alkyl or acyl group selected from lower alkanoyl, lower alkoxycarbonyl, benzoyl and phenoxycarbonyl;

D is CH or N,
e is 3, 4 or 5,
f is 1, 2 or 3,
g is 0, 1 or 2,
h is 3 or 4 and
i is 1 or 2,
wherein when Y is a group of formula b', f and g are each equal to 2,
wherein said cyclic amino group may be substituted by one or more substituents selected from the group consisting of lower alkyl; lower alkenyl; phenyl-lower alkyl; phenyl; hydroxyl; hydroxy-lower alkyl; amino group or amino-lower alkyl group wherein the amino group may be substituted by lower alkyl, lower cycloalkyl, lower alkenyl, phenyl-lower alkyl, phenyl, an acyl group selected from lower alkanoyl, lower alkoxycarbonyl, benzoyl and phenoxycarbonyl, or a peptide or amino acid group selected from the group consisting of glycyl-, leucyl-, valyl-, alanyl-, phenylalanyl-, alanyl-alanyl-, glycyl-valyl- and glycyl-glycyl-valyl-, each amino group of which may be substituted by an acyl group selected from lower alkanoyl, lower alkoxycarbonyl, benzoyl and phenoxycarbonyl; one of cyclic amino groups (a')-(t); halogen; lower alkoxy-lower alkyl; halo-lower alkyl; acetoxy; benzoyloxy; acetoxymethyl; benzoyloxymethyl; acyl group selected from lower alkanoyl, lower alkoxycarbonyl, benzoyl and phenoxycarbonyl; carboxyl; carboxy-lower alkyl; alkoxycarbonyl-lower alkyl; mercapto; lower alkylthio; cyano and nitro;

(iii) lower alkyl which may be mono- or di-substituted by carboxyl, alkoxycarbonyl or cyano, (iv) cyclo-lower alkenyl which may be substituted by an oxo group, (v) a group represented by a formula $R^5$—$(CH_2)_m$—A— wherein $R^5$ is hydrogen, amino which may be substituted by substituents selected from the substituents listed for the cyclic amino group above, azetidinyl, pyrrolidinyl or lower cyclo alkyl, wherein A is oxygen or sulfur, and
wherein m is an integer of 0–3, or (vi) a group represented by a formula $R^6$—$SO_2$—O— wherein $R^6$ is lower alkyl, halo-lower alkyl or phenyl which may be mono-, di- or tri-substituted by lower alkyl; and
wherein n is 1.

2. The compound of claim 1, wherein $R^1$, $R^2$ and $R^3$ are hydrogen atom, $R^4$ is a methyl group, and X is a halogen atom.

3. The compound of claim 2, wherein Y is a cyclic amino group (ii).

4. The compound of claim 3, wherein Y is represented by formula (a) or (b):

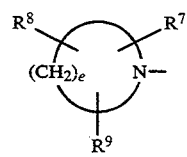

-continued

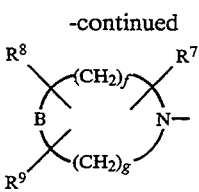
(b)

wherein B is oxygen, sulfur or NR$^{10}$,
wherein R$^{10}$ is hydrogen, hydroxyl, lower alkyl, cyclo-lower alkyl, phenyl-lower alkyl, lower alkenyl, hydroxy-lower alkyl, or phenyl-lower alkyl or acyl group selected from lower alkanoyl, lower alkoxycarbonyl, benzoyl and phenoxycarbonyl;
 e is 3, 4 or 5,
 f is 2,
 g is 2,
 h is 3 or 4 and
 i is 1 or 2,
wherein R$^7$, R$^8$ and R$^9$ are either the same or different and are each selected from the group consisting of hydrogen; lower alkyl; lower alkenyl; phenyl-lower alkyl; phenyl; hydroxyl; hydroxy-lower alkyl; amino group or amino-lower alkyl group wherein the amino group may be substituted by lower alkyl, lower cycloalkyl, lower alkenyl, phenyl-lower alkyl, phenyl, an acyl group selected from lower alkanoyl, lower alkoxycarbonyl, benzoyl and phenoxycarbonyl; a pyrrolidinyl group; a piperidino group; and azetidinyl group; halogen; lower alkoxy-lower alkyl; halo-lower alkyl; acetoxy; benzoyloxy; acetoxymethyl; benzoyloxymethyl; acyl group selected from lower alkanoyl, lower alkoxycarbonyl, benzoyl and phenoxycarbonyl; carboxyl; carboxy-lower alkyl; alkoxycarbonyl-lower alkyl; mercapto; lower alkylthio; cyano and nitro.

5. An antimicrobial agent containing a tricyclic compound as claimed in claim 1 as an active ingredient.

* * * * *